US012714716B2

(12) United States Patent
Wu et al.

(10) Patent No.: US 12,714,716 B2
(45) Date of Patent: Aug. 25, 2026

(54) COMPOUNDS FOR INHIBITION OF INFLAMMATION

(71) Applicant: Children's Medical Center Corporation, Boston, MA (US)

(72) Inventors: Hao Wu, Brookline, MA (US); Judy Lieberman, Brookline, MA (US); Jun Hu, Boston, MA (US); Xing Liu, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 17/255,092

(22) PCT Filed: Jun. 27, 2019

(86) PCT No.: PCT/US2019/039499

§ 371 (c)(1),
(2) Date: Dec. 22, 2020

(87) PCT Pub. No.: WO2020/006229

PCT Pub. Date: Jan. 2, 2020

(65) Prior Publication Data

US 2021/0267996 A1 Sep. 2, 2021

Related U.S. Application Data

(60) Provisional application No. 62/690,788, filed on Jun. 27, 2018.

(51) Int. Cl.

| | |
|---|---|
| ***A61K 31/555*** | (2006.01) |
| ***A61K 31/10*** | (2006.01) |
| ***A61K 31/225*** | (2006.01) |
| ***A61K 31/385*** | (2006.01) |
| ***A61K 31/4025*** | (2006.01) |
| ***A61K 31/428*** | (2006.01) |
| ***A61K 31/433*** | (2006.01) |
| ***A61K 31/444*** | (2006.01) |
| ***A61K 31/4545*** | (2006.01) |
| ***A61K 31/497*** | (2006.01) |
| ***A61K 31/5377*** | (2006.01) |
| ***A61K 31/54*** | (2006.01) |
| ***A61K 31/553*** | (2006.01) |
| ***G01N 33/543*** | (2006.01) |

(52) U.S. Cl.

CPC ............ *A61K 31/555* (2013.01); *A61K 31/10* (2013.01); *A61K 31/225* (2013.01); *A61K 31/385* (2013.01); *A61K 31/4025* (2013.01); *A61K 31/428* (2013.01); *A61K 31/433* (2013.01); *A61K 31/444* (2013.01); *A61K 31/4545* (2013.01); *A61K 31/497* (2013.01); *A61K 31/5377* (2013.01); *A61K 31/54* (2013.01); *A61K 31/553* (2013.01); *G01N 33/5432* (2013.01); *G01N 2500/20* (2013.01)

(58) Field of Classification Search

CPC .... A61K 31/436; A61K 31/277; A61K 45/06; A61P 9/06

See application file for complete search history.

(56) References Cited

U.S. PATENT DOCUMENTS

| | | | | |
|---|---|---|---|---|
| 4,870,101 | A * | 9/1989 | Ku ............................ | A61P 9/10 514/476 |
| 5,304,121 | A | 4/1994 | Sahatjian | |
| 5,886,026 | A | 3/1999 | Hunter et al. | |
| 6,099,562 | A | 8/2000 | Ding et al. | |
| 6,288,110 | B1 | 9/2001 | Marikovsky | |
| 6,803,031 | B2 | 10/2004 | Rabinowitz et al. | |
| 9,453,226 | B2 | 9/2016 | Ambati et al. | |
| 10,886,008 | B2 | 1/2021 | Kamens et al. | |
| 2001/0016600 | A1 | 8/2001 | Kennedy et al. | |
| 2005/0181354 | A1 | 8/2005 | Estep | |
| 2009/0274677 | A1 | 11/2009 | Isaacs et al. | |
| 2010/0135983 | A1 * | 6/2010 | Hyde .................. | A61K 31/439 514/252.19 |
| 2011/0196616 | A1 | 8/2011 | Gunn | |
| 2012/0030779 | A1 | 2/2012 | Benjamin et al. | |
| 2015/0139973 | A1 | 5/2015 | Steinfeld et al. | |
| 2016/0292380 | A1 | 10/2016 | Cho et al. | |
| 2017/0342496 | A1 | 11/2017 | Zhang et al. | |

(Continued)

FOREIGN PATENT DOCUMENTS

| | | |
|---|---|---|
| GB | 201804514.6 | 3/2018 |
| NZ | 545 724 | 11/2007 |

(Continued)

OTHER PUBLICATIONS

Szabo G, Petrasek J. Inflammasome activation and function in liver disease. Nat Rev Gastroenterol Hepatol. Jul. 2015;12(7):387-400. (Year: 2015).*

(Continued)

*Primary Examiner* — Lauren Wells

(74) *Attorney, Agent, or Firm* — Fish & Richardson P.C.

(57) ABSTRACT

The present application provides chemical compounds useful, for example, in inhibiting gasdermin pore formation in a CA cell, inhibiting inflammasome-mediated death of a cell (pyroptosis); inhibiting cytokine secretion from a cell, inhibiting an inflammatory caspase in a cell, and/or covalently reacting with a cysteine of a gasdermin protein in a cell. These compounds are also useful in treating or preventing diseases or conditions in which inflammasome activation is implicated in pathogenesis. One example of such disease or condition is sepsis.

3 Claims, 59 Drawing Sheets

(56) References Cited

U.S. PATENT DOCUMENTS

| | | | |
|---|---|---|---|
| 2019/0034581 | A1 | 1/2019 | Aliper et al. |
| 2019/0228840 | A1 | 7/2019 | Kamens et al. |
| 2019/0381132 | A1 | 12/2019 | Shu et al. |

FOREIGN PATENT DOCUMENTS

| | | | |
|---|---|---|---|
| WO | WO-9934784 A2 * | 7/1999 | ............ A61K 31/27 |
| WO | WO 2009/062174 | 5/2009 | |
| WO | WO-2010065118 A1 * | 6/2010 | ............ A61K 31/00 |
| WO | WO 2012/164525 | 12/2012 | |
| WO | WO 2014/175542 | 10/2014 | |
| WO | WO 2016/086008 | 6/2016 | |
| WO | WO 2017/049103 | 6/2016 | |
| WO | WO 2018/081309 | 5/2018 | |
| WO | WO 2019/094053 | 5/2019 | |
| WO | WO 2019/147725 | 8/2019 | |
| WO | WO 2019/180450 | 9/2019 | |
| WO | WO 2020/006229 | 1/2020 | |

OTHER PUBLICATIONS

Annane, Djillali et al. "Corticosteroids for treating sepsis." The Cochrane database of systematic reviews vol. 2015,12 CD002243. Dec. 3, 2015, doi:10.1002/14651858.CD002243.pub3 (Year: 2015).*

Yang, M et al. "Chloroquine Inhibits HMGB1 Inflammatory Signaling and Protects Mice from Lethal Sepsis." Biochemical pharmacology. Aug. 1, 2013; 86(3): 410-418. (Year: 2013).*

Karki et al. Inflammasomes and Cancer, Cancer Immunol Res (2017)5(2):94-99 (Year: 2017).*

Yerramothu, P., Vijay, A. & Willcox, M. Inflammasomes, the eye and anti-inflammasome therapy. Eye 32, 491-505 (2018). (Year: 2018).*

Mayo Clinic. Optic Neuritis. Retrieved from the internet on Oct. 26, 2022, https://www.mayoclinic.org/diseases-conditions/optic-neuritis/symptoms-causes/syc-20354953. (Year: 2022).*

Pubchem. Thiram. Retrieved from the Internet on Mar. 6, 2024. https://pubchem.ncbi.nlm.nih.gov/compound/5455#section=2D-Structure (Year: 2024).*

CDC. Methicillin-resistant *Staphylococcus aureus* (MRSA). Retrieved from the WayBack Machine on Mar. 6, 2023, https://web.archive.org/web/20180626085038/https://www.cdc.gov/mrsa/community/index.html. Published Jun. 26, 2018 (Year: 2018).*

Phillips et al. Disulfiram inhibits the in vitro growth of methicillin resistant *Staphylococcus aureus*. Antimicrobial Agents and Chemotherapy, vol. 35, Issue 4. Published 1991. (Year: 1991).*

LungCancer.net. From Terminal Lung Cancer to Chronic Condition. Retrieved from the internet on Mar. 13, 2024, https://lungcancer.net/living/terminal-cancer-chronic-condition. Published Feb. 2, 2019. (Year: 2019).*

ApolloMD. Are Sepsis and MRSA the Same? Retrieved from the Internet on Nov. 13, 2024, https://apollomd.com/glossary/sepsis-mrsa-same/#:~:text=Sepsis%20and%20MRSA%20(methicillin%2Dresistant,Streptococcal%20infections%2C%20or%20Pneumococcal%20infections. (Year: 2024).*

Martínez ML, Plata-Menchaca EP, Ruiz-Rodríguez JC, Ferrer R. An approach to antibiotic treatment in patients with sepsis. J Thorac Dis. Mar. 2020;12(3):1007-1021. (Year: 2020).*

Aliper et al., "Deep learning applications for predicting pharmacological properties of drugs and drug repurposing using transcriptomic data," Molecular Pharmaceutics, Jul. 5, 2016, 13(7):2524-30.

artofficialintelligence.com, "AI to accelerate drug discovery for aging and age-associated diseases," May 17, 2017, retrieved Jan. 25, 2018 from URL <https://www.onartificialintelligence.com/journal/print-articles.asp?articleids=11058., 2 pages.

Bray et al., "Cell Painting, a high-content image-based assay for morphological profiling using multiplexed fluorescent dyes," Nature Protocols, Sep. 2016, 11(9):1757-74.

Carpenter et al., "CellProfiler: image analysis software for identifying and quantifying cell phenotypes," Genome Biology, Apr. 2006, 7(10):1-1.

Cheung et al., "Cinnamic compound metabolism in human skin and the role metabolism may play in determining relative sensitisation potency," Journal of Dermatological Science, Feb. 1, 2003, 31(1):9-19.

Cole et al., "Predicting brain age with deep learning from raw imaging data results in a reliable and heritable biomarker," NeuroImage, Dec. 1, 2017, 163:115-24.

Conboy et al., "Heterochronic parabiosis for the study of the effects of aging on stem cells and their niches," Cell Cycle, Jun. 15, 2012, 11(12):2260-7.

Conboy et al., "Rejuvenation of aged progenitor cells by exposure to a young systemic environment," Nature, Feb. 2005, 433(7027):760-4.

Deng et al., "Imagenet: A large-scale hierarchical image database," 2009 Conference on Computer Vision and Pattern Recognition, Jun. 20, 2009, 248-55.

D'Orazio et al., "UV radiation and the skin," International Journal of Molecular Sciences, Jun. 2013, 14(6):12222-48.

Harrison et al., "Rapamycin fed late in life extends lifespan in genetically heterogeneous mice," Nature, Jul. 2009, 460(7253):392-5.

He et al., "Deep residual learning for image recognition," Proceedings of the IEEE Conference on Computer Vision and Pattern Recognition 2016, Dec. 10, 2015, 770-8.

Hu et al., "FDA-approved disulfiram inhibits pyroptosis by blocking gasdermin D pore formation," Nature Immunology, Jul. 2020, 21(7):736-45.

Ianevski et al., "SynergyFinder: a web application for analyzing drug combination dose-response matrix data," Bioinformatics, Aug. 1, 2017, 33(15):2413-5.

Kamentsky et al., "Improved structure, function and compatibility for CellProfiler: modular high-throughput image analysis software," Bioinformatics, Apr. 15, 2011, 27(8):1179-80.

Kingma et al., "Adam: A method for stochastic gradient descent," ICLR: International Conference on Learning Representations, May 7, 2015, 15 pages.

Langer, "New methods of drug delivery," Science, Sep. 28, 1990, 249(4976):1527-33.

Lederer et al., "Additive dose response models: explicit formulation and the loewe additivity consistency condition," Frontiers in Pharmacology, Feb. 6, 2018, 9:31, 11 pages.

Lin et al., "Disulfiram can inhibit MERS and SARS coronavirus papain-like proteases via different modes," Antiviral Research, Feb. 1, 2018, 150:155-63.

Ljosa et al., "Comparison of methods for image-based profiling of cellular morphological responses to small-molecule treatment," Journal of Biomolecular Screening, Dec. 2013, 18(10):1321-9.

Loo et al., "Blockage of drug resistance in vitro by disulfiram, a drug used to treat alcoholism," Journal of the National Cancer Institute., Jun. 7, 2000, 92(11):898-902.

Lopez-Berestein et al., "Liposomes in the therapy of infectious diseases and cancer," Proceedings of a Ciba-Geigy-Squibb-UCLA Colloquium, Lake Tahoe, CA, Feb. 16-20, 1989, 26 pages.

McCarthy, "Disulfiram inhibits inflammatory gatekeeper protein: Could it be helpful in COVID-19?," Boston Children's Press Release, May 10, 2020, 5 pages.

PCT International Preliminary Report on Patentability in International Appln. No. PCT/US2019/014826, dated Aug. 6, 2020, 10 pages.

PCT International Search Report and Written Opinion in International Appln. No. PCT/US2019/014826, dated Apr. 11, 2019, 11 pages.

Pelaz et al., "Diverse applications of nanomedicine," ACS Nano, Mar. 28, 2017, 11(3):2313-81.

Phillip et al., "Biophysical and biomolecular determination of cellular age in humans," Nature Biomedical Engineering, Jul. 11, 2017, 1(7):1-2.

Puri et al., "Lipid-based nanoparticles as pharmaceutical drug carriers: from concepts to clinic," Critical Reviews in Therapeutic Drug Carrier Systems, Jun. 14, 2010, 26(6), 46 pages.

(56) References Cited

OTHER PUBLICATIONS

Putin et al., "Deep biomarkers of human aging: application of deep neural networks to biomarker development," Aging, May 2016, 8(5):1021-30.
Sauna et al., "The molecular basis of the action of disulfiram as a modulator of the multidrug resistance-linked ATP binding cassette transporters MDR1 (ABCB1) and MRP1 (ABCC1)," Molecular Pharmacology, Mar. 1, 2004, 65(3):675-84.
Treat, "Liposome encapsulated doxrubicin: Preliminary results of phase I and Phase II Trials," Liposomes in the Therapy of Infectious Diseases and Cancer, Jan. 1989, 89:353-66.
Uno et al., "Lifespan-regulating genes in C. elegans," npj Aging and Mechanisms of Disease Jun. 2, 2016, 2(1):1-8.
US Office Action in U.S. Appl. No. 16/255,366, dated Apr. 1, 2019, 10 pages.
US Office Action in U.S. Appl. No. 16/255,366, dated Feb. 13, 2020, 15 pages.
US Office Action in U.S. Appl. No. 16/255,366, dated Jun. 26, 2020, 17 pages.
US Office Action in U.S. Appl. No. 16/255,366, dated Sep. 18, 2019, 11 pages.
Viola-Rhenals et al., "Recent advances in Antabuse (disulfiram): the importance of its metal-binding ability to its anticancer activity," Current Medicinal Chemistry, Jan. 1, 2018, 25(4):506-24.
Wakaskar, "General overview of lipid-polymer hybrid nanoparticles, dendrimers, micelles, liposomes, spongosomes and cubosomes," Journal of Drug Targeting, Apr. 21, 2018, 26(4):311-8.
Weindruch et al., "The retardation of aging in mice by dietary restriction: longevity, cancer, immunity and lifetime energy intake," The Journal of Nutrition, Apr. 1, 1986, 116(4):641-54.
Zheng, "synergyfinder: Calculate and Visualize Synergy Scores for Drug Combinations, R package version 2.4.13," retrieved Oct. 22, 2021 from URL <http://synergyfinder.org>, 7 pages.
EP European Search Report in European Appln. No. 19826440.0, dated Jul. 23, 2021.
Foley et al., "Ritonavir and disulfiram have potential to inhibit caspase-1 mediated inflammation and reduce neurological sequelae after minor blast exposure," Medical Hypotheses, Feb. 1, 2009, 72(2):150-2.
Hu et al., "Identification of pyroptosis inhibitors that target a reactive cysteine in gasdermin D," BioRxiv, Jan. 1, 2018, 365908, 37 pages.
Kawarski et al., "Lazaroids U83836E and U74389G are Potent, Time-Dependent Inhibitors of Caspase-1," Chemical Biology & Drug Design, Nov. 2015, 86(5):1049-54.
PCT International Preliminary Report on Patentability in International Appln. No. PCT/US2019/039499, dated Jan. 7, 2021, 8 pages.
PCT International Search Report and Written Opinion in International Appln. No. PCT/US2019/039499, dated Nov. 4, 2021, 19 pages.
Baldwin et al., "Inhibiting the inflammasome: a chemical perspective," Journal of Medicinal Chemistry, Mar. 10, 2016, 59(5):1691-710.
Broz et al., "Inflammasomes: mechanism of assembly, regulation and signalling," Nature Reviews Immunology, Jul. 2016, 16(7):407-20.
Castillo-Villanueva et al., "Disulfiram as a novel inactivator of *Giardia lamblia* triosephosphate isomerase with antigiardial potential," International Journal for Parasitology: Drugs and Drug Resistance, Dec. 1, 2017, 7(3):425-32.
Chen et al., "Pyroptosis is driven by non-selective gasdermin-D pore and its morphology is different from MLKL channel-mediated necroptosis," Cell Research, Sep. 2016, 26(9):1007-20.
Chu et al., "The oxidized phospholipid oxPAPC protects from septic shock by targeting the non-canonical inflammasome in macrophages," Nature Communications, Mar. 8, 2018, 9(1):1-6.
Degterev et al., "Identification of RIP1 kinase as a specific cellular target of necrostatins," Nature Chemical Biology, May 2008, 4(5):313-21.
Ding et al., "Pore-forming activity and structural autoinhibition of the gasdermin family," Nature, Jul. 2016, 535(7610):111-6.
Frangogiannis et al., "The inflammatory response in myocardial infarction," Cardiovascular Research, Jan. 1, 2002, 53(1):31-47.
Hagn et al., "Assembly of phospholipid nanodiscs of controlled size for structural studies of membrane proteins by NMR," Nature Protocols, Jan. 2018, 13(1):79-98.
He et al., "Gasdermin D is an executor of pyroptosis and required for interleukin-1β secretion," Cell Research, Dec. 2015. 25(12):1285-98.
Illum, "Is nose-to-brain transport of drugs in man a reality?," Journal of Pharmacy and Pharmacology, Jan. 2004, 56(1):3-17.
Illum, "Transport of drugs from the nasal cavity to the central nervous system," European Journal of Pharmaceutical Sciences, Mar. 2000, 11(1):1-8.
Irrera et al., "Bay 11-7082 inhibits the NF-κB and NLRP3 inflammasome pathways and protects against IMQ-induced psoriasis," Clinical Science, Mar. 1, 2017, 131(6):487-98.
Jo et al., "Molecular mechanisms regulating NLRP3 inflammasome activation," Cellular & Molecular Immunology, Mar. 2016, 13(2):148-59.
Juliana et al., "Anti-inflammatory compounds parthenolide and Bay 11-7082 are direct inhibitors of the inflammasome, " Journal of Biological Chemistry, Mar. 26, 2010, 285(13):9792-802.
Kayagaki et al., "Caspase-11 cleaves gasdermin D for non-canonical inflammasome signalling," Nature, Oct. 2015, 526(7575):666-71.
Kayagaki et al., "Non-canonical inflammasome activation targets caspase-11," Nature, Nov. 2011, 479(7371):117-21.
Krishnan et al., "The anti-inflammatory compound Bay-11-7082 is a potent inhibitor of protein tyrosine phosphatases," The FEBS Journal, Jun. 2013, 280(12):2830-41.
Kulkarni et al., "Disulfides as Pseudo-irreversible Inhibitors of the Lymphoid Tyrosine Phosphatase," ChemMedChem, Sep. 2013, 8(9):1561-1568.
Lamkanfi et al., "Inflammasomes and their roles in health and disease," Annual Review of Cell and Developmental Biology, Nov. 10, 2012, 28:137-61.
Liu et al., "Inflammasome-activated gasdermin D causes pyroptosis by forming membrane pores," Nature, Jul. 2016, 535(7610):153-8.
Lupfer et al., "Reactive oxygen species regulate caspase-11 expression and activation of the non-canonical NLRP3 inflammasome during enteric pathogen infection," PLoS Pathog, Sep. 25, 2014, 10(9):e1004410.
Moon et al., "NOX4-dependent fatty acid oxidation promotes NLRP3 inflammasome activation in macrophages," Nature Medicine, Sep. 2016, 22(9):1002-12.
Nair et al., "A simple practice guide for dose conversion between animals and human," Journal of Basic and Clinical Pharmacy, Mar. 2016, 7(2):27, 5 pages.
Nakahira et al., "Autophagy proteins regulate innate immune responses by inhibiting the release of mitochondrial DNA mediated by the NALP3 inflammasome," Nature Immunology, Mar. 2011, 12(3):222-31.
Nasr et al., "Covalently circularized nanodiscs for studying membrane proteins and viral entry," Nature Methods, Jan. 2017, 14(1):49-52.
Nobel et al., "Disulfiram is a potent inhibitor of proteases of the caspase family," Chemical Research in Toxicology, Dec. 16, 1997, 10(12):1319-24.
Petersen, "The pharmacology and toxicology of disulfiram and its metabolites," Acta Psychiatrica Scandinavica, Nov. 1992, 86(S369):7-13.
Pierce et al., "Novel inhibitors of cytokine-induced IκBα phosphorylation and endothelial cell adhesion molecule expression show anti-inflammatory effects in vivo," Journal of Biological Chemistry, Aug. 22, 1997, 272(34):21096-103.
Rathinam et al., "Regulation of inflammasome signaling," Nature Immunology, Apr. 2012, 13(4):333.
Rathkey et al., "Chemical disruption of the pyroptotic pore-forming protein gasdermin D inhibits inflammatory cell death and sepsis," Science Immunology, Aug. 24, 2018, 3(26).

(56) References Cited

OTHER PUBLICATIONS

Rauert-Wunderlich et al., "The IKK inhibitor Bay 11-7082 induces cell death independent from inhibition of activation of NFκB transcription factors," PloS one, Mar. 20, 2013, 8(3):e59292.
Rongvaux et al., "Apoptotic caspases prevent the induction of type I interferons by mitochondrial DNA," Cell, Dec. 18, 2014, 159(7):1563-77.
Ruan et al., Cryo-EM structure of the gasdermin A3 membrane pore, Nature, May 2018, 557(7703):62-7.
Russo et al., "Active caspase-1 induces plasma membrane pores that precede pyroptotic lysis and are blocked by lanthanides," The Journal of Immunology, Aug. 15, 2016, 197(4):1353-67.
Sanchez et al., "Prediction of reversibly oxidized protein cysteine thiols using protein structure properties," Protein Science, Mar. 2008, 17(3):473-81.
Sborgi et al., "Structure and assembly of the mouse ASC inflammasome by combined NMR spectroscopy and cryo-electron microscopy," Proceedings of the National Academy of Sciences, Oct. 27, 2015, 112(43):13237-42.
Shen et al., "Determination of in vivo adducts of disulfiram with mitochondrial aldehyde dehydrogenase," Biochemical Pharmacology, Mar. 1, 2001, 61(5):537-45.
Shi et al., "Cleavage of GSDMD by inflammatory caspases determines pyroptotic cell death," Nature, Oct. 2015, 526(7575):660-5.
Skrott et al., "Alcohol-abuse drug disulfiram targets cancer via p97 segregase adaptor NPL4," Nature, Dec. 2017, 552(7684):194-9.
Sollberger et al., "Gasdermin D plays a vital role in the generation of neutrophil extracellular traps," Science Immunology, Aug. 24, 2018, 3(26).
Sun et al., "Mixed lineage kinase domain-like protein mediates necrosis signaling downstream of RIP3 kinase," Cell, Jan. 20, 2012, 148(1-2):213-27.
White et al., "Apoptotic caspases suppress mtDNA-induced STING-mediated type I IFN production," Cell, Dec. 18, 2014, 159(7):1549-62.
Wright et al., "Disulfiram treatment of alcoholism," The American Journal of Medicine, Jun. 1, 1990, 88(6):647-55.
Zanoni et al., "An endogenous caspase-11 ligand elicits interleukin-1 release from living dendritic cells," Science, Jun. 3, 2016, 352(6290):1232-6.
Zhang et al., "A simple statistical parameter for use in evaluation and validation of high throughput screening assays," Journal of Biomolecular Screening, Apr. 1999, 4(2):67-73.
Zhong et al., "NF-κB restricts inflammasome activation via elimination of damaged mitochondria," Cell, Feb. 25, 2016, 164(5):896-910.
Zhou et al., "A role for mitochondria in NLRP3 inflammasome activation," Nature, Jan. 2011, 469(7329):221-5.
EP Office Action in European Appln. No. 19826440.0, mailed on May 8, 2024, 7 pages.
Hu, "The summary diagram of discovered host immunological pathways against different pathogens and its relation to hypersensitivities," bioRxiv, Jul. 2014, 006965, 17 pages.

* cited by examiner

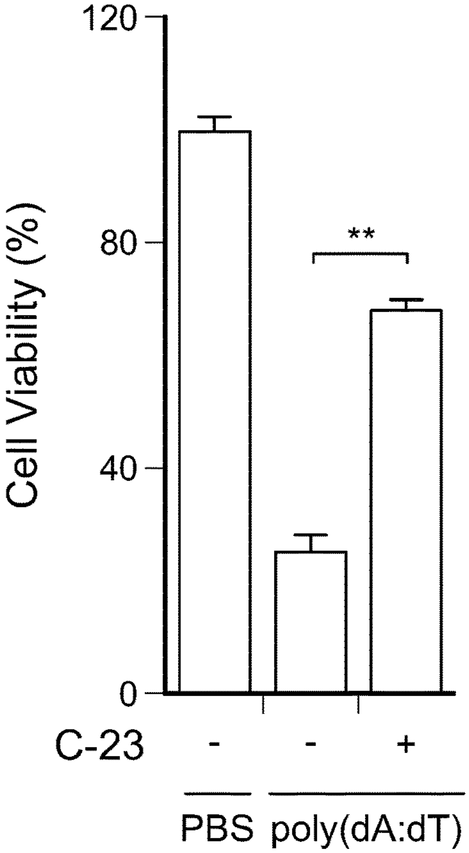
FIG. 10
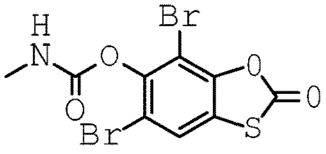
C-5
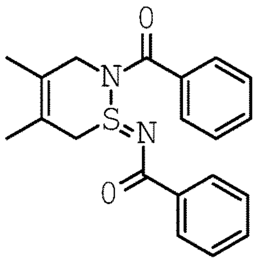
C-7
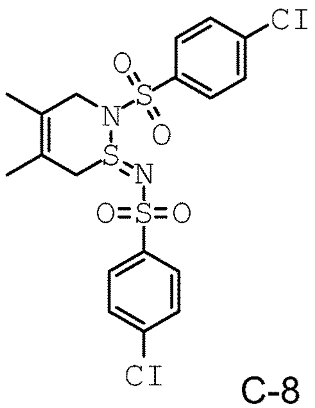
C-8
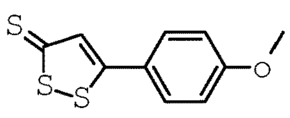
C-22
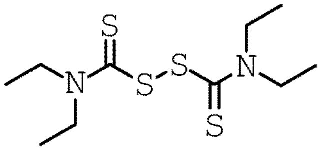
C-23
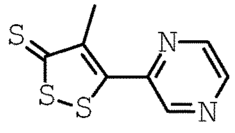
C-24
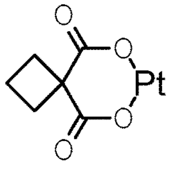
C-25
FIG. 11

```
                 .      .      .      .      .50     .      .      .      .      .100   .
GSDMA3    1 .MPVFEDVTRALVRELN.PRGDLTPLDSLIDFKHFRPFCLVLRKRKSTLFWGARYVRTDYTLLDLLEPGSSPSDLTDSGNFSFKNMLDVQVQGLVEVPKT..VKVKGTAGLSQS..STLEVQ
hGSDMA    1 .MTMFENVTRALARQLN.PRGDLTPLDSLIDFKRFHPFCLVLRKRKSTLFWGARYVRTDYTLLDVLEPGSSPSDPTDTGNFGFKNMLDTRVEGDVDVPKT..VKVKGTAGLSQN..STLEVQ
mGSDMD    1 MPSAFEKVVKNVIKEVSGSRGDLIPVDSLRNSTSFRPYCLLNRKFSSSRFWKPRYSCVNLSIKDILFPSAPEPEPECFGSFKVSDVVDGNIQGRVMLSGMGEGKISGGAAVSDSSSASMNVC
hGSDMD    1 MGSAFERVVRRVVQELD.HGGEFIPVTSLQSSTGFQPYCLVVRKPSSSWFWKPRYKCVNLSIKDILEPDAAEPDVQRGRSFHFYDAMDGQIQGSVELAAPGQAKIAGGAAVSDSSSTSMNVY
                .     .  .     .  Cys38.     .50     .      .      .      .      .100   .      .

                  .      .      .     .150    .      .      .      .      .200   .      .      .
GSDMA3  117 TLSVAPSALENLKKERKLS.ADHSFLNEMRYHEKNLYVVMEAVEAKQEVTVEQTG..NANAIFSLPSLALLG..LQGSLNNNKAVTIPKGCVLAYRVRLLRVFLFNLWDIPYICNDSMQTFP
hGSDMA  117 TLSVAPKALETLQ.ERKLA.ADHPFLKEMQDQGENLYVVMEVVETVQEVTLERAGKAE..ACFSLPFFAPLG..LQGSINHKEAVTIPKGCVLAFRVRQLMVKGKDEWDIPHICNDNMQTFP
mGSDMD  123 ILRVTQKTWETMQHERHLQQPENKILQQLRSRGDDLFVVTEVLQTKEEVQITEVHSQEGSGQFTLPGALCLKGEGKGHQSRKKMVTIPAGSILAFRVAQL..LIGSKWDILLVSDEKQRTFE
hGSDMD  122 SLSVDPNTWQTLLHERHLRQPEHKVLQQLRSRGDNVYVVTEVLQTQKEVEVTRTHKREGSGRFSLPGATCLQGEGQGHLSQKKTVTIPSGSTLAFRVAQL..VIDSDLDVLLFPDKKQRTFQ
                  .      .     .150    .      .      .      .Cys191  .200   .      .      .      .
```

FIG. 29

C-23
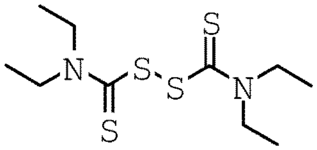
C-23A1
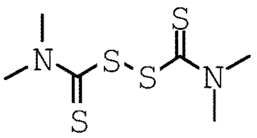
C-23A2
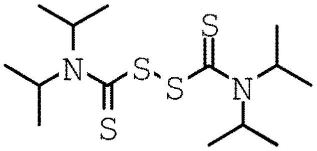
C-23A3
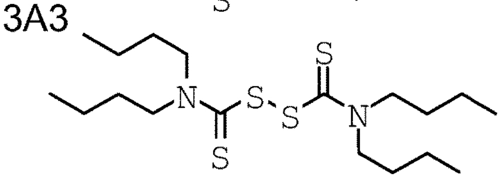
C-23A4
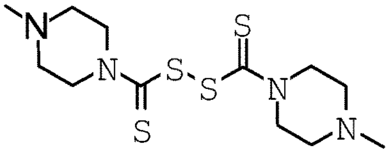
C-23A5
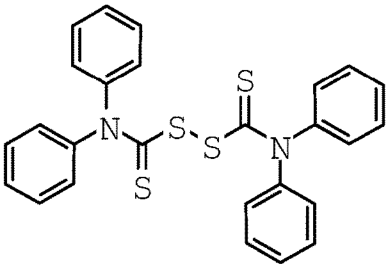
C-23A6
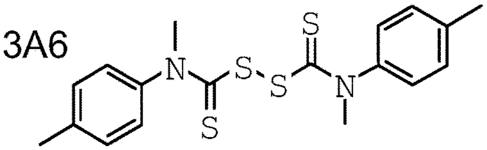
C-23A7
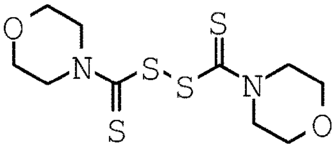
C-23A8
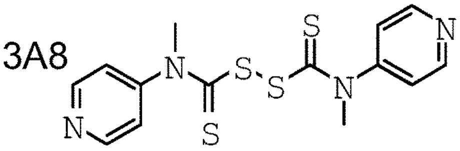
C-23A9
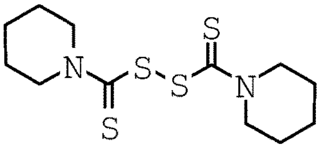
C-23A10
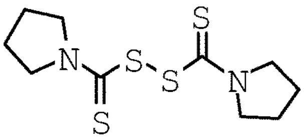
C-23A11
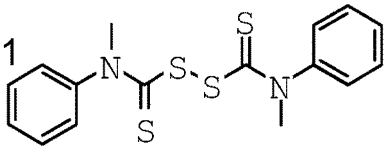
C-23A12
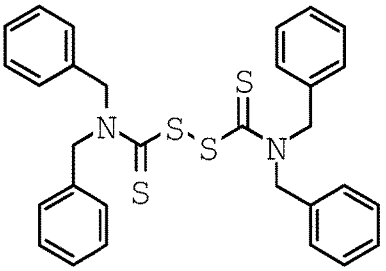
FIG. 39

```
                        .         .         .         .         .50
GSDMA3     1 .MPVFEDVTRALVRELN.PRGDLTPLDSLIDFKHFRPFCLVLRKRKSTLFWGARYVRTDYT
hGSDMA     1 .MTMFENVTRALARQLN.PRGDLTPLDSLIDFKRFHPFCLVLRKRKSTLFWGARYVRTDYT
mGSDMD     1 MPSAFEKVVKNVIKEVSGSRGDLIPVDSLRNSTSFRPYCLLNRKFSSSRFWKPRYSCVNLS
hGSDMD     1 MGSAFERVVRRVVQELD.HGGEFIPVTSLQSSTGFQPYCLVVRKPSSSWFWKPRYKCVNLS
                       .         .         .    Cys38.        .50       .

               .         .         .         .       .100      .
GSDMA3    60 LLDLLEPGSSPSDLTDSGNFSFKNMLDVQVQGLVEVPKT..VKVKGTAGLSQS..STLEVQ
hGSDMA    60 LLDVLEPGSSPSDPTDTGNFGFKNMLDTRVEGDVDVPKT..VKVKGTAGLSQN..STLEVQ
mGSDMD    62 IKDILFPSAPEPEPECFGSFKVSDVVDGNIQGRVMLSGMGEGKISGGAAVSDSSSASMNVC
hGSDMD    61 IKDILEPDAAEPDVQRGRSFHFYDAMDGQIQGSVELAAPGQAKIAGGAAVSDSSSTSMNVY
                       .         .         .        .100      .         .

                 .         .         .        .150      .         .
GSDMA3   117 TLSVAPSALENLKKERKLS.ADHSFLNEMRYHEKNLYVVMEAVEAKQEVTVEQTG..NANA
hGSDMA   117 TLSVAPKALETLQ.ERKLA.ADHPFLKEMQDQGENLYVVMEVVETVQEVTLERAGKAE..A
mGSDMD   123 ILRVTQKTWETMQHERHLQQPENKILQQLRSRGDDLFVVTEVLQTKEEVQITEVHSQEGSG
hGSDMD   122 SLSVDPNTWQTLLHERHLRQPEHKVLQQLRSRGDNVYVVTEVLQTQKEVEVTRTHKREGSG
                      .         .        .150       .         .         .

                  .         .         .200      .         .         .
GSDMA3   175 IFSLPSLALLG..LQGSLNNNKAVTIPKGCVLAYRVRLLRVFLFNLWDIPYICNDSMQTFP
hGSDMA   174 CFSLPFFAPLG..LQGSINHKEAVTIPKGCVLAFRVRQLMVKGKDEWDIPHICNDNMQTFP
mGSDMD   184 QFTLPGALCLKGEGKGHQSRKKMVTIPAGSILAFRVAQL..LIGSKWDILLVSDEKQRTFE
hGSDMD   183 RFSLPGATCLQGEGQGHLSQKKTVTIPSGSTLAFRVAQL..VIDSDLDVLLFPDKKQRTFQ
                      .Cys191   .200     .         .         .         .
```

FIG. 89

COMPOUNDS FOR INHIBITION OF INFLAMMATION

CLAIM OF PRIORITY

This application is a 371 National Stage Entry of PCT/US2019/039499, filed on Jun. 27, 2019, which claims priority to U.S. Provisional Patent Application Ser. No. 62/690,788, filed on Jun. 27, 2018, the entire contents of which are hereby incorporated by reference.

STATEMENT OF FEDERALLY SPONSORED RESEARCH

This invention was made with government support under Grant Number AI139914, awarded by the National Institutes of Health. The Government has certain rights in the invention.

TECHNICAL FIELD

This invention relates to chemical compounds, in particular to compounds that inhibit inflammation and are useful in treating conditions associated with inflammation.

BACKGROUND

Inflammasomes are multi-protein signaling scaffolds that assemble in response to invasive pathogens and sterile danger signals to activate inflammatory caspases (1/4/5/11), which trigger inflammatory death (pyroptosis) and processing and release of pro-inflammatory cytokines. Inflammasome activation contributes to many human diseases, including inflammatory bowel disease, gout, type II diabetes, cardiovascular disease, Alzheimer's disease, and sepsis, the often fatal response to systemic infection.

SUMMARY

In a first general aspect, the present disclosure provides a method of inhibiting gasdermin pore formation in a cell; and/or
inhibiting inflammasome-mediated death of a cell (pyroptosis); and/or
inhibiting cytokine secretion from a cell; and/or
inhibiting an inflammatory caspase in a cell; and/or
covalently reacting with a cysteine of a gasdermin protein in a cell; and/or
covalently reacting with a cysteine of an inflammatory signaling molecule selected from: a sensor, an adaptor, and a transcription factor, or a regulator thereof;

the method comprising contacting the cell with an effective amount of any one of the compounds as described herein, or a pharmaceutically acceptable salt thereof.

In a second general aspect, the present disclosure provides a method of treating or preventing a disease or condition in which inflammasome activation and/or a gasdermin inflammatory cell death is implicated in pathogenesis, the method comprises administering to a subject in need thereof a therapeutically effective amount of any one of the compounds as described herein, or a pharmaceutically acceptable salt thereof.

In a third general aspect, the present disclosure provides a method of identifying a compound that:

inhibits a gasdermin pore formation in a cell; and/or
inhibits inflammasome-mediated death of a cell (pyroptosis); and/or inhibits cytokine secretion from a cell; and/or
inhibits an inflammatory caspase in a cell; and/or
covalently reacts with a cysteine of a gasdermin protein in a cell; and/or
covalently reacts with a cysteine of an inflammatory signaling molecule selected from: a sensor, an adaptor, and a transcription factor, or a regulator thereof;

the method comprising:

a) providing a sample comprising a liposome comprising a metal cation capable of forming a complex with a chelating ligand, the chelating ligand, a test compound, and a gasdermin protein, or a fragment thereof;
b) contacting the gasdermin protein in the sample with a protease enzyme; and
c) determining whether the test compound inhibits leakage of the metal cation from the liposome, wherein said inhibition of the leakage of the metal cation from the liposome is an indication that the test compound:

inhibits a gasdermin pore formation in a cell; and/or
inhibits inflammasome-mediated death of a cell (pyroptosis); and/or
inhibits cytokine secretion from a cell; and/or
inhibits an inflammatory caspase in a cell; and/or
covalently reacts with a cysteine of a gasdermin protein in a cell; and/or
covalently reacts with a cysteine of an inflammatory signaling molecule selected from: a sensor, an adaptor, and a transcription factor, or a regulator thereof.

In a fourth general aspect, the present disclosure provides a pharmaceutical composition comprising any one of the compounds described herein, or a pharmaceutically acceptable salt thereof, and a pharmaceutically acceptable carrier.

Certain implementations of the first, the second, the third, and the fourth general aspects are described herein.

In some embodiments, the present disclosure provides a composition comprising any one of the compounds described herein, or a pharmaceutically acceptable salt thereof, for treating or preventing any one of the diseases or conditions described herein.

In some embodiments, the present disclosure provides any one of the compounds described herein, or a pharmaceutically acceptable salt thereof, for use as a medicament for treating or preventing any one of the diseases or conditions described herein.

In some embodiments, the present disclosure provides a use of any one of the compounds described herein, or a pharmaceutically acceptable salt thereof, in the manufacture of a medicament for the treatment or prevention of any one of the diseases or conditions described herein.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 10 contains a bar graph showing cell viability after pretreatment with C-23 before transfection with PBS or poly(dA:dT).

FIG. 11 contain chemical structures of compounds C-5, C-7, C-8, C-22, C-23, C-24, and C-25.

FIG. 29 contains sequence alignment of GSDMA3, hGSDMA, mGSDMD and hGSDMD showing Cys residues.

FIG. 39 contains chemical structures of test compounds presented in Table 2.

FIG. 89 contains an image showing sequence alignment of GSDMA3, hGSDMA, mGSDMD and hGSDMD showing Cys residues.

DETAILED DESCRIPTION

Figure 1:
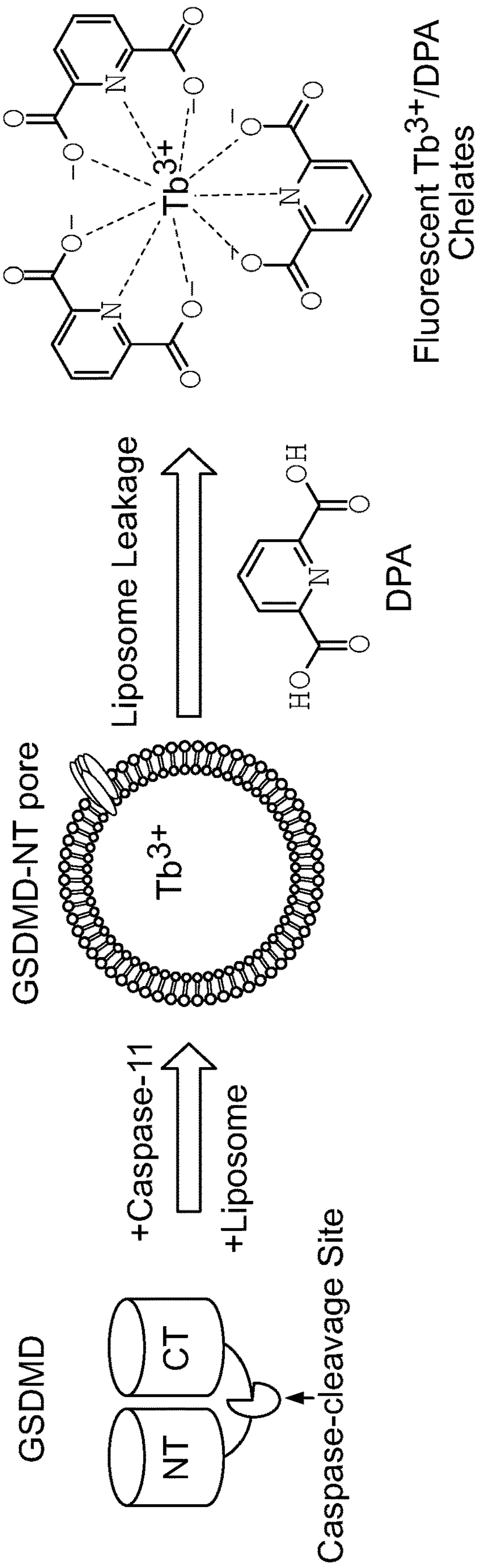
FIG. 1 contains a pictorial representation of the terbium ($Tb^{3+}$)/dipicolinic acid (DPA) fluorescence liposome leakage assay.

As discussed more fully below, the pore-forming protein gasdermin (such as gasdermin D) is the final pyroptosis executioner downstream of inflammasome activation. The compounds of the present application potently inhibit gasdermin pore formation and subsequent secretion of inflammatory mediators such as IL-1β. As such, the compounds of the present application are useful, for example, in treating diseases and conditions mediated by inflammation such as sepsis. Pharmaceutical compositions containing compounds of the present disclosure, as well as various methods using and making these compounds are described below.

Therapeutic Compounds

In one general aspect, the present disclosure provides a compound of Formula (I):

(I)

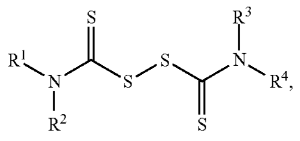

or a pharmaceutically acceptable salt thereof, wherein:

$R^1$, $R^2$, $R^3$, and $R^4$ are each independently selected from H, $C_{1-6}$ alkyl, $C_{1-6}$ haloalkyl, $C_{2-6}$ alkenyl, $C_{2-6}$ alkynyl, $Cy^1$, $C(O)R^{b1}$, $C(O)NR^{c1}R^{d1}$, $C(O)OR^{a1}$, $S(O)_2R^{b1}$, and $S(O)_2NR^{c1}R^{d1}$; wherein said $C_{1-6}$ alkyl, $C_{2-6}$ alkenyl, and $C_{2-6}$ alkynyl are each optionally substituted with 1, 2 or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

or $R^1$ and $R^2$ together with the N atom to which they are attached form a 4-12 membered heterocycloalkyl, which is optionally substituted with 1, 2, 3, 4, or 5 substituents independently selected from $R^{Cy2}$;

or $R^3$ and $R^4$ together with the N atom to which they are attached form a 4-12 membered heterocycloalkyl, which is optionally substituted with 1, 2, 3, 4, or 5 substituents independently selected from $R^{Cy3}$;

each $Cy^1$ is independently selected from $C_{6-10}$ aryl, $C_{3-10}$ cycloalkyl, 5-10 membered heteroaryl, and 4-12 membered heterocycloalkyl, each of which is optionally substituted with 1, 2, 3, 4, or 5 substituents independently selected from $R^{Cy1}$;

each $R^{Cy1}$, $R^{Cy2}$, and $R^{Cy3}$ is independently selected from $C_{1-6}$ alkyl, $C_{2-6}$ alkenyl, $C_{2-6}$ alkynyl, $C_{1-6}$ haloalkyl, halo, CN, $NO_2$, $OR^{a2}$, $C(O)R^{b2}$, $C(O)NR^{c2}R^{d2}$, C(O)

$OR^{a2}$, $NR^{c2}R^{d2}$, $NR^{c2}C(O)R^{b2}$, $NR^{c2}C(O)OR^{a2}$, $NR^{c2}C(O)NR^{c2}R^{d2}$, $S(O)_2R^{b2}$ and $S(O)_2NR^{c2}R^{d2}$;

$R^{a1}$, $R^{a2}$, $R^{c1}$, $R^{c2}$, $R^{d1}$, and $R^{d2}$ are each independently selected from H, $C_{1-6}$ alkyl, $C_{2-6}$ alkenyl, $C_{2-6}$ alkynyl, $C_{1-4}$ haloalkyl, $Cy^1$, $C(O)R^{b3}$, $C(O)NR^{c3}R^{d3}$, $C(O)OR^{a3}$, $S(O)_2R^{b3}$, and $S(O)_2NR^{c3}R^{d3}$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$ and $S(O)_2NR^{c3}R^{d3}$;

$R^{b1}$ and $R^{b2}$ are each independently selected from $C_{1-6}$ alkyl, $C_{2-6}$ alkenyl, $C_{2-6}$ alkynyl, $C_{1-4}$ haloalkyl and $Cy^1$; wherein said $C_{1-6}$ alkyl, $C_{2-6}$ alkenyl, and $C_{2-6}$ alkynyl are each optionally substituted with 1, 2, 3, 4, or 5 substituents independently selected from $Cy^1$, halo, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)_2R^{b3}$, $NR^{c3}S(O)_2NR^{c3}R^{d3}$, $S(O)_2R^{b3}$ and $S(O)_2NR^{c3}R^{d3}$;

$R^{a3}$, $R^{c3}$, and $R^{d3}$ are each independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, $C(O)R^{b4}$, $C(O)NR^{C4}R^{d4}$, $C(O)OR^{a4}$, $NR^{C4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from oxo, $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

each $R^{b3}$ is independently selected from $C_{1-6}$ alkyl, $C_{2-6}$ alkenyl, $C_{2-6}$ alkynyl, $C_{1-4}$ haloalkyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $SR^{a4}$, $C(O)R^{b4}$, $C(O)NR^{c4}R^{d4}$, $C(O)OR^{a4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)_2R^{b4}$, $NR^{c4}S(O)_2NR^{c4}R^{d4}$, $S(O)_2R^{b4}$, and $S(O)_2NR^{c4}R^{d4}$;

$R^{a4}$, $R^{c4}$, and $R^{d4}$ are each independently selected from H, $C_{1-6}$ alkyl, $C_{1-4}$ haloalkyl, $C_{1-4}$ hydroxyalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene are each optionally substituted with 1, 2, 3, 4, or 5 substituents independently selected from $R^g$;

each $R^{b4}$ is independently selected from $C_{1-6}$ alkyl, $C_{1-4}$ haloalkyl, $C_{1-4}$ hydroxyalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene and $R^g$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, and (4-12 membered heterocycloalkyl)-$C_{1-4}$ alkylene is optionally substituted with 1, 2, 3, 4, or 5 substituents independently selected from $R^g$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkylene, HO—$C_{1-3}$ alkylene, $C_{6-10}$ aryl, $C_{6-10}$ aryloxy, $C_{3-10}$ cycloalkyl, 5-10 membered heteroaryl, 4-12 membered heterocycloalkyl, $C_{6-10}$ aryl-$C_{1-4}$ alkylene, $C_{3-10}$ cycloalkyl-$C_{1-4}$ alkylene, (5-10 membered heteroaryl)-$C_{1-4}$ alkylene, (4-12 membered heterocycloalkyl)-$C_{1-4}$ alkylene, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is selected from H, $C_{1-6}$ alkyl, $C_{1-6}$ haloalkyl, $C_{2-6}$ alkenyl, $C_{2-6}$ alkynyl, and $Cy^1$; wherein said $C_{1-6}$ alkyl, $C_{2-6}$ alkenyl, and $C_{2-6}$ alkynyl are each optionally substituted with 1, 2 or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$.

In some embodiments, $R^1$ is selected from H, $C_{1-6}$ alkyl, $C_{1-6}$ haloalkyl, and $Cy^1$; wherein said $C_{1-6}$ alkyl is optionally substituted with 1, 2 or 3 substituents independently selected from $Cy^1$, halo, CN, $NO_2$, $OR^{a1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, and $NR^{c1}S(O)_2R^{b1}$.

In some embodiments, $R^1$ is $C_{1-6}$ alkyl optionally substituted with $Cy^1$. In some aspects of these embodiments, $R^1$ is selected from methyl, ethyl, propyl, isopropyl, n-butyl, and t-butyl, each of which is optionally substituted with $Cy^1$. In other aspects of these embodiments, $R^1$ is methyl substituted with $Cy^1$. In some embodiments, $R^1$ is $Cy^1$. In some embodiments, $R^1$ is selected from $Cy^1$ and $C_{1-6}$ alkyl optionally substituted with $Cy^1$.

In some embodiments, $R^2$ is selected from H, $C_{1-6}$ alkyl, $C_{1-6}$ haloalkyl, $C_{2-6}$ alkenyl, $C_{2-6}$ alkynyl, and $Cy^1$; wherein said $C_{1-6}$ alkyl, $C_{2-6}$ alkenyl, and $C_{2-6}$ alkynyl are each optionally substituted with 1, 2 or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$.

In some embodiments, $R^2$ is selected from H, $C_{1-6}$ alkyl, $C_{1-6}$ haloalkyl, and $Cy^1$; wherein said $C_{1-6}$ alkyl is optionally substituted with 1, 2 or 3 substituents independently selected from $Cy^1$, halo, CN, $NO_2$, $OR^{a1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, and $NR^{c1}S(O)_2R^{b1}$.

In some embodiments, $R^2$ is $C_{1-6}$ alkyl optionally substituted with $Cy^1$. In some aspects of these embodiments, $R^2$ is selected from methyl, ethyl, propyl, isopropyl, n-butyl, and t-butyl, each of which is optionally substituted with $Cy^1$. In other aspects of these embodiments, $R^2$ is methyl substituted with $Cy^1$. In some embodiments, $R^2$ is $Cy^1$. In some embodiments, $R^2$ is selected from $Cy^1$ and $C_{1-6}$ alkyl optionally substituted with $Cy^1$.

In some embodiments, $R^3$ is selected from H, $C_{1-6}$ alkyl, $C_{1-6}$ haloalkyl, $C_{2-6}$ alkenyl, $C_{2-6}$ alkynyl, and $Cy^1$; wherein said $C_{1-6}$ alkyl, $C_{2-6}$ alkenyl, and $C_{2-6}$ alkynyl are each optionally substituted with 1, 2 or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$.

In some embodiments, $R^3$ is selected from H, $C_{1-6}$ alkyl, $C_{1-6}$ haloalkyl, and $Cy^1$; wherein said $C_{1-6}$ alkyl is optionally substituted with 1, 2 or 3 substituents independently selected from $Cy^1$, halo, CN, $NO_2$, $OR^{a1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, and $NR^{c1}S(O)_2R^{b1}$.

In some embodiments, $R^3$ is $C_{1-6}$ alkyl optionally substituted with $Cy^1$. In some aspects of these embodiments, $R^3$ is selected from methyl, ethyl, propyl, isopropyl, n-butyl, and t-butyl, each of which is optionally substituted with $Cy^1$. In other aspects of these embodiments, $R^3$ is methyl substituted with $Cy^1$. In some embodiments, $R^3$ is $Cy^1$. In some embodiments, $R^3$ is selected from $Cy^1$ and $C_{1-6}$ alkyl optionally substituted with $Cy^1$.

In some embodiments, $R^4$ is selected from H, $C_{1-6}$ alkyl, $C_{1-6}$ haloalkyl, $C_{2-6}$ alkenyl, $C_{2-6}$ alkynyl, and $Cy^1$; wherein said $C_{1-6}$ alkyl, $C_{2-6}$ alkenyl, and $C_{2-6}$ alkynyl are each optionally substituted with 1, 2 or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$.

In some embodiments, $R^4$ is selected from H, $C_{1-6}$ alkyl, $C_{1-6}$ haloalkyl, and $Cy^1$; wherein said $C_{1-6}$ alkyl is optionally substituted with 1, 2 or 3 substituents independently selected from $Cy^1$, halo, CN, $NO_2$, $OR^{a1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, and $NR^{c1}S(O)_2R^{b1}$.

In some embodiments, $R^4$ is $C_{1-6}$ alkyl optionally substituted with $Cy^1$. In some aspects of these embodiments, $R^4$ is selected from methyl, ethyl, propyl, isopropyl, n-butyl, and t-butyl, each of which is optionally substituted with $Cy^1$. In other aspects of these embodiments, $R^4$ is methyl substituted with $Cy^1$. In some embodiments, $R^4$ is $Cy^1$. In some embodiments, $R^4$ is selected from $Cy^1$ and $C_{1-6}$ alkyl optionally substituted with $Cy^1$.

In some embodiments, $R^1$ and $R^2$ are each $C_{1-6}$ alkyl optionally substituted with $Cy^1$. In some embodiments, $R^1$ and $R^2$ are each $Cy^1$. In some embodiments, $R^1$ is $C_{1-6}$ alkyl optionally substituted with $Cy^1$, and $R^2$ is $Cy^1$. In some embodiments, $R^1$ is $Cy^1$; and $R^2$ is $C_{1-6}$ alkyl optionally substituted with $Cy^1$.

In some embodiments, $R^3$ and $R^4$ are each $C_{1-6}$ alkyl optionally substituted with $Cy^1$. In some embodiments, $R^3$ and $R^4$ are each $Cy^1$. In some embodiments, $R^3$ is $C_{1-6}$ alkyl optionally substituted with $Cy^1$, and $R^4$ is $Cy^1$. In some embodiments, $R^3$ is $Cy^1$; and $R^4$ is $C_{1-6}$ alkyl optionally substituted with $Cy^1$.

In some embodiments, $R^1$ and $R^2$ together with the N atom to which they are attached form a 4-12 membered heterocycloalkyl, which is optionally substituted with 1, 2, or 3 substituents independently selected from $R^{Cy2}$. In some aspects of the foregoing embodiments, 4-12 membered heterocycloalkyl is selected from any one of the following groups:

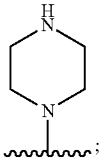;
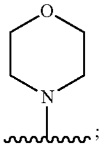;
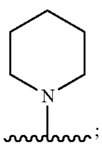; and
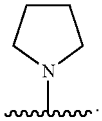.

In some embodiments, $R^3$ and $R^4$ together with the N atom to which they are attached form a 4-12 membered heterocycloalkyl, which is optionally substituted with 1, 2, or 3 substituents independently selected from $R^{Cy3}$. In some aspects of the foregoing embodiments, 4-12 membered heterocycloalkyl is selected from any one of the following groups:

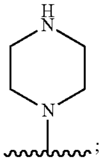;
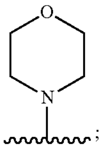;
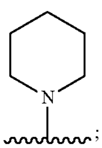; and
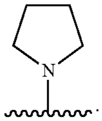.

In some embodiments, $Cy^1$ is $C_{6-10}$ aryl, optionally substituted with 1, 2, or 3 substituents independently selected from $R^{Cy1}$. In some aspects of these embodiments, $C_{6-10}$ aryl is phenyl or naphthyl.

In some embodiments, each $Cy^1$ is independently selected from $C_{6-10}$ aryl and 5-10 membered heteroaryl, each of which is optionally substituted with 1, 2, or 3 substituents independently selected from $R^{Cy1}$.

In some embodiments, $Cy^1$ is $C_{3-10}$ cycloalkyl, optionally substituted with 1, 2, or 3 substituents independently selected from $R^{Cy1}$. In some aspects of these embodiments, $C_{3-10}$ cycloalkyl is selected from cyclopropyl, cyclobutyl, cyclopentyl, and cyclohexyl.

In some embodiments, $Cy^1$ is 5-10 membered heteroaryl, optionally substituted with 1, 2, or 3 substituents independently selected from $R^{Cy1}$. In some aspects of these embodiments, 5-10 membered heteroaryl is selected from thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, 1,3,4-oxadiazolyl, pyridyl, pyrazinyl, pyrimidinyl, triazinyl and pyridazinyl. In other aspects of these embodiments, 5-10 membered heteroaryl is selected from pyridin-2-yl, pyridin-3-yl, and pyridin-4-yl.

In some embodiments, $Cy^1$ is 4-12 membered heterocycloalkyl, optionally substituted with 1, 2, or 3 substituents independently selected from $R^{Cy1}$. In some aspects of these embodiments, the 4-12 membered heterocycloalkyl is selected from tetrahydropuranyl, oxetanyl, azetidinyl, morpholinyl, thiomorpholinyl, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, and benzazapenyl.

In some embodiments, each $R^{Cy1}$ is independently selected from $C_{1-6}$ alkyl, $C_{1-6}$ haloalkyl, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, and $NR^{c2}C(O)OR^{a2}$. In some embodiments, each $R^{Cy1}$ is $C_{1-6}$ alkyl.

In some embodiments, each $R^{Cy2}$ is independently selected from $C_{1-6}$ alkyl, $C_{1-6}$ haloalkyl, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, and $NR^{c2}C(O)OR^{a2}$. In some embodiments, each $R^{Cy2}$ is $C_{1-6}$ alkyl.

In some embodiments, each $R^{Cy3}$ is independently selected from $C_{1-6}$ alkyl, $C_{1-6}$ haloalkyl, halo, CN, $NO_2$, $OR^{a2}$, $C(O)R^{b2}$, $C(O)NR^{c2}R^{d2}$, $C(O)OR^{a2}$, $NR^{c2}R^{d2}$, $NR^{c2}C(O)R^{b2}$, and $NR^{c2}C(O)OR^{a2}$. In some embodiments, each $R^{Cy3}$ is $C_{1-6}$ alkyl.

In some embodiments, $R^{a1}$, $R^{a2}$, $R^{c1}$, $R^{c2}$, $R^{d1}$, and $R^{d2}$ are each independently selected from H, $C_{1-6}$ alkyl, $Cy^1$, $C(O)R^{b3}$, $C(O)NR^{c3}R^{d3}$, $C(O)OR^{a3}$, $S(O)_2R^{b3}$, $S(O)_2NR^{c3}R^{d3}$; wherein said $C_{1-6}$ alkyl is optionally substituted with 1, 2, or 3 substituents independently selected from $Cy^1$, halo, CN, $NO_2$, $OR^{a3}$, $NR^{c3}R^{d3}$, $NR^{c3}C(O)R^{b3}$, $NR^{c3}C(O)OR^{a3}$, and $NR^{c3}S(O)_2R^{b3}$.

In some embodiments, $R^{b1}$ and $R^{b2}$ are each independently selected from $C_{1-6}$ alkyl and $Cy^1$, wherein said $C_{1-6}$ alkyl is optionally substituted with 1, 2, or 3 substituents independently selected from halo, $Cy^1$, CN, $NO_2$, $OR^{a3}$, $NR^{c3}R^{d3}$, $NR^{c3}C(O)R^{b3}$, $NR^{c3}C(O)OR^{a3}$, and $NR^{c3}S(O)_2R^{b3}$.

In some embodiments, $R^{a3}$, $R^{c3}$, and $R^{d3}$ are each independently selected from H, $C_{1-6}$ alkyl, $C_{1-4}$haloalkyl, $C_{6-10}$ aryl, $C_{3-10}$ cycloalkyl, 5-10 membered heteroaryl, 4-12 membered heterocycloalkyl, each of which is optionally substituted with 1, 2, or 3 substituents independently selected from $C_{1-4}$ haloalkyl, $C_{1-4}$ hydroxyalkyl, $C_{1-6}$ cyanoalkyl, halo, CN, $NO_2$, $OR^{a4}$, $NR^{c4}R^{d4}$, $NR^{c4}C(O)R^{b4}$, $NR^{c4}C(O)OR^{a4}$, and $NR^{c4}S(O)_2R^{b4}$.

In some embodiments, each $R^{b3}$ is independently selected from $C_{1-6}$ alkyl, $C_{1-4}$ haloalkyl, $C_{6-10}$ aryl, $C_{3-10}$ cycloalkyl, 5-10 membered heteroaryl, 4-12 membered heterocycloalkyl, each of which is optionally substituted with 1, 2, or 3 substituents independently selected from $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $NR^{c4}R^{d4}$, $NR^{c4}C(O)R^{b4}$, $NR^{c4}C(O)OR^{a4}$, and $NR^{c4}S(O)_2R^{b4}$.

In some embodiments, $R^{a4}$, $R^{c4}$, and $R^{d4}$ are each independently selected from H, $C_{1-6}$ alkyl, $C_{1-4}$haloalkyl, $C_{1-4}$ hydroxyalkyl, $C_{1-4}$ cyanoalkyl, $C_{6-10}$ aryl, $C_{3-10}$ cycloalkyl, 5-10 membered heteroaryl, 4-12 membered heterocycloalkyl, each of which is optionally substituted with 1, 2, or 3 substituents independently selected from $R^9$.

In some embodiments, each $R^{b4}$ is independently selected from $C_{1-6}$ alkyl, $C_{1-4}$ haloalkyl, $C_{1-4}$ hydroxyalkyl, $C_{1-4}$ cyanoalkyl, $C_{6-10}$ aryl, $C_{3-10}$ cycloalkyl, 5-10 membered heteroaryl, 4-12 membered heterocycloalkyl, each of which is optionally substituted with 1, 2, or 3 substituents independently selected from $R^9$.

In some embodiments, each $R^9$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, cyano-$C_{1-3}$ alkylene, and HO—$C_{1-3}$ alkylene.

In some embodiments:

each $R^1$, $R^2$, $R^3$, and $R^4$ is independently selected from H, $C_{1-6}$ alkyl, $C_{1-6}$ haloalkyl, $C_{2-6}$ alkenyl, $C_{2-6}$ alkynyl, and $Cy^1$; wherein said $C_{1-6}$ alkyl, $C_{2-6}$ alkenyl, and $C_{2-6}$ alkynyl are each optionally substituted with 1, 2 or 3 substituents independently selected from $Cy^1$, halo, CN, $NO_2$, $OR^{a1}$, $SR^{a1}$, $C(O)R^{b1}$, $C(O)NR^{c1}R^{d1}$, $C(O)OR^{a1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)_2R^{b1}$, $NR^{c1}S(O)_2NR^{c1}R^{d1}$, $S(O)_2R^{b1}$ and $S(O)_2NR^{c1}R^{d1}$;

or $R^1$ and $R^2$ together with the N atom to which they are attached form a 4-12 membered heterocycloalkyl, which is optionally substituted with 1, 2, or 3 substituents independently selected from $R^{Cy2}$;

or $R^3$ and $R^4$ together with the N atom to which they are attached form a 4-12 membered heterocycloalkyl, which is optionally substituted with 1, 2, or 3 substituents independently selected from $R^{Cy3}$;

each $Cy^1$ is independently selected from $C_{6-10}$ aryl and 5-10 membered heteroaryl, each of which is optionally substituted with 1, 2, or 3 substituents independently selected from $R^{Cy1}$;

each $R^{Cy1}$, $R^{Cy2}$, and $R^{Cy3}$ is independently selected from $C_{1-6}$ alkyl, $C_{1-6}$ haloalkyl, halo, CN, $NO_2$, $OR^{a2}$, $C(O)R^{b2}$, $C(O)NR^{c2}R^2$, $C(O)OR^{a2}$, $NR^{c2}R^{d2}$, $NR^{c2}C(O)R^{b2}$, and $NR^{c2}C(O)OR^{a2}$;

$R^{a1}$, $R^{a2}$, $R^{c1}$, $R^{c2}$, $R^{d1}$, and $R^{d2}$ are each independently selected from H, $C_{1-6}$ alkyl, $Cy^1$, $C(O)R^{b3}$, $C(O)NR^{c3}R^{d3}$, $C(O)OR^{a3}$, $S(O)_2R^{b3}$, and $S(O)_2NR^{c3}R^{d3}$; wherein said $C_{1-6}$ alkyl is optionally substituted with 1, 2, or 3 substituents independently selected from $Cy^1$, halo, CN, $NO_2$, $OR^{a3}$, $NR^{c3}R^{d3}$, $NR^{c3}C(O)R^{b3}$, $NR^{c3}C(O)OR^{a3}$, and $NR^{c3}S(O)_2R^{b3}$;

$R^{b1}$ and $R^{b2}$ are each independently selected from $C_{1-6}$ alkyl and $Cy^1$, wherein said $C_{1-6}$ alkyl is optionally substituted with 1, 2, or 3 substituents independently selected from halo, $Cy^1$, CN, $NO_2$, $OR^{a3}$, $NR^{c3}R^{d3}$, $NR^{c3}C(O)R^{b3}$, $NR^{c3}C(O)OR^{a3}$, and $NR^{c3}S(O)_2R^{b3}$;

$R^{a3}$, $R^{c3}$, and $R^{d3}$ are each independently selected from H, $C_{1-6}$ alkyl, $C_{1-4}$ haloalkyl, $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $C_{1-4}$haloalkyl, $C_{1-4}$ hydroxyalkyl, $C_{1-6}$ cyanoalkyl, halo, CN, $NO_2$, $OR^{a4}$, $NR^{c4}R^{d4}$, $NR^{c4}C(O)R^{b4}$, $NR^{c4}C(O)OR^{a4}$, and $NR^{c4}S(O)_2R^{b4}$;

each $R^{b3}$ is independently selected from $C_{1-6}$ alkyl, $C_{1-4}$ haloalkyl, $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $C_{1-6}$ alkyl, $C_{1-4}$ haloalkyl, $C_{1-4}$ hydroxyalkyl, $C_{1-6}$ cyanoalkyl, halo, CN, $NO_2$, $OR^{a4}$, $NR^{c4}R^{d4}$, $NR^{c4}C(O)R^{b4}$, $NR^{c4}C(O)OR^{a4}$, and $NR^{c4}S(O)_2R^{b4}$; $R^{a4}$, $R^{c4}$, and $R^{d4}$ are each independently selected from H, $C_{1-6}$ alkyl, $C_{1-4}$ haloalkyl, $C_{1-4}$ hydroxyalkyl, $C_{1-4}$ cyanoalkyl, $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^g$;

each $R^{b4}$ is independently selected from $C_{1-6}$ alkyl, $C_{1-4}$ haloalkyl, $C_{1-4}$ hydroxyalkyl, $C_{1-4}$ cyanoalkyl, $C_{6-10}$ aryl, $C_{3-10}$ cycloalkyl, 5-10 membered heteroaryl, and 4-12 membered heterocycloalkyl, each of which is optionally substituted with 1, 2, or 3 substituents independently selected from $R^g$; and each $R^g$ is independently selected from OH, $NO_2$, CN, halo, $C_{1-6}$ alkyl, $C_{1-4}$ haloalkyl, $C_{1-6}$ alkoxy, $C_{1-6}$ haloalkoxy, cyano-$C_{1-3}$ alkylene, and HO—$C_{1-3}$ alkylene.

In some aspects of the foregoing embodiments:

$R^1$, $R^2$, $R^3$, and $R^4$ are each independently selected from $Cy^1$ and $C_{1-6}$ alkyl optionally substituted with $Cy^1$.

In some embodiments, the compound of Formula (I) is selected from any one of compounds listed in Table A below:

TABLE A

| | |
|---|---|
| C-23 | 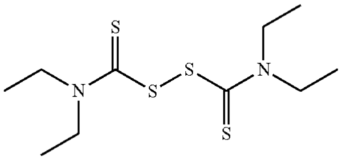 [SMILES: CCN(CC)C(=S)SSC(=S)N(CC)CC] |
| C-23A1 | 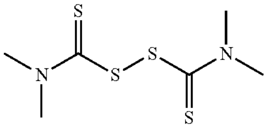 |
| C-23A2 | 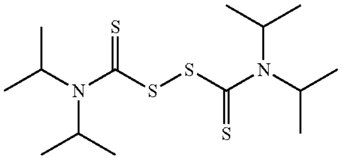 [SMILES: CC(C)N(C(=S)SSC(=S)N(C(C)C)C(C)C)C(C)C] |
| C-23A3 | 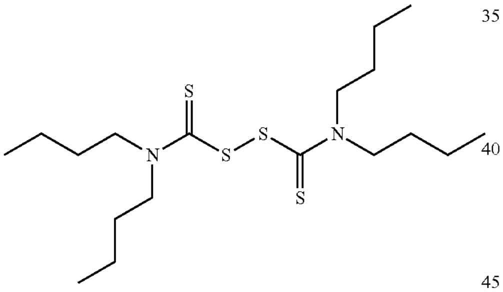 |
| C-23A4 | 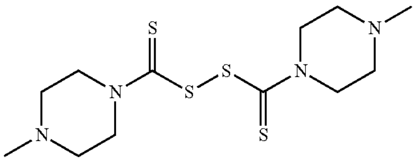 |
| C-23A5 | 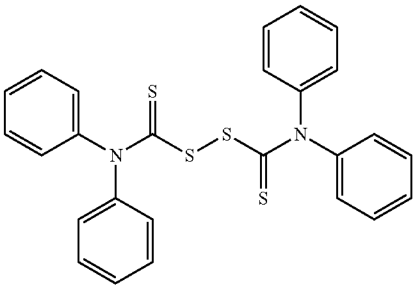 [SMILES: S=C(SSC(=S)N(c1ccccc1)c1ccccc1)N(c1ccccc1)c1ccccc1] |

TABLE A-continued

| | |
|---|---|
| C-23A6 | 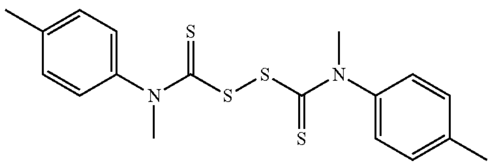 |
| C-23A7 | 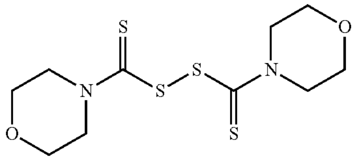 [SMILES: S=C(SSC(=S)N1CCOCC1)N1CCOCC1] |
| C-23A8 | 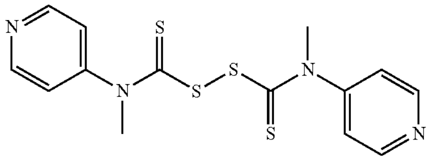 [SMILES: CN(C(=S)SSC(=S)N(C)c1ccncc1)c1ccncc1] |
| C-23A9 | 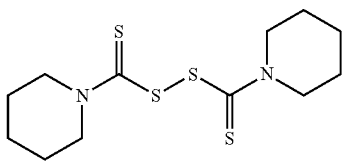 [SMILES: S=C(SSC(=S)N1CCCCC1)N1CCCCC1] |
| C-23A10 | 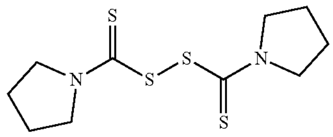 [SMILES: S=C(SSC(=S)N1CCCC1)N1CCCC1] |
| C-23A11 | 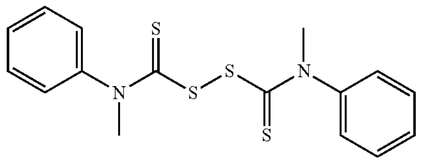 [SMILES: CN(C(=S)SSC(=S)N(C)c1ccccc1)c1ccccc1] |
| C-23A12 | 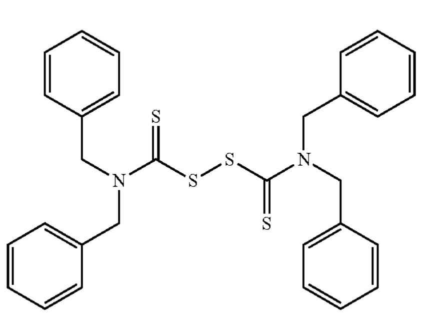 [SMILES: S=C(SSC(=S)N(Cc1ccccc1)Cc1ccccc1)N(Cc1ccccc1)Cc1ccccc1] |

or a pharmaceutically acceptable salt thereof.

In some embodiments, the compound of Formula (I) is not any one of the compounds listed in Table (A).

In some embodiments, the present application provides any one of the following compounds:

C-5
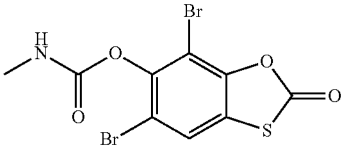 [SMILES: CNC(=O)Oc1c(Br)cc2sc(=O)oc2c1Br]
C-7
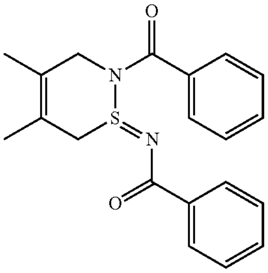 [SMILES: CC1=C(C)C/S(=N\C(=O)c2ccccc2)N(C(=O)c2ccccc2)C1]
C-8
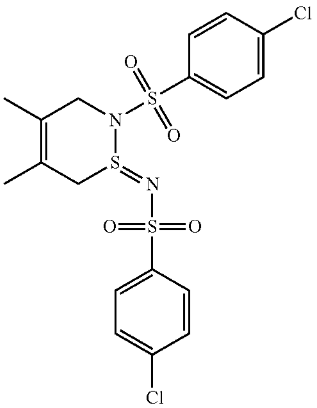 [SMILES: CC1=C(C)C/S(=N\S(=O)(=O)c2ccc(Cl)cc2)N(S(=O)(=O)c2ccc(Cl)cc2)C1]
C-22
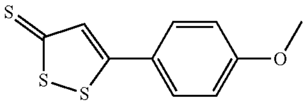
C-24
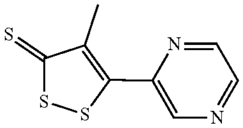
C-25
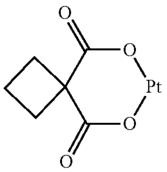
Bay 11-7082
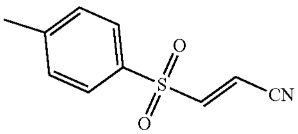
ASN-08966899
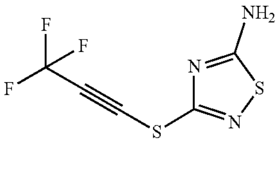 [SMILES: Nc1nc(SC#CC(F)(F)F)ns1]

-continued

LDC7559

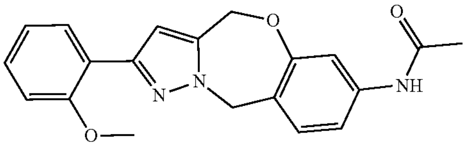 [SMILES: COc1ccccc1-c1cc2n(n1)Cc1ccc(NC(C)=O)cc1OC2]

ibrutinib

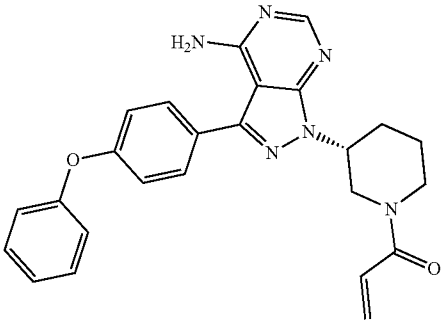 [SMILES: C=CC(=O)N1CCC[C@@H](n2nc(-c3ccc(Oc4ccccc4)cc3)c3c(N)ncnc32)C1]

Afatinib

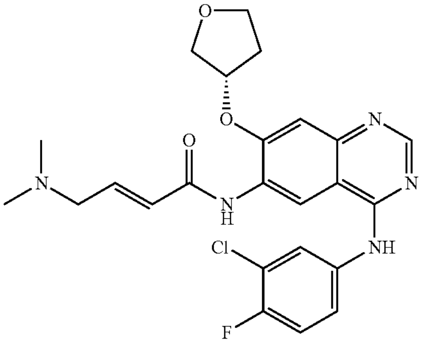 [SMILES: CN(C)C/C=C/C(=O)Nc1cc2c(Nc3ccc(F)c(Cl)c3)ncnc2cc1O[C@H]1CCOC1]

Dimethyl fumarate

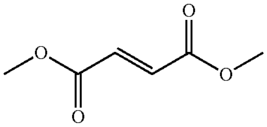

Necrosulfonamide

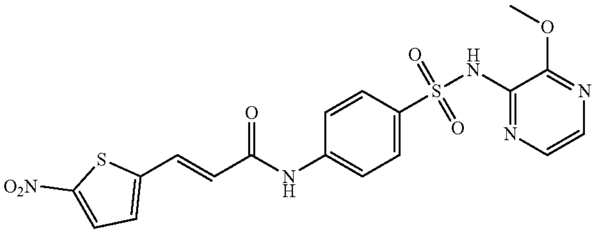 [SMILES: COc1nccnc1NS(=O)(=O)c1ccc(NC(=O)/C=C/c2ccc([N+](=O)[O-])s2)cc1]

or a pharmaceutically acceptable salt thereof.

In some embodiments, the compound of the present application is not C-5, C-7, C-8, C-22, C-24, C-25, Bay 11-7082, ASN-08966899, LDC7559, ibrutinib, afatinib, dimethyl fumarate, or necrosulfonamide.

In some embodiments, the present application provides any one of the following compounds:

C-5

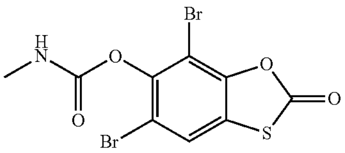 [SMILES: CNC(=O)Oc1c(Br)cc2sc(=O)oc2c1Br]

-continued

C-7

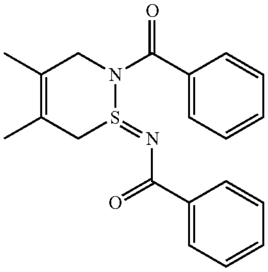 [SMILES: CC1=C(C)C/S(=N\C(=O)c2ccccc2)N(C(=O)c2ccccc2)C1]

-continued

C-8

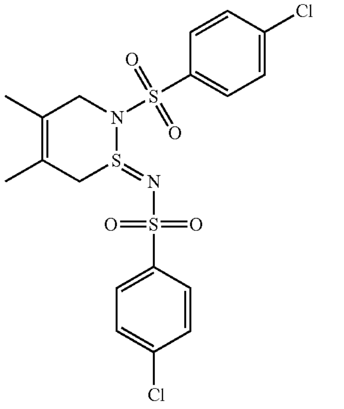 [SMILES: CC1=C(C)C/S(=N\S(=O)(=O)c2ccc(Cl)cc2)N(S(=O)(=O)c2ccc(Cl)cc2)C1]

C-22

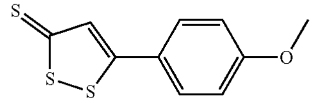

C-24

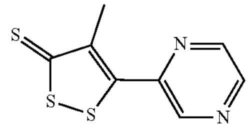

C-25

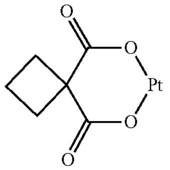

Bay 11-7082

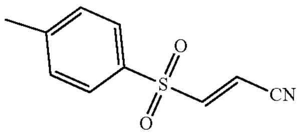

ASN-08966899

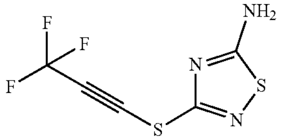

or a pharmaceutically acceptable salt thereof.

In some embodiments, the compound of the present application is not C-5, C-7, C-8, C-22, C-24, C-25, Bay 11-7082, or ASN-08966899.

Pharmaceutically Acceptable Salts

In some embodiments, a salt of a compound disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of the present disclosure include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include gluconate, sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of the present disclosure include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds disclosed herein, or pharmaceutically acceptable salts thereof, are substantially isolated.

Methods of Making

Compounds disclosed herein, including salts thereof, can be prepared using known organic synthesis techniques and can be synthesized according to any of numerous possible synthetic routes. A person skilled in the art knows how to select and implement appropriate synthetic protocols, and appreciates that a broad repertoire of synthetic organic reactions is available to be potentially employed in synthesizing compounds provided herein.

Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry:*

*Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

Methods of Use

Figure 67:
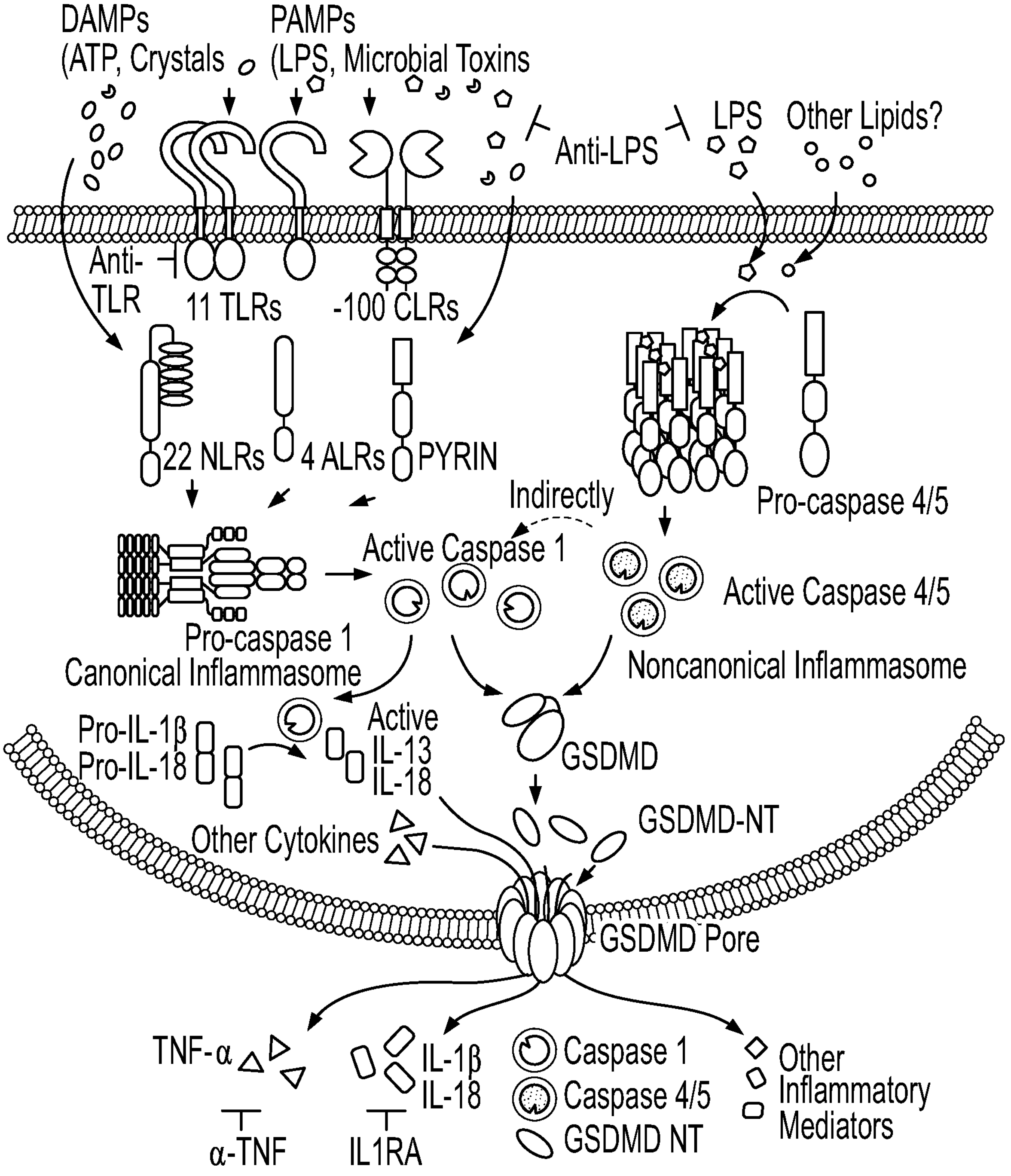
Figure 68:
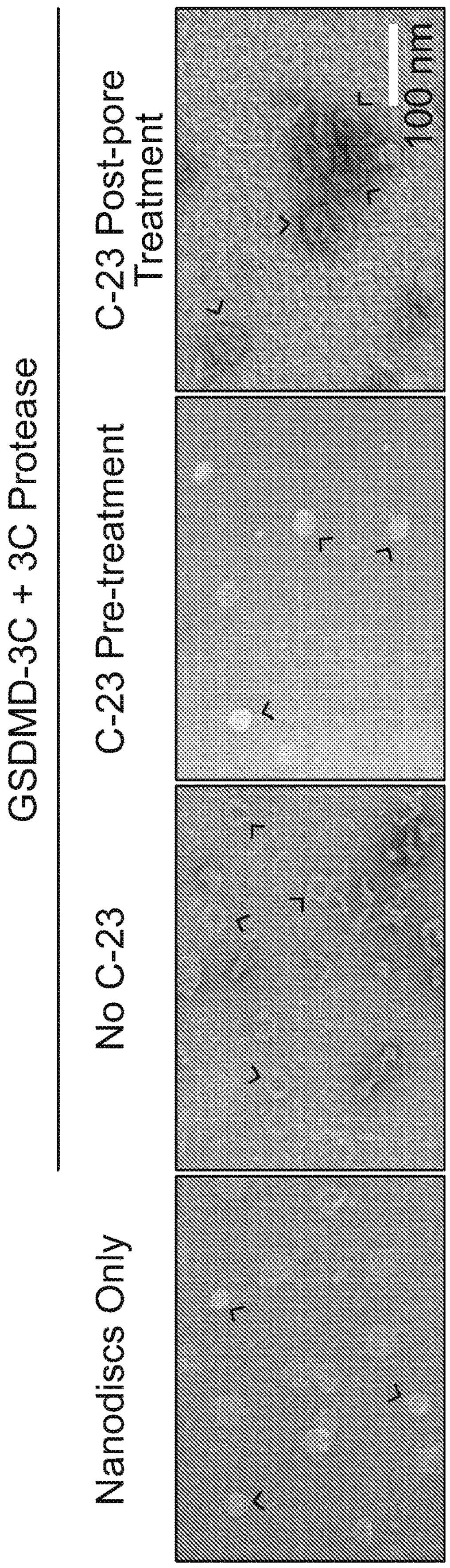
FIG. 68 contains negative stain EM images of PS-containing nanodiscs with or without incubation with GSDMD-3C plus 3C protease. In the 3rd image from the left, C-23 was added to the GSDMD-3C plus 3C protease mixture before it was added to the nanodiscs; in the 4th image C-23 was added after the mixture was incubated with nanodiscs when pores had formed. Scale bar, 100 nm. Arrows point to empty nanodiscs and pores.
Figure 69:
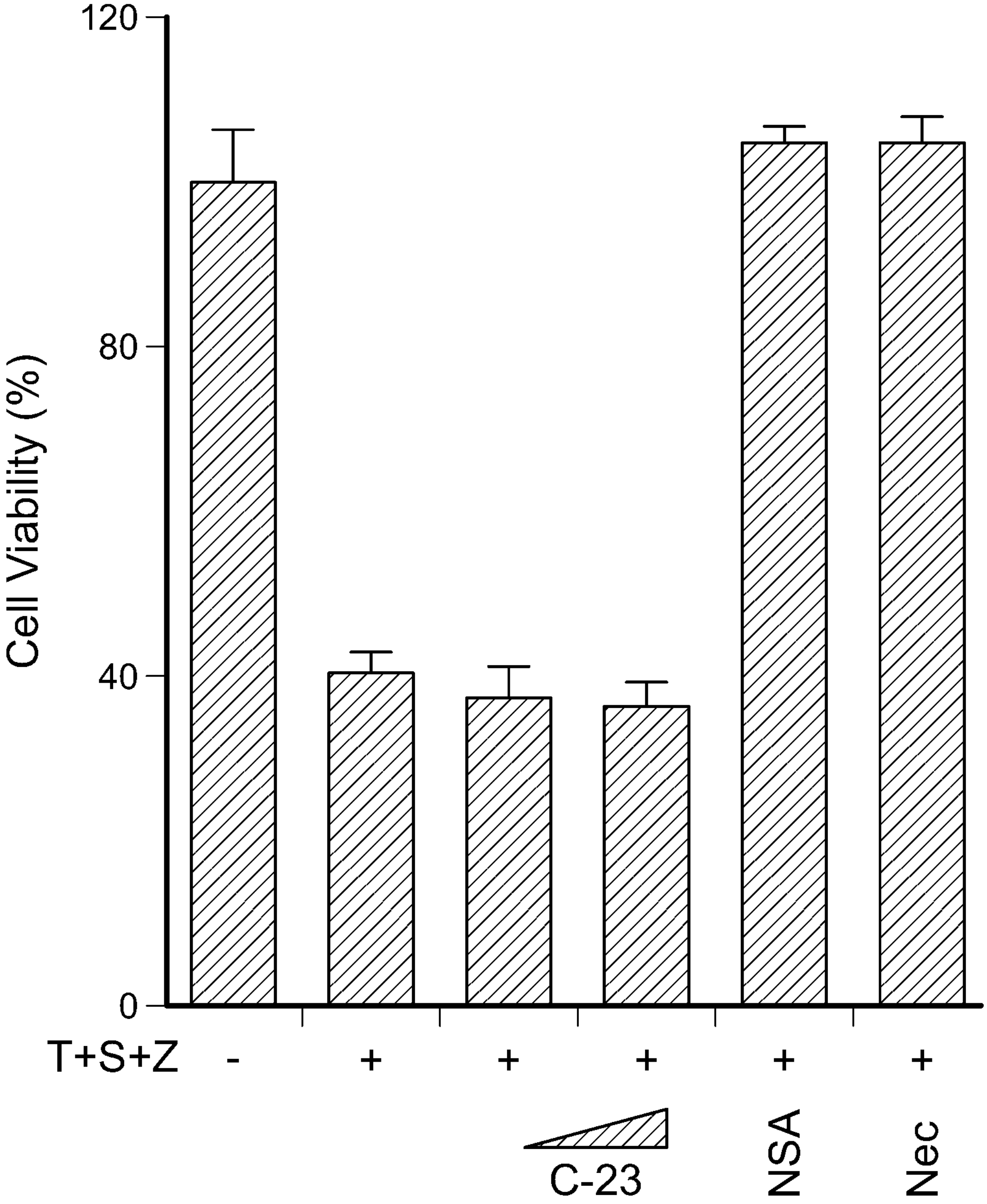
FIG. 69 contains a bar graph showing experimental results for the HT-29 cells that were pretreated (10 μM and 50 μM) or not with disulfiram (C-23) or 2 μM necrosulfonamide (NSA) or 10 μM Necrostatin-1 (Nec) for 1 h before adding 20 ng/ml TNFα (T), 100 nM SMAC mimetic (S), and 20 μM z-VAD-fmk (Z) and analyzed for cell viability by CellTiter-Glo assay 24 h later. Graphs show mean±s.d; data are representative of three independent experiments. **P<0.01.
Figure 70:
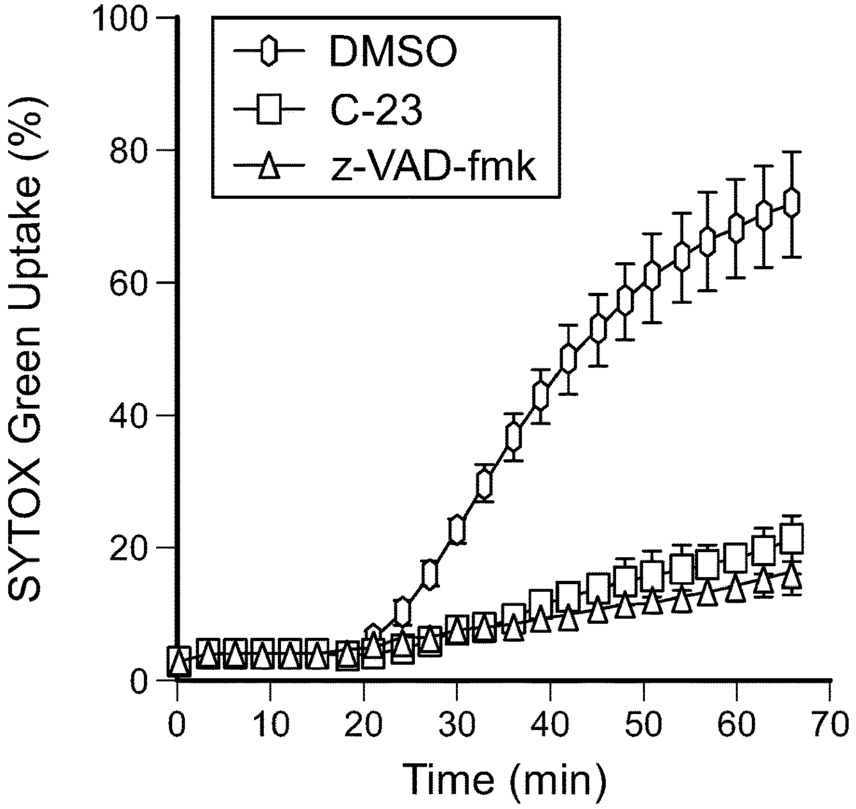
FIG. 70 contains a line graph showing results of pyroptosis as measured by SYTOX Green uptake in the presence of no inhibitor or 30 μM C-23 or z-VAD-fmk.
Figure 71:
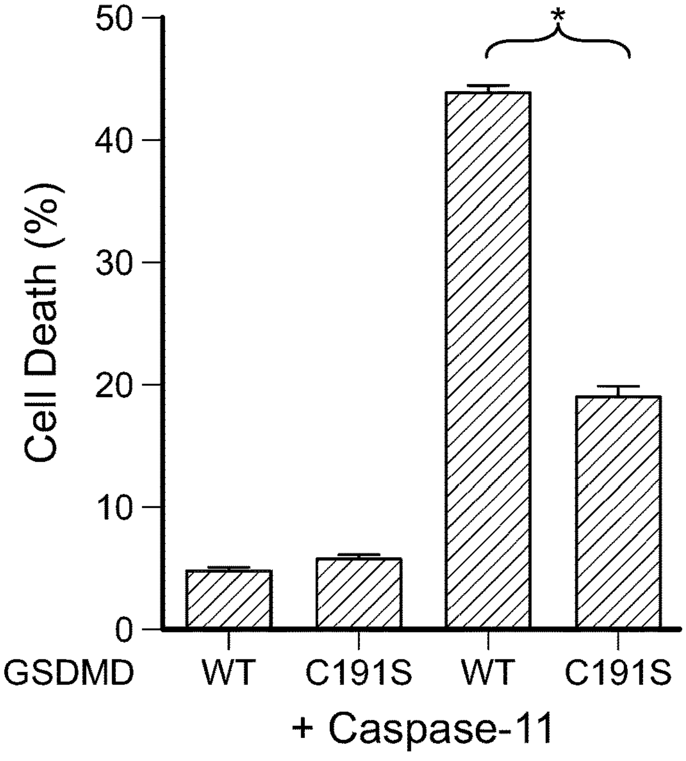
FIG. 71 contains a bar graph showing results of an experiment when full-length (FL) human GSDMD and GSDMD C191S were co-expressed with Caspase-11 in HEK293T cells. Cell death was determined by CytoTox96 cytotoxicity assay 20 hrs after transfection.
Figure 72:
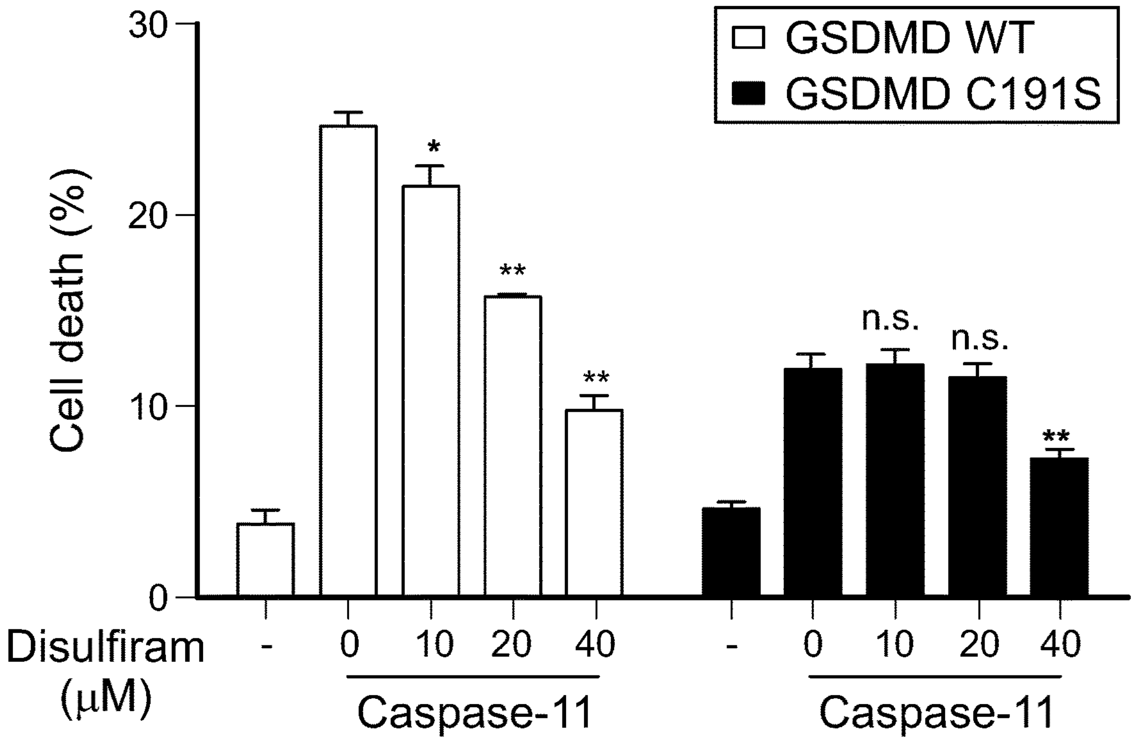
FIG. 72 contains a bar graph showing results of an experiment when FL human WT or C191S GSDMD were co-expressed with caspase-11 in HEK293T cells. 8 h post transfection, the indicated amount of disulfiram was added and cell death was determined by LDH release 12 h later. The bar graph shows the mean±s.d. of 1 representative experiment of three independent experiments performed. *P<0.05, **P<0.01, n.s., not significant.
Figure 73:
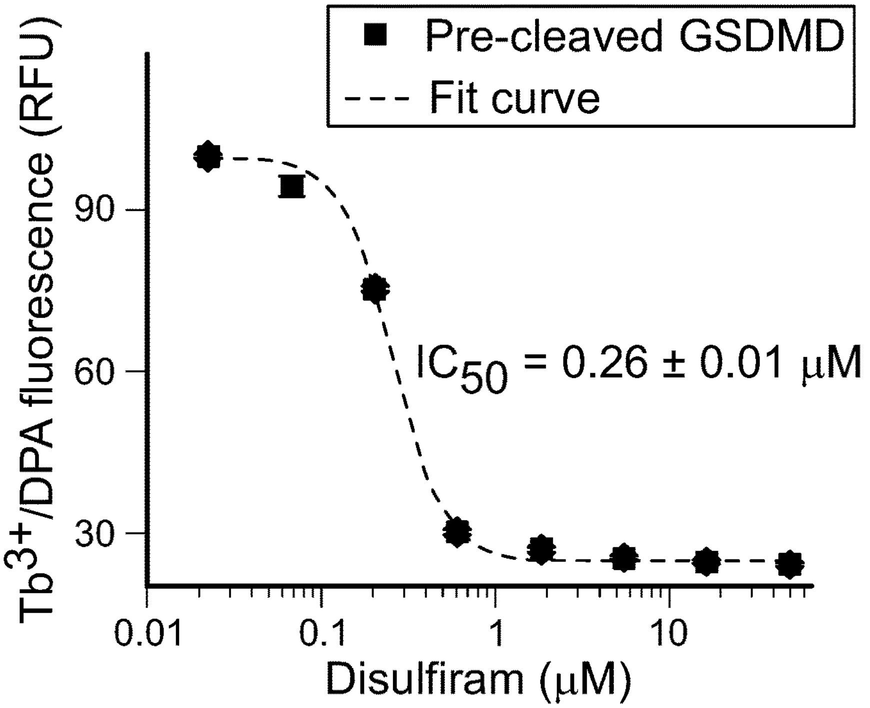
FIG. 73 contains a line plot showing dose response curve of disulfiram in liposome leakage induced by pre-cleaved human GSDMD (0.3 μM).
Figure 74:
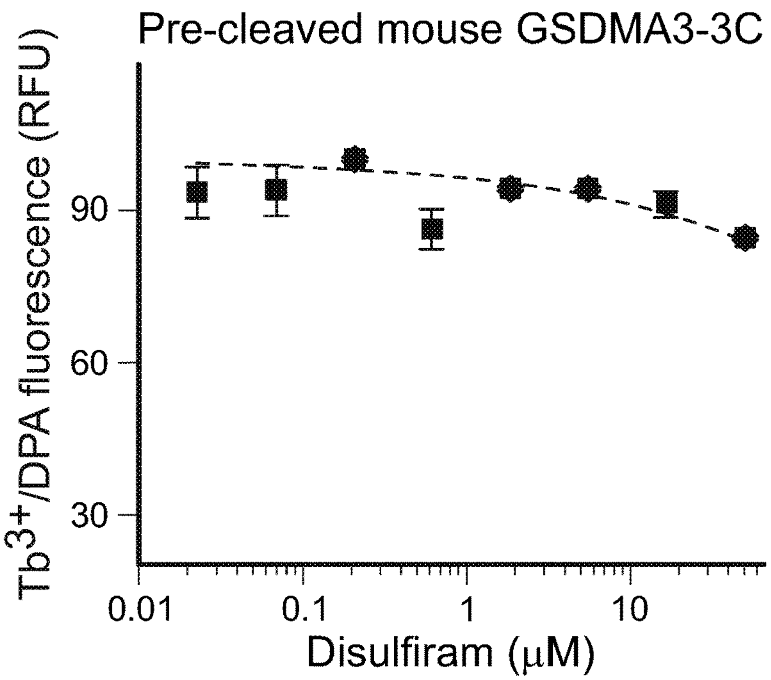
FIG. 74 contains a line plot showing dose response curve of disulfiram in liposome leakage induced by pre-cleaved mouse GSDMA3-3C (0.3 μM).
Figure 75:
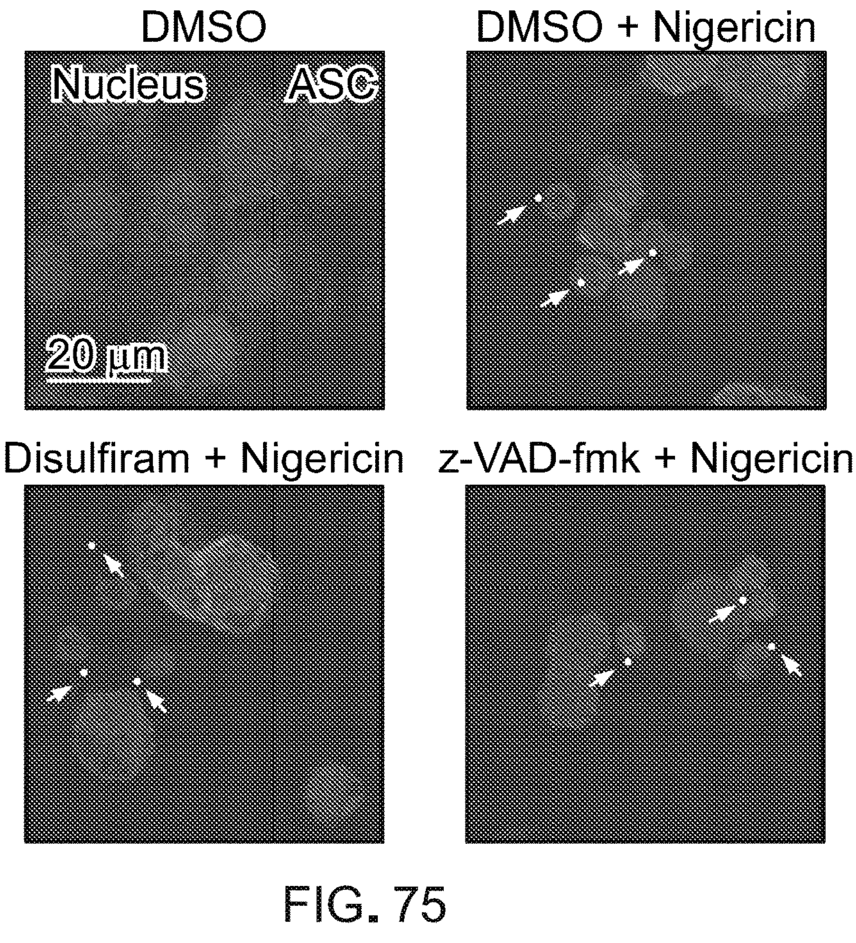
FIG. 75 contains images showing LPS-primed THP-1 cells, pretreated or not with 30 μM disulfiram or z-VAD-fmk for 1 hr, and stimulated with nigericin or medium.
Figure 76:
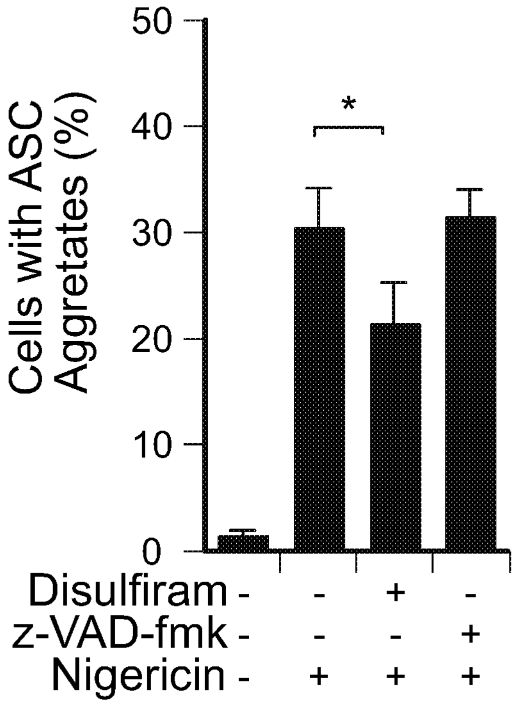
FIG. 76 contains a bar graph showing results of analysis of LPS-primed THP-1 cells for ASC specks.
Figure 77:
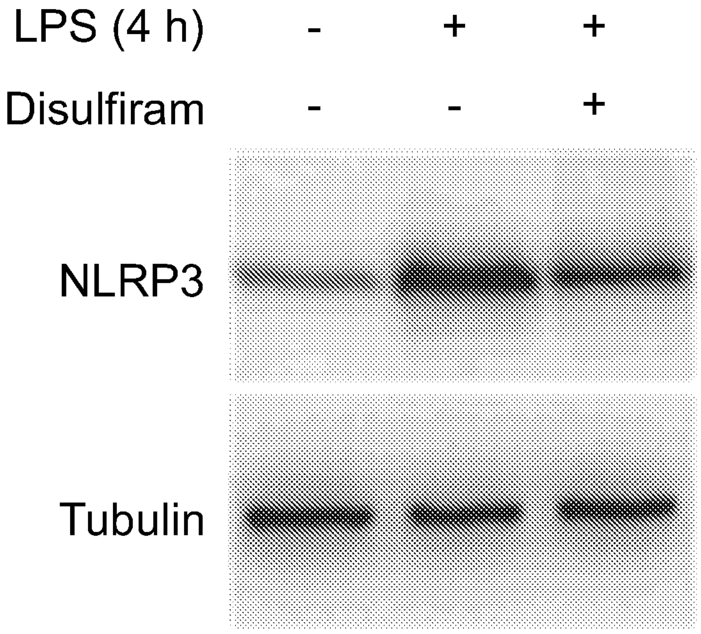
FIG. 77 contains an image showing results of analysis of LPS-primed THP-1 cells for NLRP3.
Figure 78:
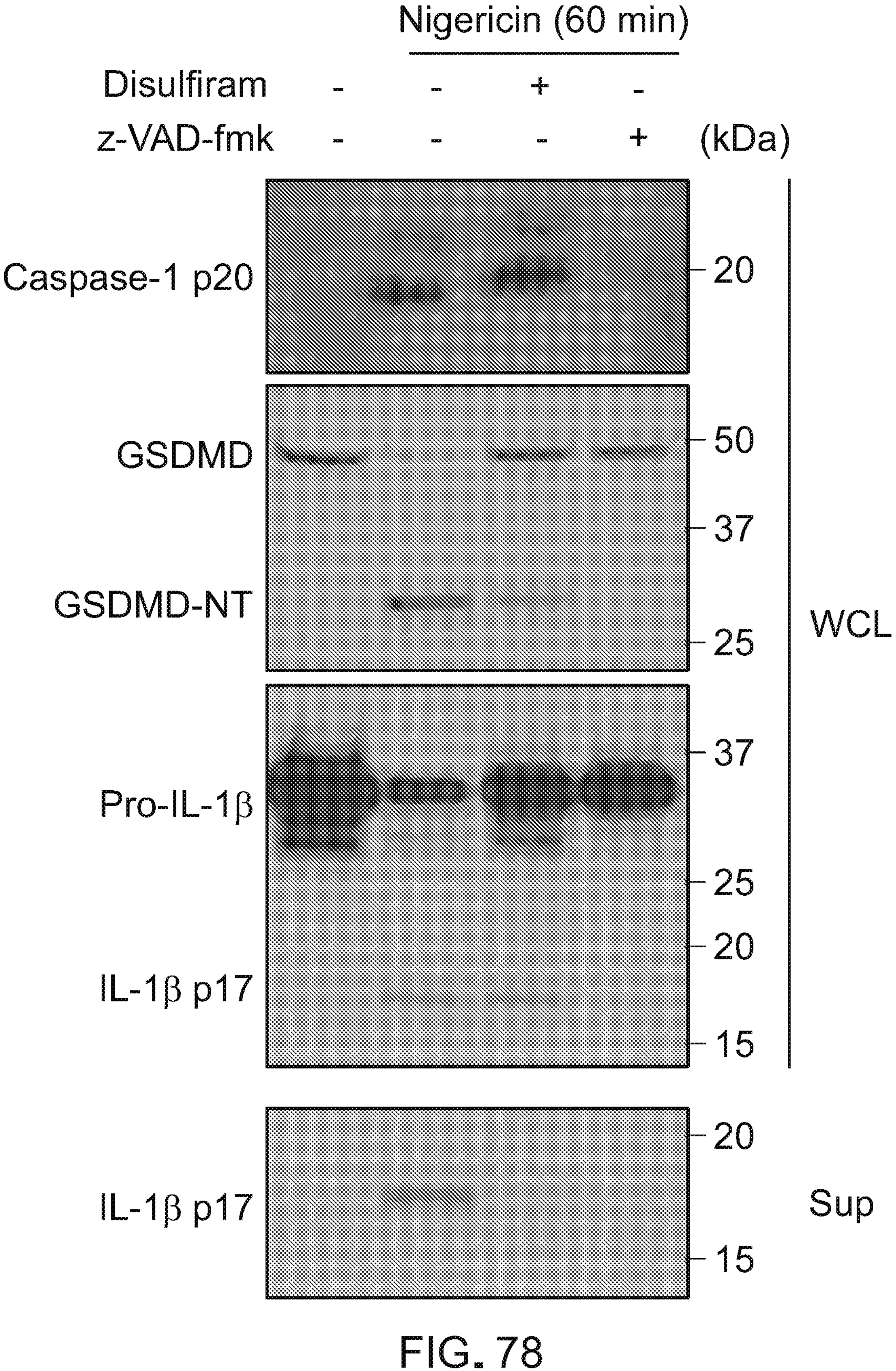
FIG. 78 contains an image showing results of analysis of LPS-primed THP-1 cells for caspase-1, GSDMD, and pro-IL-1β cleavage and IL-1 release by immunoblot of whole cell lysate (WCL) or culture supernatants.
Figure 79:
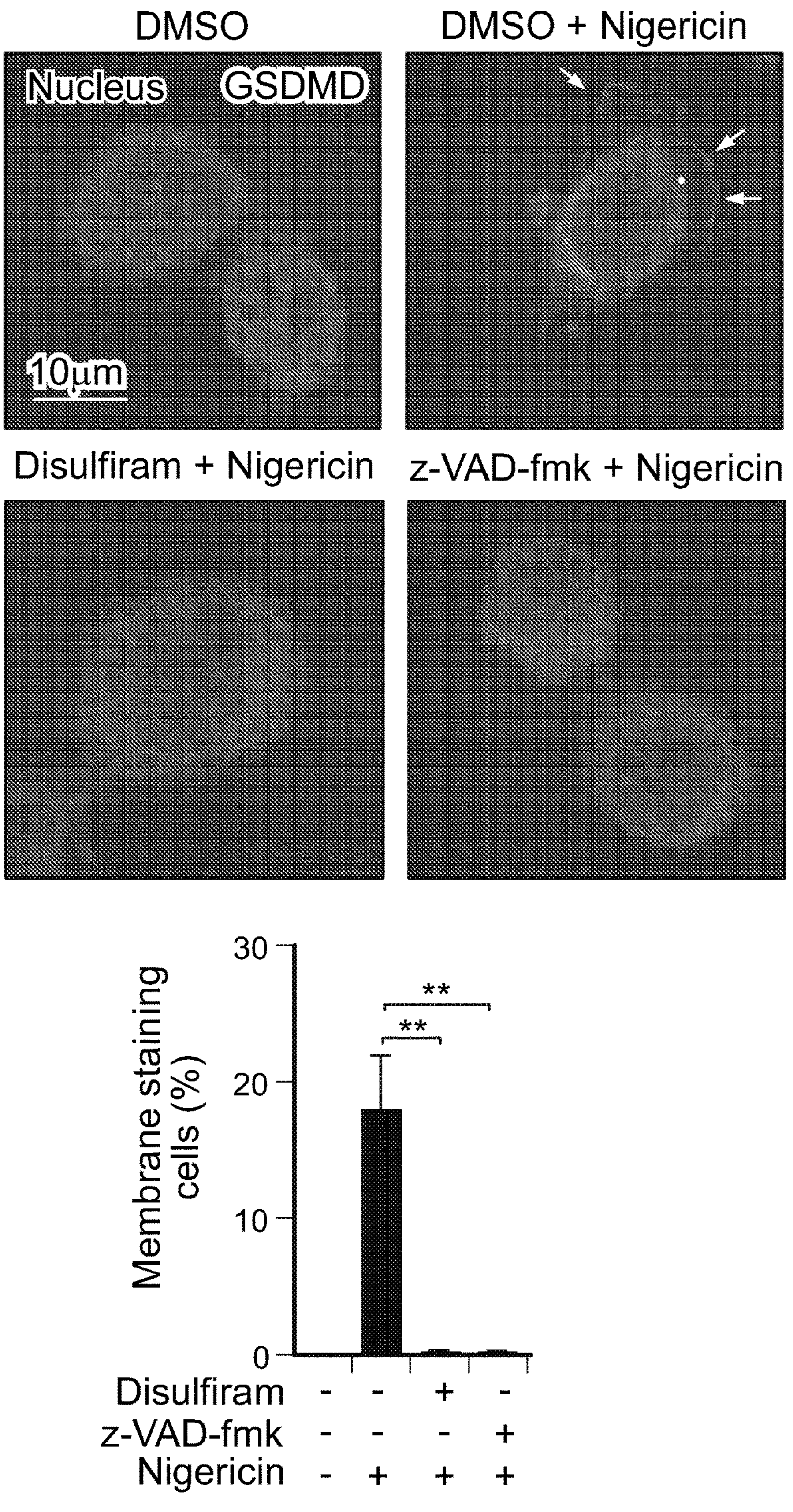
FIG. 79 contains an image and a bar graph showing redistribution of GSDMD to the plasma membrane. Cells were fixed 30 min after adding nigericin and stained for GSDMD using a previously unreported monoclonal antibody generated in house Shown are representative confocal microscopy images and quantification of the proportion of cells with GSDMD membrane staining and pyroptotic bubbles. Arrows indicate GSDMD staining of pyroptotic bubbles. Graphs show the mean±s.d; data are representative of three independent experiments. *P<0.05, **P<0.01.
Figure 80:
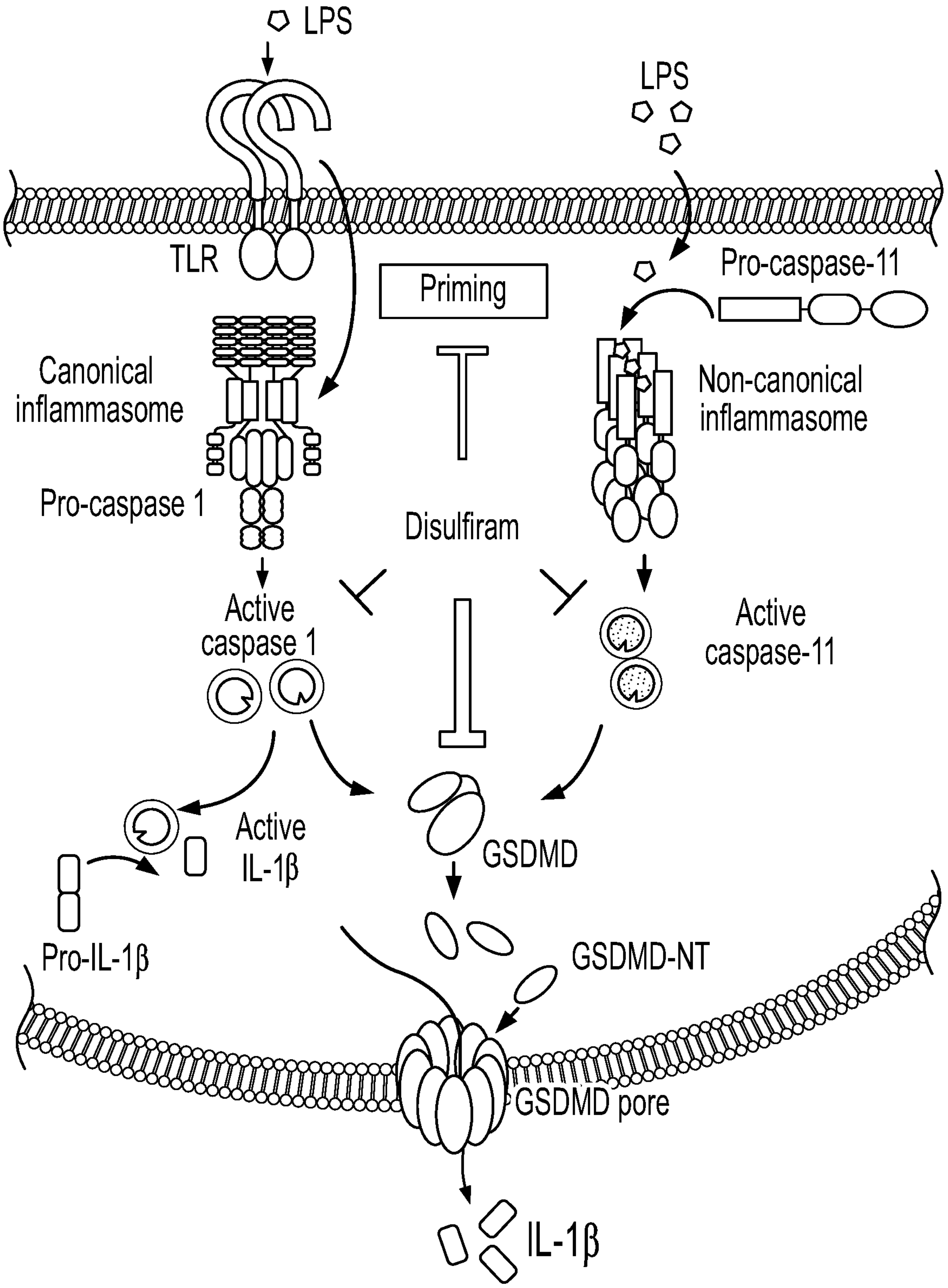
FIG. 80 contains an image showing a model of inflammasome pathway steps and their inhibition by disulfiram, with a main effect on GSDMD.
Figure 81:
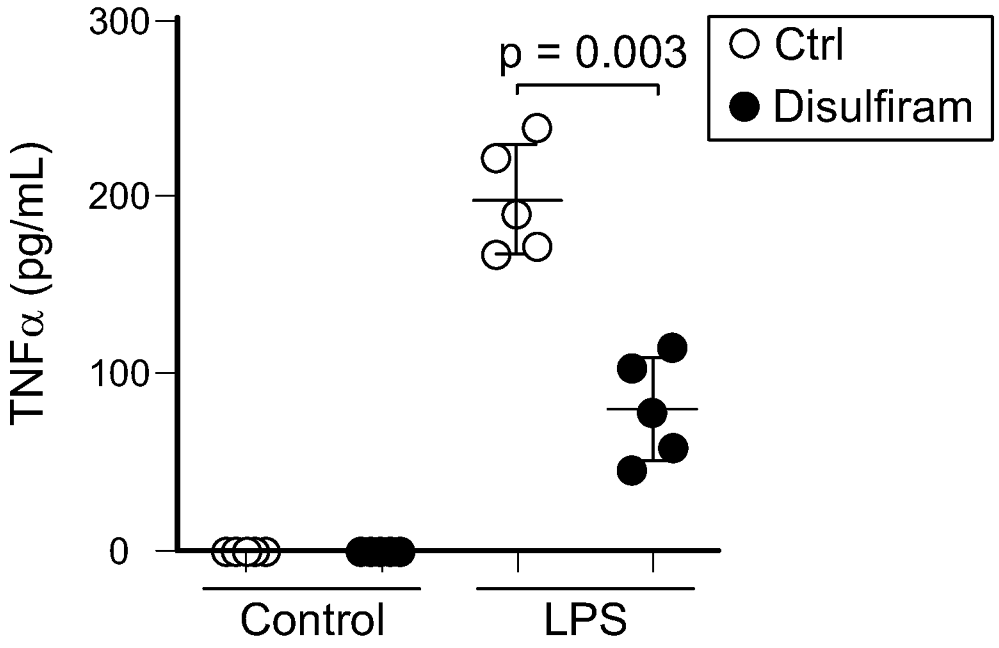
FIG. 81 contains a plot showing results of an experiment where mice were pretreated with disulfiram (50 mg/kg) or vehicle (Ctrl) by intraperitoneal injection 24 and 4 h before intraperitoneal challenge with 15 mg/kg LPS and followed for survival. TNFa was measured by ELISA (n=5/group) 12 hr post LPS challenge. Shown are mean±s.d.
Figure 82:
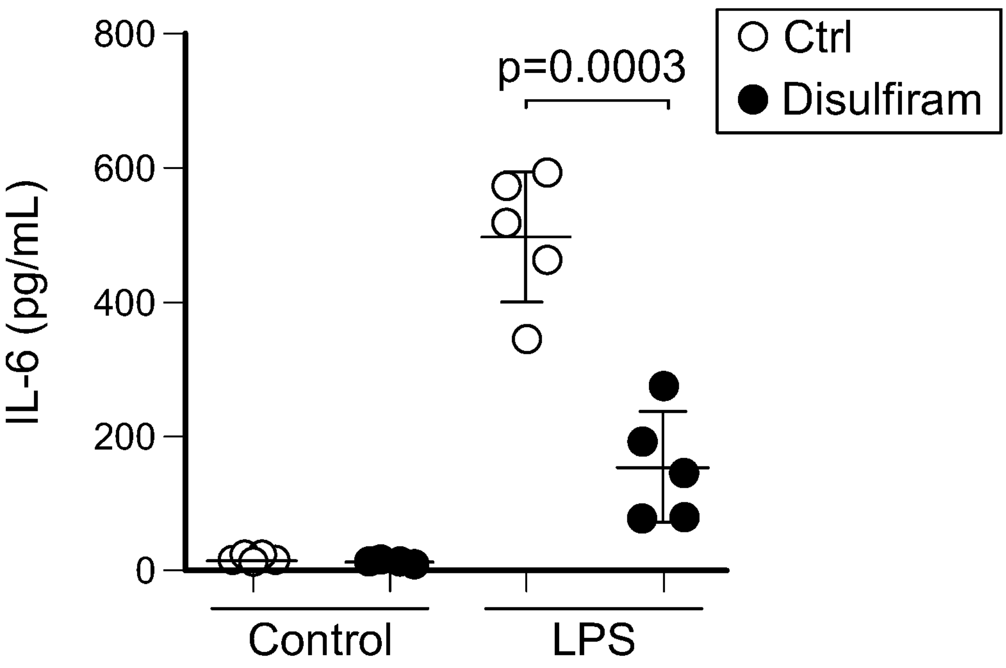
FIG. 82 contains a plot showing results of an experiment where mice were pretreated with disulfiram (50 mg/kg) or vehicle (Ctrl) by intraperitoneal injection 24 and 4 h before intraperitoneal challenge with 15 mg/kg LPS and followed for survival. Serum IL-6 were measured by ELISA (n=5/group) 12 hr post LPS challenge. Shown are mean±s.d.
Figure 83:
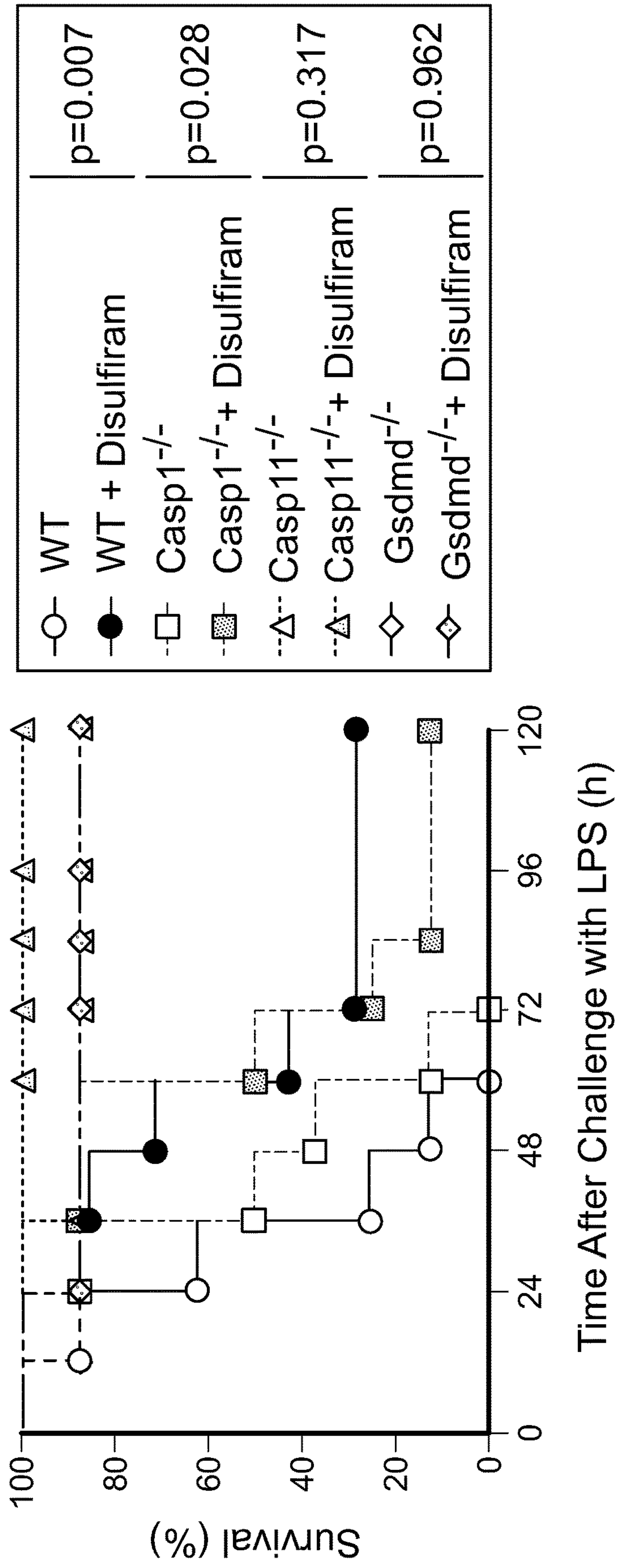
FIG. 83 contains a line plot showing results of an experiment where mice were pretreated with disulfiram (50 mg/kg) or vehicle (Ctrl) by intraperitoneal injection 4 h before and daily after intraperitoneal LPS challenge (25 mg/kg) and followed for survival.
Figure 84:
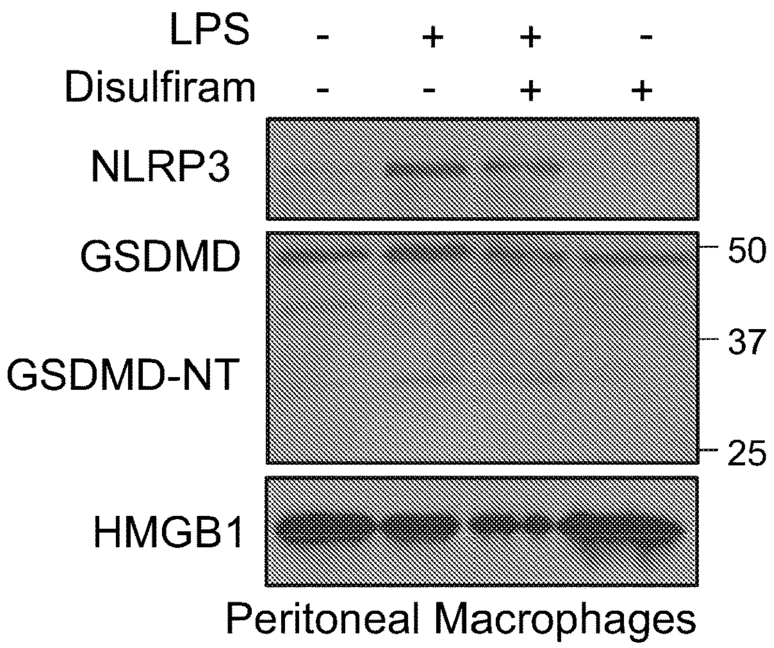
FIG. 84 contains an image showing results of an experiments where peritoneal macrophages from four indicated groups of mice were analyzed for NLRP3, GSDMD and HMGB1 by immunoblot.
Figure 85:
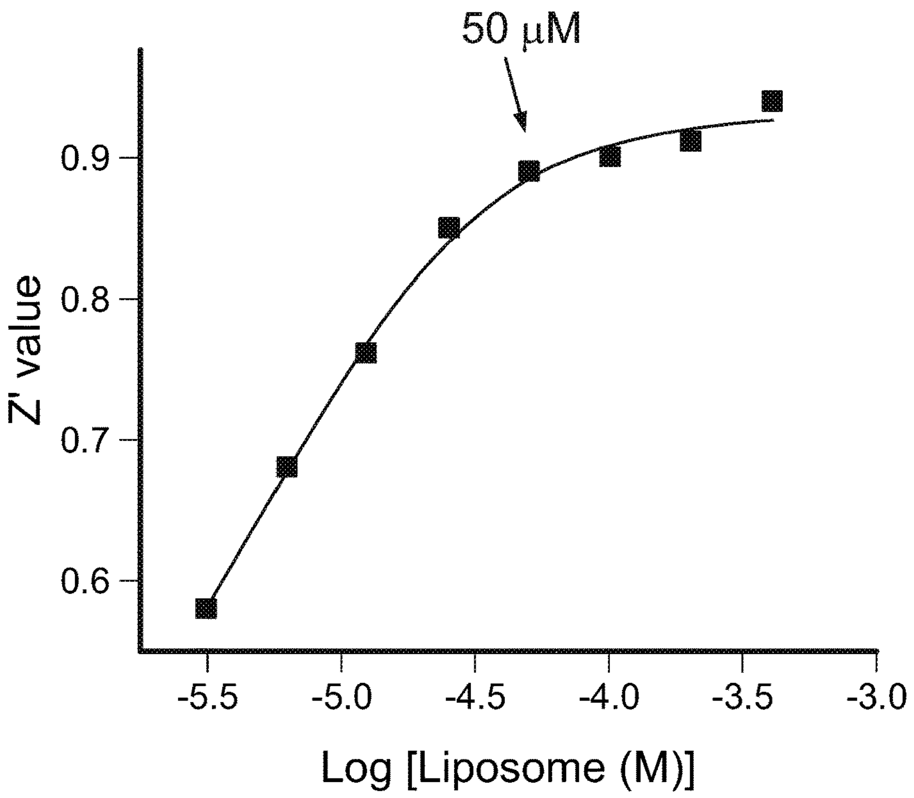
FIG. 85 contains a line plot showing results of a liposome leakage assay. GSDMD (2.5 μM) and caspase-11 (2.5 μM) were incubated in liposome solutions at various concentrations in 20 mM HEPES buffer (150 mM NaCl) for 1 h. The concentration of liposome lipids for the screen was set at 50 μM.
Figure 86:
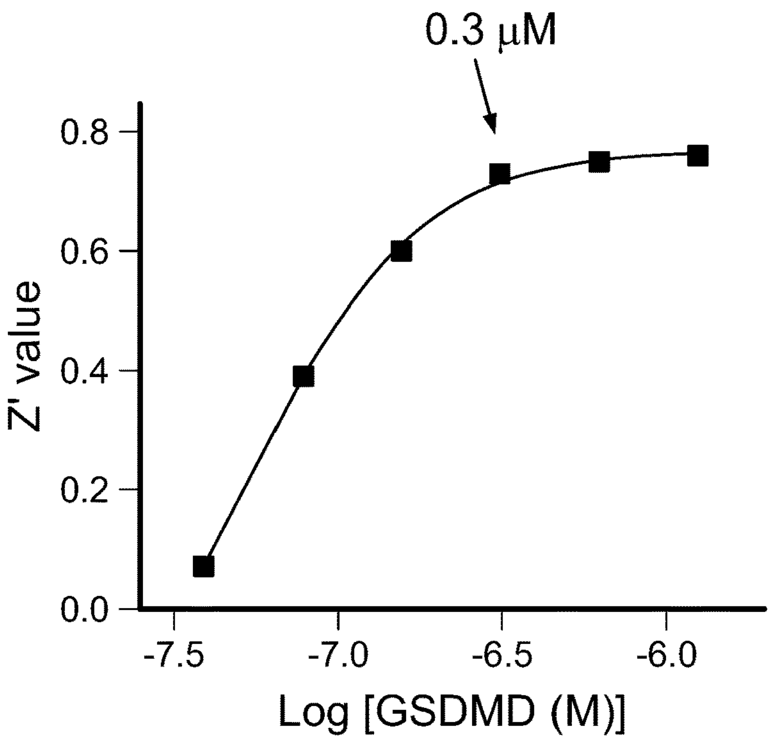
FIG. 86 contains a line plot showing results of liposome leakage assay. Different concentrations of GSDMD and caspase-11 (1:1 ratio) were incubated in liposome (50 μM) solutions for 1 h. The concentration of GSDMD used in the screen was set at 0.3 μM.
Figure 87:
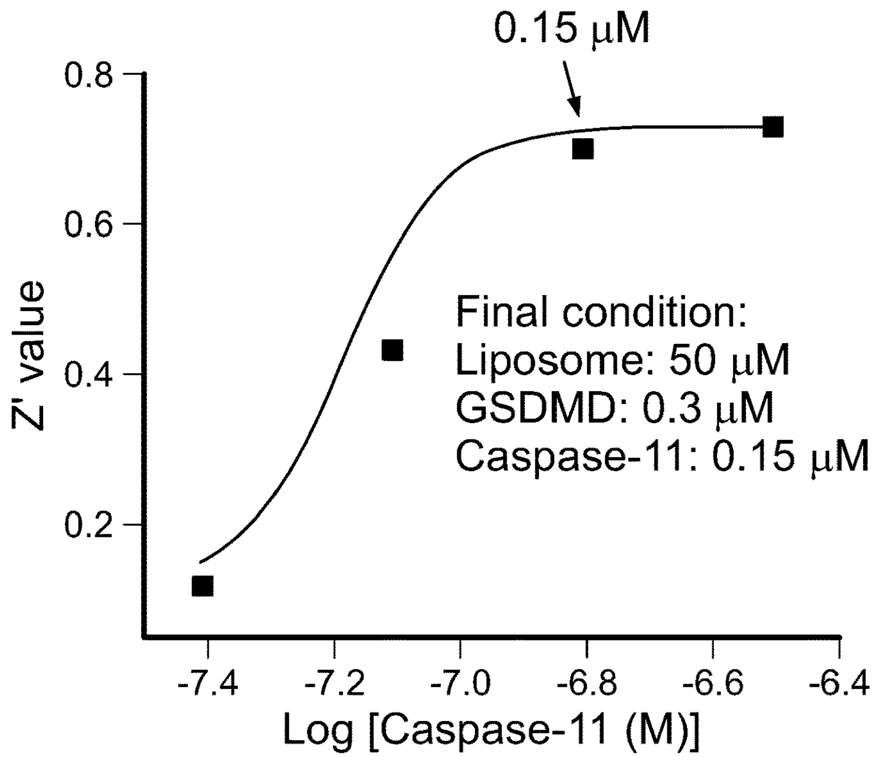
FIG. 87 contains a line plot showing results of liposome leakage assay. Different concentrations of caspase-11 and GSDMD (0.3 μM) were incubated in liposome (50 μM) solutions for 1 h. The concentration of caspase-11 used in the screen was set at 0.15 μM. The fluorescence intensity at 545 nm was measured after excitation at 276 nm.
Figure 88:
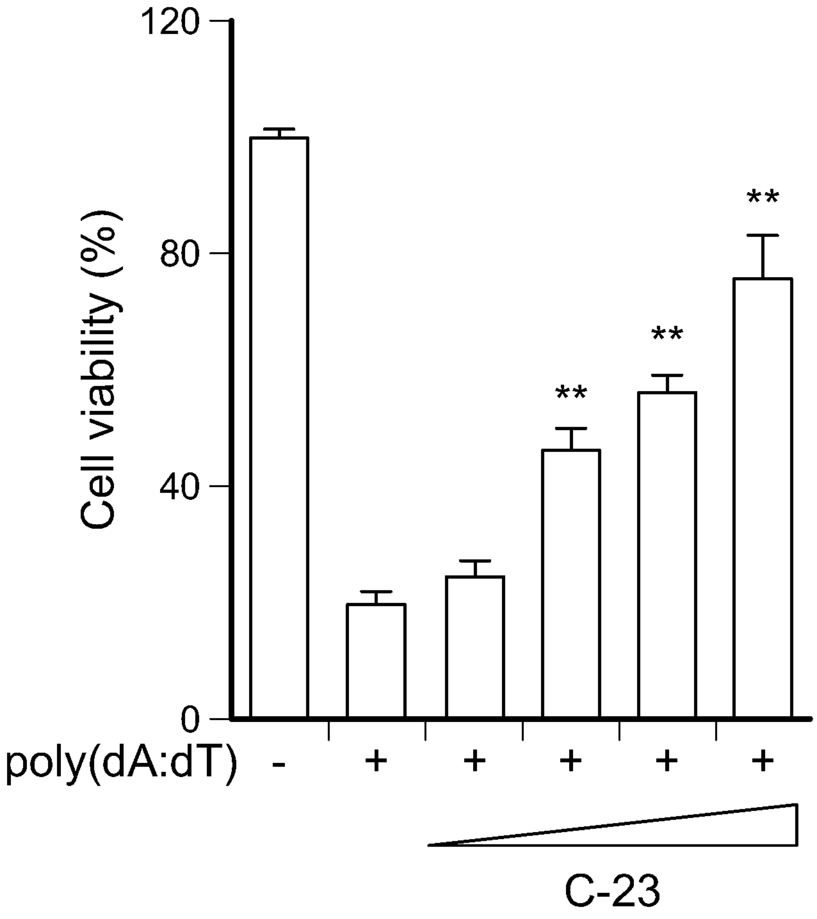
FIG. 88 contains a bar graph showing results of an experiment where mouse iBMDMs were pretreated or not with disulfiram (C-23) ranging from 5-40 μM for 1 h before transfection with PBS or poly(dA:dT) and analyzed for cell viability by CellTiter-Glo assay 4 h later. $^{**}P<0.01$.
Figure 90:
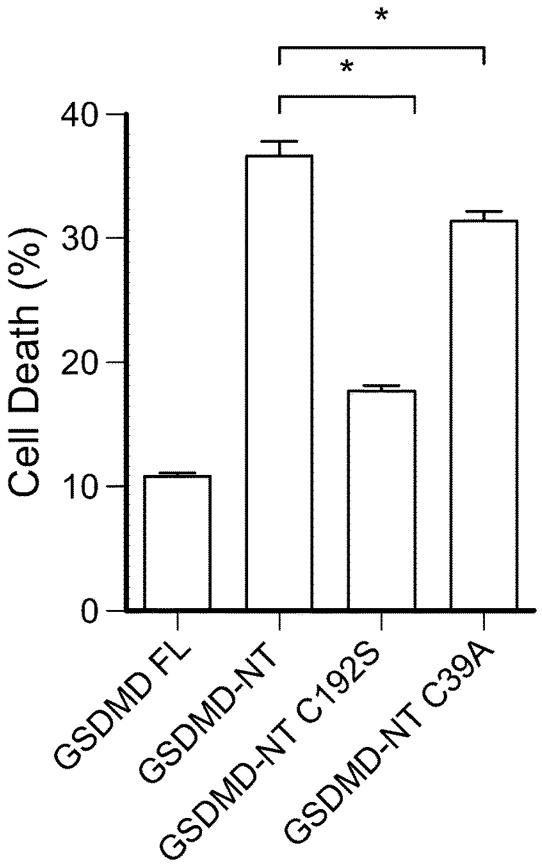
FIG. 90 contains a bar graph showing results of an experiment where FL mouse GSDMD or WT, C192S or C39A GSDMD-NT were transiently expressed in HEK293T cells. Cell death was determined by CytoTox96 cytotoxicity assay 20 hrs after transfection. c shows the mean±s.d. of 1 representative experiment of three independent experiments performed. $^{*}P<0.05$.
Figure 91:
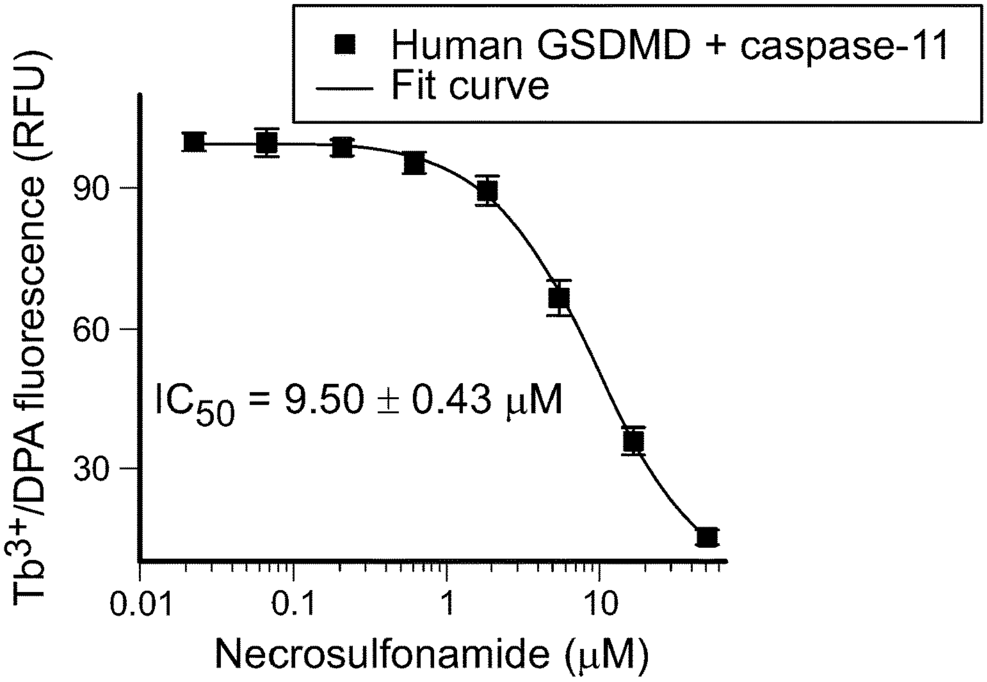
FIG. 91 contains a line plot showing results of GSDMD-mediated liposome leakage assay induced by 0.3 μM GSDMD plus 0.15 μM caspase-11 for compound necrosulfonamide (dose response curve).
Figure 92:
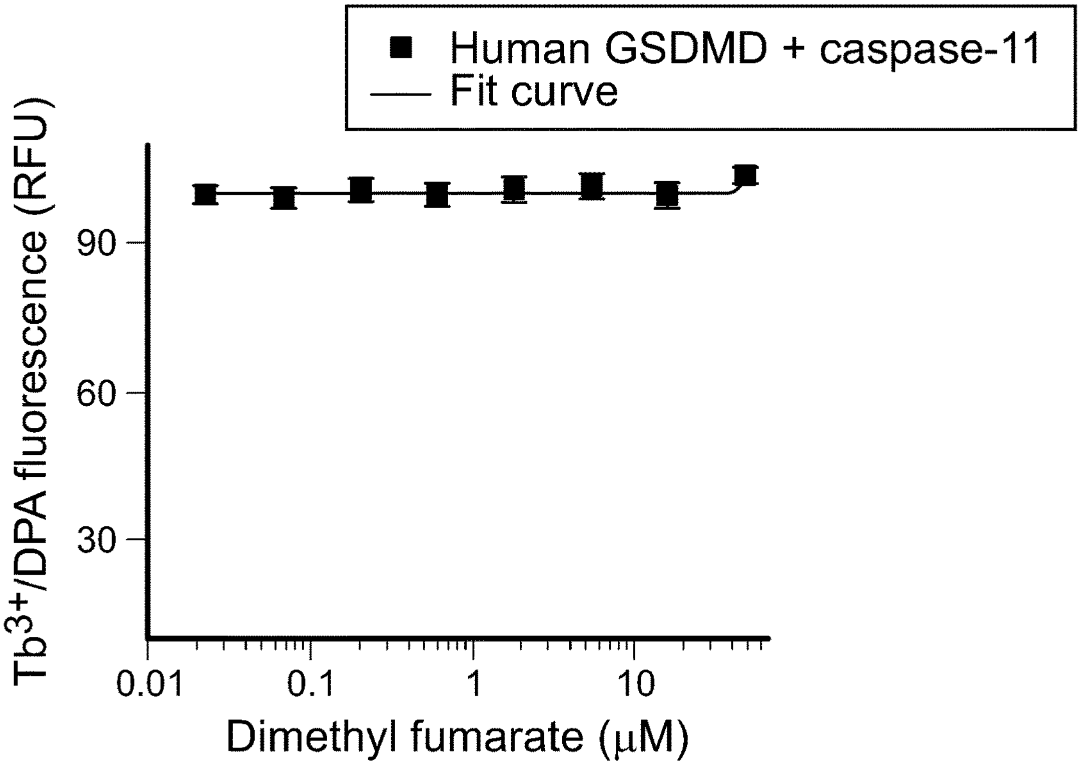
FIG. 92 contains a line plot showing results of GSDMD-mediated liposome leakage assay induced by 0.3 μM GSDMD plus 0.15 μM caspase-11 for compound dimethyl fumarate (dose response curve).
Figure 93:
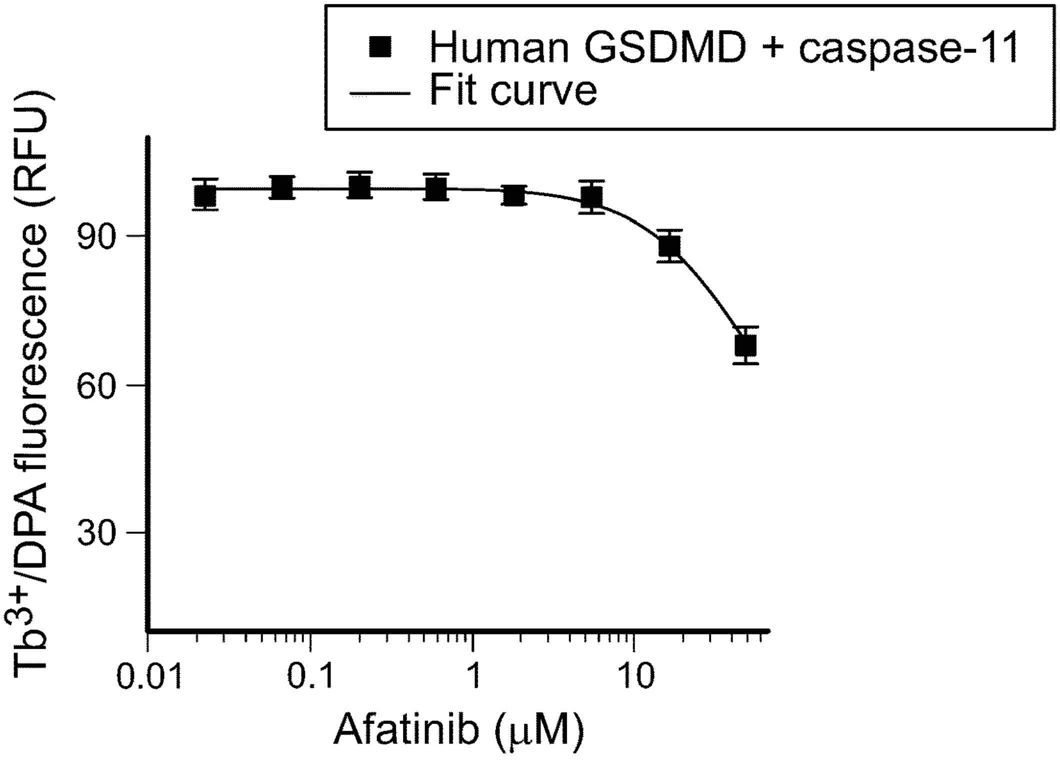
FIG. 93 contains a line plot showing results of GSDMD-mediated liposome leakage assay induced by 0.3 μM GSDMD plus 0.15 μM caspase-11 for compound afatinib (dose response curve).
Figure 94:
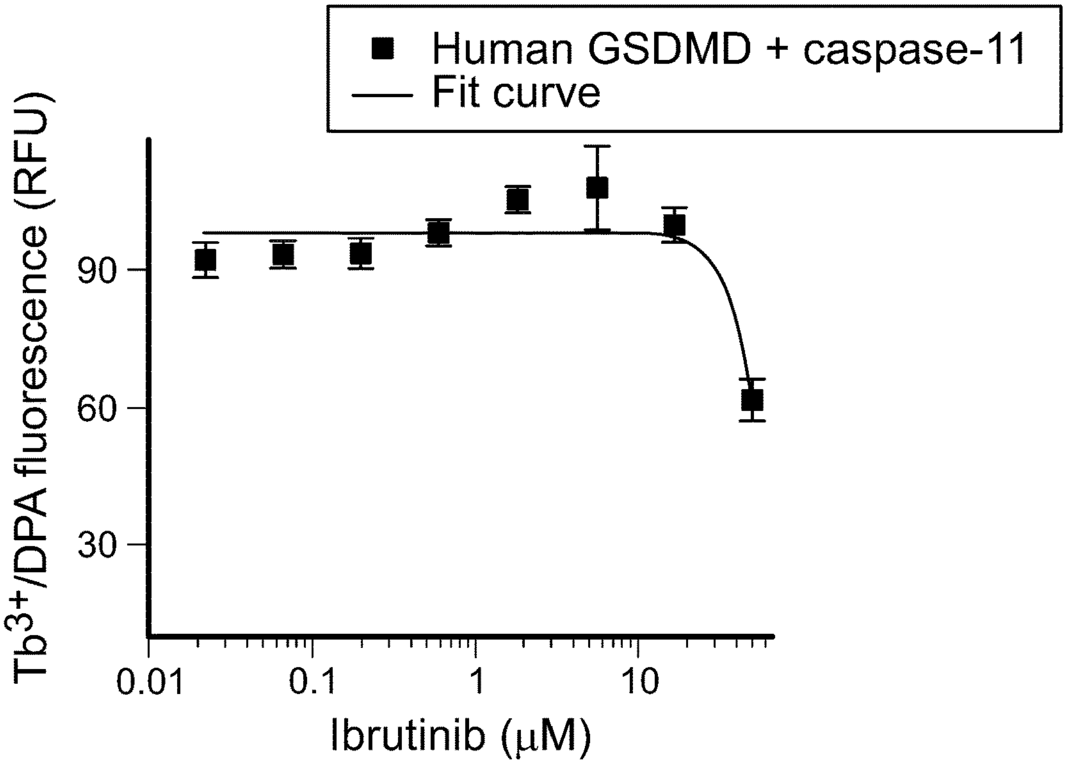
FIG. 94 contains a line plot showing results of GSDMD-mediated liposome leakage assay induced by 0.3 μM GSDMD plus 0.15 μM caspase-11 for compound ibrutinib (dose response curve).
Figure 95:
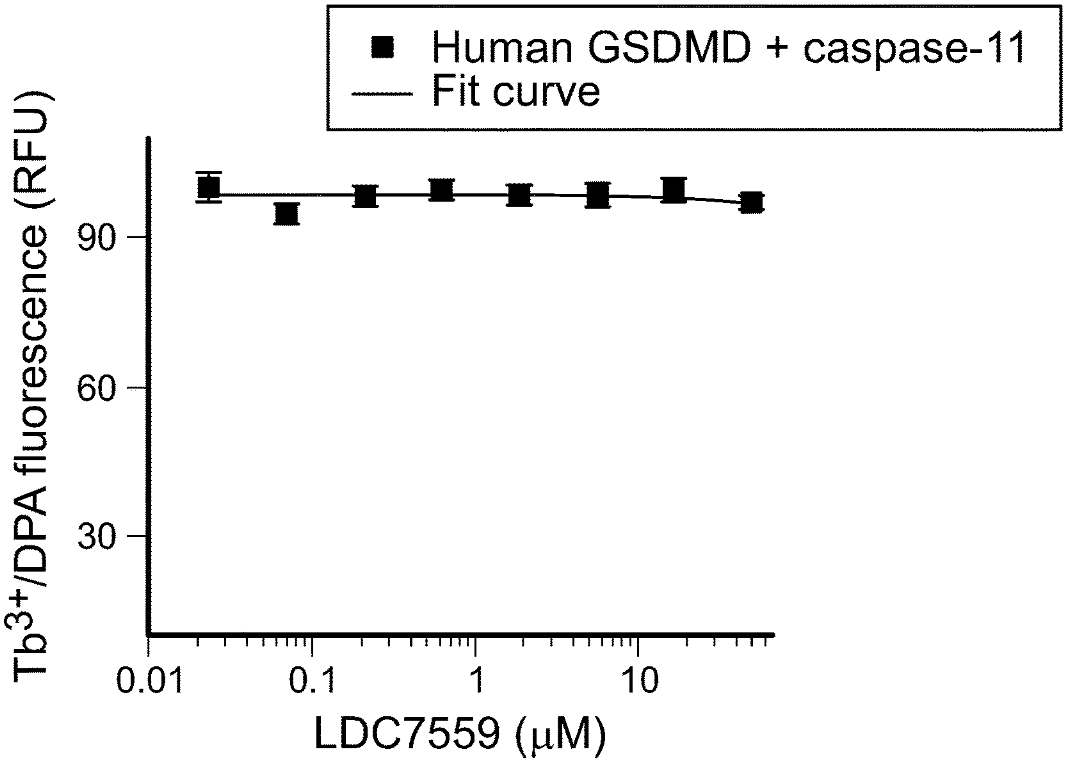
FIG. 95 contains a line plot showing results of GSDMD-mediated liposome leakage assay induced by 0.3 μM GSDMD plus 0.15 μM caspase-11 for compound LDC7559 (dose response curve).
Figure 96:
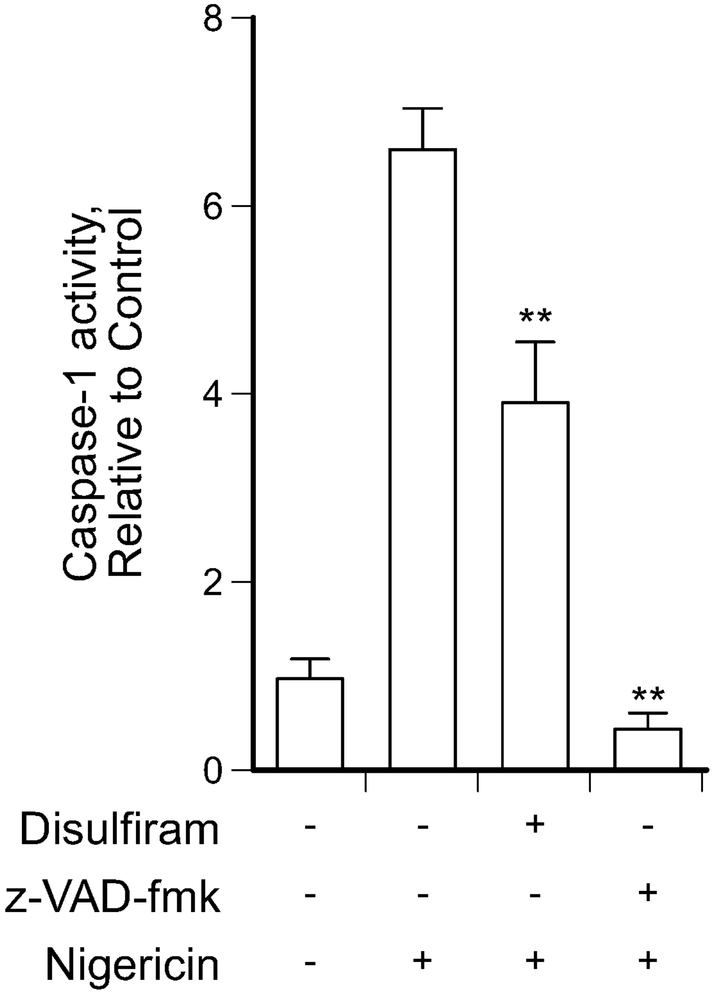
FIG. 96 contains a bar graph showing results of an experiment where LPS-primed THP-1 cells, pretreated or not with 30 μM disulfiram or z-VAD-fmk for 1 hr and stimulated with nigericin or medium, were analyzed for caspase-1 activity by a cell-permeable fluorescent caspase activity probe FAM-YVAD-FMK after 0.5 hr.
Figure 97:
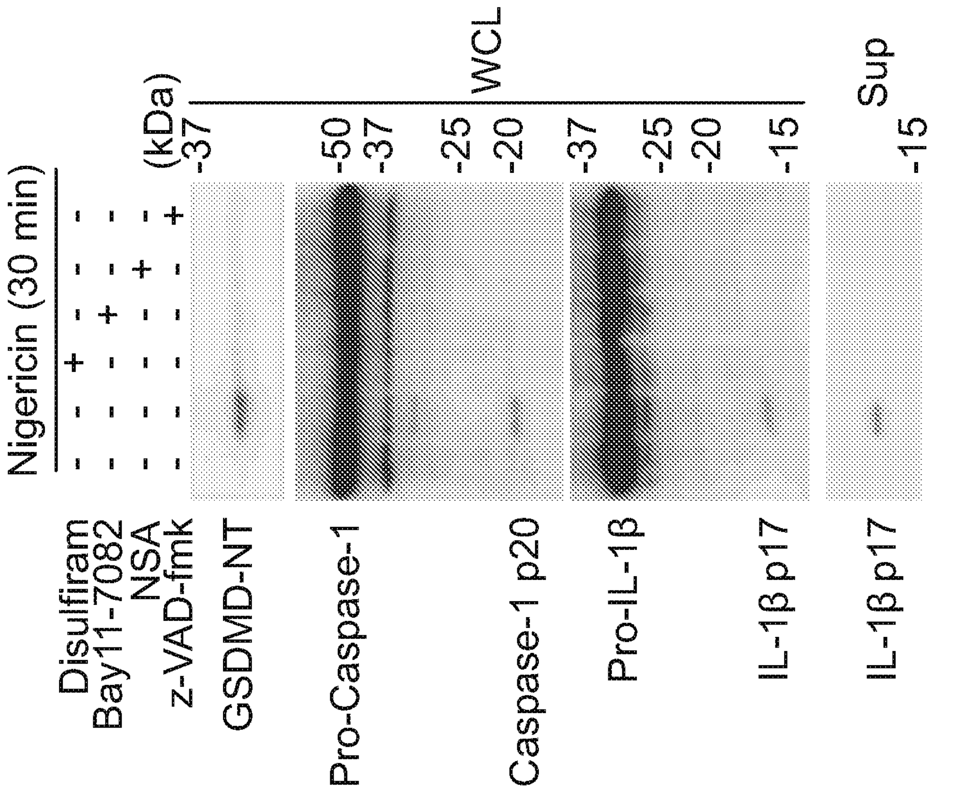
FIG. 97 contains a bar graph showing results of an experiment where LPS-primed THP-1 cells, after medium removal, were incubated with probe FAM-YVAD-FMK in FLICA assay buffer for another 0.5 hr before fluorescence reading. iBMDMs were pretreated with disulfiram, Bay 11-7082, necrosulfonamide (NSA) or z-VAD-fmk for 1 hr before treated or not with Nigericin for 0.5 hr. Whole cell lysates and culture supernatants were immunoblotted with the indicated antibodies.
Figure 98:
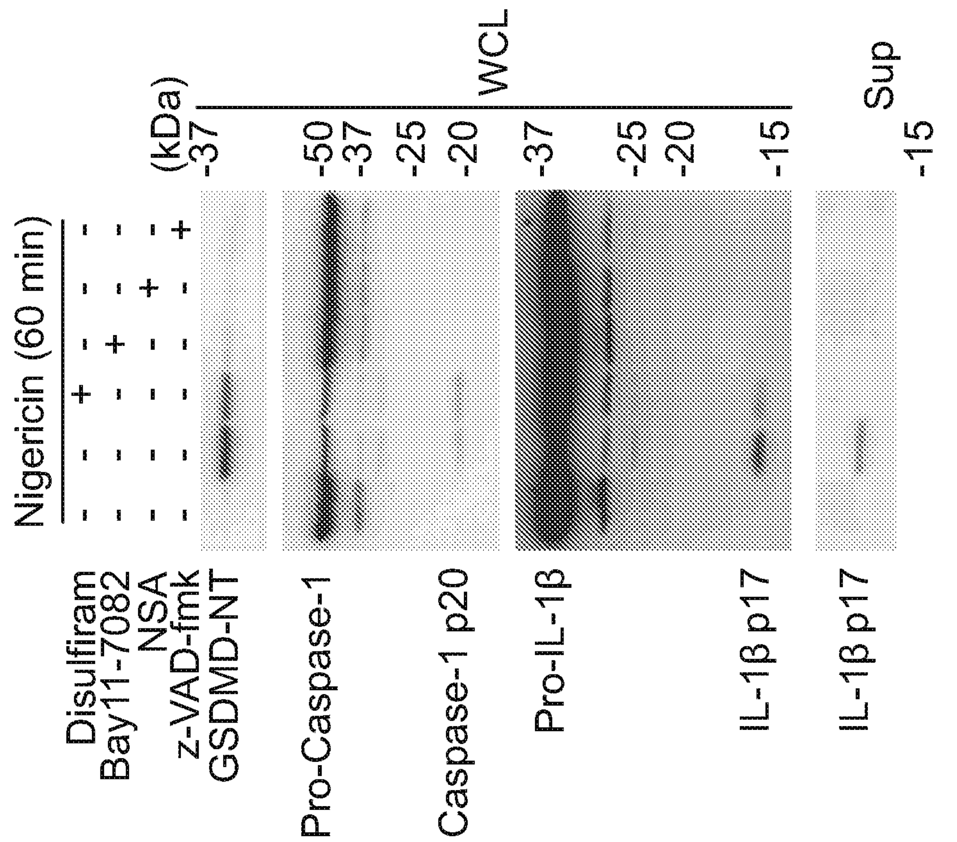
FIG. 98 contains a bar graph showing results of an experiment where LPS-primed THP-1 cells, after medium removal, were incubated with probe FAM-YVAD-FMK in FLICA assay buffer for another 0.5 hr before fluorescence reading. iBMDMs were pretreated with disulfiram, Bay 11-7082, necrosulfonamide (NSA) or z-VAD-fmk for 1 hr before treated or not with Nigericin for 1 hr. Whole cell lysates and culture supernatants were immunoblotted with the indicated antibodies.

Referring to FIG. 67, the inflammatory cascade begin when pathogen-associated molecular patterns (PAMPs) or damage-associated molecular patterns (DAMPs), also known as alarmins, are sensed by cell surface and endosomal pattern recognition receptors (PRR), such as Toll-like receptors (TLR) and C-type lectin receptors (CLR), and cytosolic sensors. Examples of PAMPs and DAMPs include LPS, bacterial toxins, bacterial proteins and nucleic acids, particulates (such as uric acid and cholesterol crystals and amyloid-β fibrils), hyaluronan, and extracellular ATP. In response, cellular mechanisms activate pro-caspase canonical or non-canonical inflammasomes, leading to the release of active inflammatory caspases. Examples of the inflammatory caspases include caspase-1, caspse-11, as well as caspase-4 and caspase-5. The activation of caspases in inflammasomes leads to caspase cleavage of cytoplasmic protein gasdermin, which produces a gasdermin N-terminal fragment (gasdermin-NT). In some instances, the caspase-cleavable gasdermin protein is selected from the following members of the gasdermin family: GSDMA, GSMDB, GSDMC, GSDMD, DFNA5, and DFNB59. The gasdermin-NT then binds to the cell membrane from the cytosolic side to form pores that permeabilize the cell membrane causing cytokine secretion and pyroptosis. DFNA5 is activated by caspase-3 during classical apoptosis. The proteases that activate the other gasdermins are currently not known, but are not caspases and may be activated independently of inflammasomes. Typically, gasdermin binds to acidic lipids that are restricted to the inner leaflet of mammalian membranes, such as phosphatidylinositol phosphates (PIPs), phosphatidylserine (PS) and phosphatidic acid (PA), and the bacterial and mitochondrial lipid cardiolipin. Typically, the gasdermin genes are expressed in epithelial and immune cells of a variety of tissues, and all are able to form pores when cleaved by an inflammatory caspase. In one example, canonical inflammasome activation activates caspase-1, which cleaves pro-IL-1β, pro-IL-18 and gasdermin D, which forms pores needed to release processed inflammatory cytokine IL-1β.

The compounds of the present disclosure efficiently block gasdermin pore formation and therefore block any of the individual downstream mediators. These compounds, therefore, are more efficient in inhibiting inflammation than anti-inflammatory agents that inhibits an individual upstream or downstream inflammatory pathway, such as those that have been clinically tested (IL-1 receptor antagonist, TNFα antibodies). The compounds are also more efficient in mediating multiple difficult-to-control dysregulatory events that kill the patient, such as disseminated intravascular coagulation (inhibited with activated protein C infusion). Inhibition of gasdermin (e.g., gasdermin D) by the compounds of the present application prevents cytokine storm. This is more effective than conventional anti-inflammatory treatments which try to reduce complications of cytokine storm once it is underway. Similarly, the compounds of the present application are also more efficient than agents that neutralize LPS or its extracellular receptors (TLR4, CD14). Since gram-bacteria elaborate many PAMPs (toxins, flagella, rod proteins), not all of which are known, neutralizing LPS may not prevent gram-sepsis, especially in humans who are LPS hypersensitive, if LPS inhibition is incomplete. TLR4 may be a less important sensor of LPS than the non-canonical inflammasome, which is constitutively expressed in humans not just in immune antigen-presenting cells, but also at mucosal epithelia. LPS is a very important trigger and if inhibiting it or its first detection is unsuccessful, then inhibiting one of the other PAMP or DAMP sensors would also be effective in, e.g., pleiotropically triggered sepsis in humans, where the triggering PAMP is generally not known at the time treatment is needed. Additionally, the compounds of the present application are also more efficient than individual inhibitors of inflammatory caspases. This is because potential cross-reactivity of these inhibitors on apoptotic caspases and other cysteine proteases might result in unwanted toxicity (e.g., liver fibrosis). Unwanted inhibition of caspase-8 can also trigger necroptosis. In some embodiments, inhibition of gasdermin pore formation occurs as a result of the compound of the present application reacting with a cysteine in a gasdermin protein. In some embodiments, the cysteine is Cys191. In some embodiments, the compound also reacts with a cysteine of an inflammatory signaling molecule selected from: a sensor, an adaptor, and a transcription factor, or a regulator thereof. In some embodiments, the compound's promiscuous reactivity with the protein cysteine residues does not result in any undesired toxicity and does not negatively affect the compound's efficacy.

In some instances, the compounds of the present application are useful in treating or preventing inflammatory disorders or ameliorating symptoms associated with these disorders. Such disorders typically result in the immune system attacking the body's own cells or tissues and include sepsis (e.g., acute sepsis), alopecia, hearing loss syndrome, gout, arthritis, rheumatoid arthritis, sclerosis, inflammatory bowel disease, ankylosing spondylitis (AS), antiphospholipid antibody syndrome (APS), myositis, scleroderma, Sjogren's syndrome, systemic lupus erythematosus, vasculitis, familial mediterranean fever, neonatal onset multisystem inflammatory disease, Behçet's disease, dermatosis, type 1 diabetes, autoimmune disease, psoriasis, psoriatic arthritis, multiple sclerosis, Addison's disease, Graves' disease, Hashimoto's thyroiditis, myasthenia gravis, pernicious anemia, celiac disease, chronic inflammation, rheumatism, encephalomyelitis, postinfectious cerebellitis, neuromyelitis optica (e.g., Devic disease), encephalitis, metabolic encephalopathy, asthma, periodontitis, ulcerative colitis, Crohn's disease, sinusitis, atherosclerosis, hypercholesterolemia, and peptic ulcer. In some instances, the inflammatory diseases include eye diseases such as glaucoma, dry eye, and retinal ischemia-reperfusion. In some instances, the inflammatory diseases include chronic lung diseases and injuries, and NASH and other inflammatory liver diseases. In some instances, in inflammatory disease is a genetic auto-inflammatory condition.

Symptoms associated with inflammatory disorders typically include chronic pain, redness, swelling of joints and other tissues, stiffness, fever, buildup of blood protein in organs, hair loss, fatigue, and damage to normal tissues. The compounds of the present application are useful in ameliorating these symptoms.

In some instances, the compounds of the present application are useful in treating sepsis, or ameliorating symptoms associated with this condition. Examples of symptoms associated with sepsis include vascular leak, circulatory collapse, coagulation activation and multiorgan failure. Without proper treatment, sepsis is fatal in about a third of cases. It is the leading cause of death of newborns and small children in the world and contributes to 1 in every 2 or 3 deaths of hospitalized adults in the US. Current treatment of sepsis is limited to antibiotics and supportive care, and over 100 clinical trials designed to quiet the immune response to infection have failed to produce a single new effective therapy. Advantageously, the compound of the present application reduce innate immune response to disseminated and poorly controlled infection and successfully treat sepsis.

In some instances, the compounds of the present application may be used for preventing sepsis, for example, in patients that are at high risk for developing sepsis. Suitable examples of such patients include neutropenic patients undergoing bone marrow transplant.

In some instances, the compounds of the present disclosure are useful in treating or preventing a cardiovascular disease. Examples of such diseases include stroke, heart failure, hypertensive heart disease, rheumatic heart disease, cardiomyopathy, heart arrhythmia, congenital heart disease, valvular heart disease, carditis, aortic aneurysms, peripheral artery disease, thromboembolic disease, coronary artery disease, myocardial infarction and venous thrombosis.

In some instances, the compounds of the present disclosure are useful in treating or preventing a metabolic disorder. Examples of such disorders include metabolic syndrome, type II diabetes, cystinosis, cystinuria, Fabry disease, galactosemia, Gaucher disease (type I), Hartnup disease, homocystinuria, Hunter syndrome, Hurler syndrome, Lesch-Nyhan syndrome, maple syrup urine disease, Maroteaux-Lamy syndrome, Morquio syndrome, Niemann-Pick disease (type A), phenylketonuria, Pompe disease, porphyria, Scheie syndrome, Tay-Sachs disease, tyrosinemia (hepatorenal), and von Gierke disease.

In some instances, the compounds of the present application are useful in treating or preventing a neurodegenerative disease. Examples of such diseases include Alzheimer's disease, Parkinson's disease, multiple sclerosis, dementia, frontotemporal dementia, Huntington's disease, Amyotrophic lateral sclerosis (ALS), motor neuron disease, and schizophrenia.

There can be an inflammatory component to any disease, especially if infection or cell death is involved in the disease. Hence, the compounds of the present application are useful in treating or preventing such disease. Suitable examples of such disease include infections caused by a Gram-positive bacteria, polymicrobial infection, infections caused by parasites (e.g., malaria, toxoplasmosis, trypanosomiasis, leishmania), transplant rejections, inflammation in the eye (e.g., retinitis, uveitis), and cancer.

Combination Treatments

In some instances, the method of using a compound described herein, or a pharmaceutically acceptable salt thereof, includes administering the compound to a subject in combination with at least one additional therapeutic agent. In this method, the compound and the additional therapeutic agent may be administered to the subject simultaneously (e.g., in the same dosage form or in separate dosage forms), or consecutively (e.g., additional therapeutic agent may be administered before or after the compound of the present disclosure, or a pharmaceutically acceptable salt thereof).

In some instances, an additional therapeutic agent includes an anti-inflammatory agent. Suitable examples include nonsteroidal anti-inflammatory drugs such as celecoxib, rofecoxib, ibuprofen, naproxen, aspirin, diclofenac, sulindac, oxaprozin, piroxicam, indomethacin, meloxicam, fenoprofen, diflunisal, BAY 11-7082, or a pharmaceutically acceptable salt thereof. Suitable examples of steroid (e.g., corticosteroid) anti-inflammatory agents include cortisol, corticosterone, hydrocortisone, aldosterone, deoxycorticosterone, triamcinolone, bardoxolone, bardoxolone methyl, triamcinolone, cortisone, prednisone, and methylprednisolone, or a pharmaceutically acceptable salt thereof. Other suitable examples of anti-inflammatory agents include proteins such as anti-inflammatory antibodies (e.g., anti-IL-1, anti-TNF), and integrins.

In some instances, an additional therapeutic agent is an antibiotic. Such an antibiotic may be selected from: a quinolone, a β-lactam, a cephalosporin, a penicillin, a carbapenem, a lipopetide, an aminoglycoside, a glycopeptide, a macrolide, an ansamycin, a sulfonamide, a monobactam, oxazolidinone, lipopeptide, macrolide, and a cationic antimicrobial peptide (CAMP).

Suitable examples of cationic antimicrobial peptides include a defensin peptide (e.g., defensin 1 such as beta-defensin 1 or alpha-defensin 1), or cecropin, andropin, moricin, ceratotoxin, melittin, magainin, dermaseptin, bombinin, brevinin (e.g., brevinin-1), esculentin, buforin II (e.g., from amphibians), CAP18 (e.g., from rabbits), LL37 (e.g., from humans), abaecin, apidaecins (e.g., from honeybees), prophenin (e.g., from pigs), indolicidin (e.g., from cattle), brevinins, protegrin (e.g., from pig), tachyplesins (e.g., from horseshoe crabs), and drosomycin (e.g., from fruit flies).

Suitable examples of quinoline antibiotics include levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, and besifloxacin.

Suitable examples of cephalosporin antibiotics include cefazolin, cefuroxime, ceftazidime, cephalexin, cephaloridine, cefamandole, cefsulodin, cefonicid, cefoperazine, cefoprozil, and ceftriaxone.

Suitable examples of penicillin antibiotics include penicillin G, penicillin V, procaine penicillin, and benzathine penicillin, ampicillin, and amoxicillin, benzylpenicillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, and pivampicillin.

Suitable examples of carbapenem antibiotics include thienamycin, tomopenem, lenapenem, tebipenem, razupenem, imipenem, meropenem, ertapenem, doripenem, panipenem (betamipron), and biapenem.

Suitable examples of lipopeptide antibiotics include polymyxin B, colistin (polymyxin E), and daptomycin.

Suitable examples of aminoglycoside antibiotics include gentamicin, amikacin, tobramycin, debekacin, kanamycin, neomycin, netilmicin, paromomycin, sisomycin, spectinomycin, and streptomycin.

Suitable examples of glycopeptide antibiotics include vancomycin, teicoplanin, telavancin, ramoplanin, daptomycin, decaplanin, and bleomycin.

Suitable examples of macrolide antibiotics include azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin and cineromycin B.

Suitable examples of ansamycin antibiotics is include streptovaricin, geldanamycin, herbimycin, rifamycin, rifampin, rifabutin, rifapentine and rifamixin.

Suitable examples of sulfonamide antibiotics include sulfanilamide, sulfacetamide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole and phthalylsulfathiazole.

Pharmaceutical Compositions

The present application also provides pharmaceutical compositions comprising an effective amount of a compound disclosed herein, or a pharmaceutically acceptable salt thereof; and a pharmaceutically acceptable carrier. The pharmaceutical composition may also comprise any one of the additional therapeutic agents described herein. In certain embodiments, the application also provides pharmaceutical compositions and dosage forms comprising any one the additional therapeutic agents described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up from the suitable pharmaceutically acceptable excipients. The contemplated compositions may contain 0.001%-100% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a compound described herein is present in an effective amount (e.g., a therapeutically effective amount).

Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, the compounds of the present application are used at concentrations that are readily and safely achieved in human blood and tissues.

In some embodiments, an effective amount of a compound of described herein can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg).

In some embodiments, an effective amount of a compound described herein is about 0.1 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg, about 90 mg/kg, about 100 mg/kg, or about 150 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

Kits

The present disclosure also provides pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit may optionally include any one of the additional therapeutic agents described herein, or a pharmaceutically acceptable salt thereof, in any one of amounts and dosage forms described herein.

Screening Assay

In some instances, the present application provides a screening assay to identify an inhibitor of, e.g., a gasdermin pore formation, inflammasome-mediated cell death (pyroptosis), cellular cytokine secretion, and/or an inflammatory caspase. Referring to FIG. 1, in such an assay, a sample may include a liposome that is formed such that a metal cation is trapped inside the liposome. The sample may also include a full-length gasdermin protein containing a protease cleavage site, a test compound, and a ligand that is capable of forming a complex with the metal cation that is trapped inside the liposome. In order to determine that the compound inhibits pore formation, a protease enzyme is added to the sample. The protease enzyme cleaves an N-terminal gasdermin fragment from the full-length gasdermin protein. In the absence of the test compound or if the test compound is inactive in the assay, these NT fragments then bind to the lipids of the liposome and form a pore in the liposome, through which the metal cation leaks out of the liposome into the external buffer. In the external buffer, the metal cation binds to the chelating ligand to form a complex. This complex has higher fluorescence than the metal cation, or the chelating ligand, when the cation and the ligand are not bound to one another. The increased fluorescence of the sample can be detected using an appropriate instrument, thus indicating leakage of the metal cation from the liposome. In the presence of an active test compound, which, for example, chemically reacts with gasdermin, the NT gasdermin fragment that is chemically modified by the test compound does not form a pore in the liposome. Hence, the metal cation remains encapsulated in the liposome and does not bind with the chelating ligand in the external buffer. As such, there is no liposome leakage and no fluorescence increase is detected in the sample. An active compound may be identified in the assay by comparing fluorescence of the sample containing the test compound and fluorescence of a control sample that does not contain any test compound. When the compound is considered active in the assay, fluorescence of the sample is lower than fluorescence of the control. In some embodiments, when the compound is considered active, fluorescence of the sample is at least about 10%, about 20%, about 30%, about 40%, about 50%, or about 60% lower than the fluorescence of the control.

In some instances, the metal cation is selected from $Ce^{3+}$, $Fe^{2+}$, $Fe^{3+}$, $Zn^{2+}$, $Cu^{2+}$, $Mg^{2+}$, and $Tb^{3+}$. In some embodiments, the metal cation is $Tb^{3+}$. In some instances, the chelating ligand is selected from ethylenediaminetetraacetic acid (EDTA), dipicolinic acid (DPA), ethylenediamine, porphyrin, and dimercaptol. In some embodiments, the chelating ligand is dipicolinic acid (DPA).

In some instances, the gasdermin protein in the sample is selected from GSDMA, GSMDB, GSDMC, GSDMD, DFNA5, and DFNB59. In some instances, the gasdermin protein contains rhinovirus 3C protease cleavage site (GSDM-3C). For example, the gasdermin protein in the sample is gasdermin D protein with a 3C protease cleavage site (GSDMD-3C).

In some instances, the protease enzyme is selected from: an inflammatory caspase and rhinovirus 3C protease. The inflammatory caspase may be caspase 1 or caspase 11. In some embodiments, the gasdermin protein is GSDM-3C and the protease enzyme is 3C protease. In other embodiments, the gasdermin protein is GSDMD-3C and the protease enzyme is 3C protease.

In yet another general aspect, the present application provides a method of identifying a compound that:

inhibits a gasdermin pore formation in a cell; and/or inhibits inflammasome-mediated death of a cell (pyroptosis); and/or inhibits cytokine secretion from a cell; and/or inhibits an inflammatory caspase in a cell; and/or covalently reacts with a cysteine of a gasdermin protein in a cell; and/or covalently reacts with a cysteine of an inflammatory signaling molecule selected from: a sensor, an adaptor, and a transcription factor, or a regulator thereof, the method comprising:

d) providing a sample comprising a liposome comprising a metal cation capable of forming a complex with a chelating ligand, the chelating ligand, and a test compound;

e) contacting the test compound with an N-terminal gasdermin protein fragment; and f) determining whether the test compound inhibits leakage of the metal cation from the liposome, wherein said inhibition of the leakage of the metal cation from the liposome is an indication that the test compound:

inhibits a gasdermin pore formation in a cell; and/or inhibits inflammasome-mediated death of a cell (pyroptosis); and/or inhibits cytokine secretion from a cell; and/or inhibits an inflammatory caspase in a cell; and/or covalently reacts with a cysteine of a gasdermin protein in a cell; and/or covalently reacts with a cysteine of an inflammatory signaling molecule selected from: a sensor, an adaptor, and a transcription factor, or a regulator thereof.

Definitions

As used herein, the term "about" means "approximately" (e.g., plus or minus approximately 10% of the indicated value).

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

The term "aromatic" refers to a carbocycle or heterocycle having one or more polyunsaturated rings having aromatic character (i.e., having (4n+2) delocalized R (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl)amino and N-isopropylamino), N-butylamino (e.g., N-(n-butyl)amino and N-(tert-butyl)amino), and the like.

As used herein, the term "di($C_{n-m}$-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —$NHS(O)_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —$S(O)_2NH_2$.

As used herein, the term "$C_{n-m}$ alkylaminosulfonyl" refers to a group of formula —$S(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —$S(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —$NHS(O)_2NH_2$.

As used herein, the term "$C_{n-m}$ alkylaminosulfonylamino" refers to a group of formula —$NHS(O)_2NH$(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —$NHS(O)_2N(alkyl)_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —$NHC(O)NH_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —$NHC(O)N(alkyl)_2$, wherein each alkyl group independently has n to m carbon atoms. In some embodiments, each alkyl group has, independently, 1 to 6, 1 to 4, or 1 to 3 carbon atoms.

As used herein, the term "carbamyl" to a group of formula —$C(O)NH_2$.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$-alkyl)carbamyl" refers to a group of formula —$C(O)N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —$S(O)_2$-alkyl, wherein the alkyl group has n to m carbon atoms. In some embodiments, the alkyl group has 1 to 6, 1 to 4, or 1 to 3 carbon atoms.

As used herein, the term "carbonyl", employed alone or in combination with other terms, refers to a —C(═O)— group, which may also be written as C(O).

As used herein, the term "carboxy" refers to a —C(O)OH group.

As used herein, the term "cyano-$C_{1-3}$ alkyl" refers to a group of formula —($C_{1-3}$ alkylene)-CN.

As used herein, the term "HO—$C_{1-3}$ alkyl" refers to a group of formula —($C_{1-3}$ alkylene)-OH.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphthyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cycloalkyl. In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropyran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

As used herein, the term "oxo" refers to an oxygen atom as a divalent substituent, forming a carbonyl group when attached to a carbon (e.g., C=O), or attached to a heteroatom forming a sulfoxide or sulfone group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, N=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the gasdermin with a compound of the invention includes the administration of a compound of the present invention to an individual or patient, such as a human, having gasdermin, as well as, for example, introducing a compound of the invention into a sample containing a cellular or purified preparation containing the gasdermin.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "preventing" or "prevention" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, preventing a disease, condition or disorder refers to decreasing the possibility of acquiring the disease, condition or disorder and/or its associated symptoms. In some embodiments, preventing a disease, condition or disorder refers to completely or almost completely stopping the disease, condition or disorder from occurring.

EXAMPLES

Cytosolic sensing of pathogens and danger by myeloid and barrier epithelial cells assembles large complexes, called inflammasomes, which activate inflammatory caspases to trigger cytokine maturation and inflammatory cell death (pyroptosis).

Inflammation recruits immune cells to orchestrate a protective immune response but can also cause pathology. Pore formation by gasdermin D (GSDMD), an inflammatory caspase substrate, was recently identified as the mechanism responsible for pyroptosis and release of inflammatory mediators. Inhibiting GSDMD is an attractive strategy to curb inflammation. The experimental results described below show that disulfiram, a drug used to treat chronic alcohol addiction, as an inhibitor of pore formation by GSDMD, but not other members of the GSDM family. Disulfiram blocks inflammasome-mediated pyroptosis and cytokine release in cells and inhibits LPS-induced septic death in mice. At nanomolar concentration, disulfiram covalently modifies human Cys191 (mouse Cys192) in GSDMD to block pore formation and pyroptosis.

General Methods

Mice. 8-week-old female C57BL/6 wild-type mice were purchased from The Jackson Laboratory and maintained at the SPF facility at Harvard Medical School. All mouse experiments were conducted using protocols approved by the Animal Care and Use Committees of Boston Children's Hospital and Harvard Medical School.

Drug administration and LPS-induced sepsis in mice. Mice were treated with disulfiram (C-23, DSF, 50 mg/kg) formulated in sesame oil or vehicle (Ctrl) by intraperitoneal injection at indicated times. In the indicated group of mice in FIG. 5*h*, copper gluconate (0.15 mg/kg) was administered intraperitoneally 6 hr prior to the first injection of DSF. Sepsis was induced in C57BL/6 mice (8-10 weeks old) by intraperitoneal injection of LPS (*E. coli* O111:B4) at indicated concentrations. In some experiments, mice were treated with copper gluconate (0.15 mg/kg) or vehicle by intraperitoneal injection 5 hr before LPS challenge and then given DSF (50 mg/kg) intraperitoneally dissolved in sesame oil or vehicle 4 hr before and just before LPS challenge (15 mg/kg intraperitoneally). Peritoneal cells were collected by rinsing the peritoneal cavity with ice cold PBS containing 3% FBS 6 hr after LPS challenge. To measure cytokines, blood samples were collected by tail vein bleed 12 hr post LPS challenge and allowed to clot at room temperature. Sera obtained after centrifugation at 2,000×g for 10 min were analysed for inflammatory cytokines by ELISA.

Reagents. β-mercaptoethanol (2ME), dithiothreitol (DTT), terbium(III) chloride (TbCl3), dipicolinic acid (DPA) and copper gluconate were from Sigma-Aldrich. Compound C-23 and its analogues: Tetraethylthiuram disulfide (C-23), tetramethylthiuram disulfide (C-23A1), tetrabutylthiuram disulfide (C-23A3), 4-Methylpiperazine-1-carbothioic dithioperoxyanhydride (C-23A4), Tetraphenylthiuram disulfide (C-23A5), N,N'-Dimethyl-N,N'-(4,4'-dimethyldiphenyl)thiuram disulfide (C-23A6), di(4-morpholinyl)dithioperoxyanhydride (C-23A7), N,N'-Dimethyl-N,N'-di(4-pyridinyl)thiuram disulfide (C-23A8), pyrrolidine-1-carbothioic dithioperoxyanhydride (C-23A10), and dimethyldiphenylthiuram disulfide (C-23A11) were from Sigma-Aldrich. Tetraisopropylthiuram disulfide (C-23A2) and dicyclopentamethylenethiuram disulfide (C-23A9) were from Oakwood Chemicals. Tetrabenzylthiuram disulfide (C-23A12) was from AK Scientific. Phorbol 12-myristate 13-acetate (PMA) and DMSO were from Sigma-Aldrich. Ultra LPS and nigericin were from InvivoGen. The pan-caspase inhibitor z-VAD-fmk was from BD Bioscience. The complete protease inhibitor cocktail and the PhosSTOP phosphatase inhibitor cocktail were from Roche. Necrosulfonamide, Necrostatin-1, dimethyl fumarate, ibrutinib and afatinib were from Sigma-Aldrich. LDC7559 was synthesized by Intonation Research Labs.

Biomolecules: The monoclonal antibody against GSDMD was generated in house by immunizing 6 week-old BALB/c mice with recombinant human GSDMD and boosting with recombinant human GSDMD-NT according to standard protocols. Serum samples were collected to assess titers of reactive antibodies and spleen cells were fused with SP2/0 myeloma cells. Hybridomas were selected and supernatants from the resulting clones were screened by enzyme linked immunosorbent assay (ELISA), immunoblot and immunofluorescence microscopy. Tubulin antibody was from Sigma-Aldrich. Phospho-IκBα antibody, IκBα antibody, Phospho-NF-κB p65 antibody, cleaved human caspase-1 (Asp297) antibody and NLRP3 antibody were from Cell Signaling Technology. ASC antibody (AL177) and mouse caspase-1 p20 antibody were from AdipoGen. Human and mouse IL-1β antibodies were from R&D Systems. HMGB1 and mouse GSDMD antibodies were from Abcam.

Liposome leakage assay: fluorogenic liposome leakage assay detects leakage of $Tb^{3+}$ from $Tb^{3+}$-loaded liposomes incubated with GSDMD and caspase-11 (See References 7 and 9). See FIG. 1. Liposome leakage was detected by an increase in fluorescence when $Tb^{3+}$ bound to dipicolinic acid (DPA) in Buffer C. Human GSDMD (0.3 μM) was dispensed into a well (Corning 3820) containing PC/PE/CL liposomes (50 μM liposome lipids) and incubated with a test compound for 1 hr before addition of caspase-11 (0.15 μM) to each well. The fluorescence intensity of the well was measured at 545 nm with an excitation of 276 nm 1 hr after addition of caspase-11 using a Perkin Elmer EnVision plate reader. The final percent inhibition was calculated as $[(\text{fluorescence}_{test\ compound}-\text{fluorescence}_{negative\ control})/(\text{fluorescence}_{positive\ control}-\text{fluorescence}_{negative\ control})]\times 100$, where a well with GSDMD without the test compound was used as positive control, and a well without caspase-11 was used as negative control. $IC_{50}$ of the test compound was determined in concentration-response experiments in a dose range of 0.008-50 μM.

Protein expression and purification: full-length human GSDMD sequence was cloned into the pDB.His.MBP vector with a tobacco etch virus (TEV)-cleavable N-terminal $His_6$-MBP tag using NdeI and XhoI restriction sites. Human GSDMD-3C and mouse GSDMA3-3C mutants were constructed by QuikChange Mutagenesis (Agilent Technologies). For expression of full-length GSDMD, GSDMD-3C, GSDMA3, and GSDMA3-3C, *E. coli* BL21 (DE3) cells harbouring the indicated plasmids were grown at 18° C. overnight in LB medium supplemented with 50 μg $ml^{-1}$ kanamycin after induction with 0.5 mM isopropyl-β-D-thiogalactopyranoside (IPTG) when $OD_{600}$ reached 0.8. Cells were ultrasonicated in lysis buffer containing 25 mM Tris-HCl at pH 8.0, 150 mM NaCl, 20 mM imidazole and 5 mM 2ME. The lysate was clarified by centrifugation at 40,000×g at 4° C. for 1 hr. The supernatant containing the target protein was incubated with Ni-NTA resin (Qiagen) for 30 min at 4° C. After incubation, the resin-supernatant mixture was poured into a column and the resin was washed with lysis buffer. The protein was eluted using the lysis buffer supplemented with 100 mM imidazole. The $His_6$-MBP tag was removed by overnight TEV protease digestion at 16° C. The cleaved protein was purified using HiTrap Q ion-exchange and Superdex 200 gel-filtration columns (GE Healthcare Life Sciences).

Caspase-11 sequence was cloned into the pFastBac-HTa vector with a TEV cleavable N-terminal $His_6$-tag using EcoRI and XhoI restriction sites. The baculoviruses were prepared using the Bac-to-Bac system (Invitrogen), and the protein was expressed in Sf9 cells following the manufacturer's instructions. His-caspase-11 baculovirus (10 ml) was used to infect 1 L of Sf9 cells. Cells were collected 48 hrs after infection and $His_6$-caspase-11 was purified following the same protocol as for $His_6$-MBP-GSDMD. Eluate from Ni-NTA resin was collected for subsequent assays.

Liposome preparation: PC (1-palmitoyl-2-oleoyl-sn-glycero-3-phosphocholine, 25 mg/mL in chloroform; 80 μL), PE (1-palmitoyl-2-oleoyl-sn-glycero-3-phosphoethanolamine, 25 mg/mL in chloroform; 128 μL) and CL (1',3'-bis[1,2-dioleoyl-sn-glycero-3-phospho]-sn-glycerol (sodium salt), 25 mg/mL in chloroform; 64 μL) were mixed and the solvent was evaporated under a stream of $N_2$ gas. The lipid mixture was suspended in 1 mL Buffer A (20 mM HEPES, 150 mM NaCl, 50 mM sodium citrate, and 15 mM TbCl3) for 3 min. The suspension was pushed through 100 nm Whatman® Nuclepore™ Track-Etched Membrane 30 times to obtain homogeneous liposomes. The filtered suspension was purified by size exclusion column (Superose 6, 10/300 GL) in Buffer B (20 mM HEPES, 150 mM NaCl) to remove $TbCl_3$ outside liposomes. Void fractions were pooled to produce a stock of PC/PE/CL liposomes (1.6 mM). The liposomes are diluted to 50 μM with Buffer C (20 mM HEPES, 150 mM NaCl and 50 μM DPA) for use in high-throughput screening.

Fluorescent protein labelling and microscale thermophoresis binding assay: $His_6$-MBP-GSDMD was labeled with AlexaFluor-488 using the Molecular Probes protein labelling kit. Binding of inhibitors to GSDMD was evaluated using microscale thermophoresis (MST). Ligands (49 nM-150 μM) were incubated with purified AlexaFluor-488-labeled protein (80 nM) for 30 min in assay buffer (20 mM HEPES, 150 mM NaCl, 0.05% Tween 20). The sample was loaded into NanoTemper Monolith NT.115 glass capillaries and MST carried out using 20% LED power and 40% MST power. $K_d$ values were calculated using the mass action equation and NanoTemper software.

Caspase-1 and caspase-11 inhibition assays: the fluorogenic assay for caspase-1 and caspase-11 activity is based on release of 7-amino-4-methylcoumarin (AMC) from the caspase substrate Ac-YVAD-AMC. Compounds (8 nM-50 μM) were incubated with 0.5 U of caspase-1 or caspase-11 for 30 min in assay buffer (20 mM HEPES, 150 mM NaCl) in 384-well plates (Corning 3820) before addition of Ac-YVAD-AMC (40 μM) to initiate the reactions. Reactions were monitored in a SpectraMax M5 plate reader (Molecular Devices, Sunnyvale, California USA) with excitation/emission wavelengths at 350/460 nm. The fluorescence intensity of each reaction was recorded every 2 min for 2 hrs.

Cell viability assay. THP-1 cells seeded at a density of 4000 cells per well in 96-well plates (Corning 3610), were differentiated by exposure to 50 nM PMA for 36 hrs before being primed with 100 ng/mL LPS. Primed THP-1 cells were pretreated with each test compound for 1 hr before addition of 20 μM nigericin or medium as control. The number of surviving cells was determined by CellTiter-Glo assay 1.5 hrs later. The final percent cell viability was calculated using the formula [$(\text{luminescence}_{test\ compound}-\text{luminescence}_{negative\ control})/(\text{luminescence}_{positive\ control}-\text{luminescence}_{negative\ control})$]×100, where wells with only LPS were used as positive controls and wells treated with LPS and nigericin were used as negative controls. The $IC_{50}$ of each test compound in the cell viability assay was determined by concentration-response experiments in a dose range of 0.39-50 μM.

Mass spectrometry and sample preparation. Gel bands were cut into 1 mm size pieces and placed into separate 1.5 mL polypropylene tubes. 100 μl of 50% acetonitrile in 50 mM ammonium bicarbonate buffer were added to each tube and the samples were then incubated at room temperature for 20 min. This step was repeated if necessary to destain gel. Then, the gel slice was incubated with 55 mM iodoacetamide (in 50 mM ammonium bicarbonate) for 45 min in the dark at room temperature, before the gel was washed sequentially with 50 mM ammonium bicarbonate, water and acetonitrile. Samples were then dried in a Speedvac for 20 min. Trypsin (Promega Corp.) (10 ng/μL in 25 mM ammonium bicarbonate, pH 8.0) was added to each sample tube to just cover the gel, and samples were then incubated at 37° C. for 6 hrs or overnight.

After digestion, samples were acidified with 0.1% formic acid (FA) and 3 μl of tryptic peptide solution was injected. Nano-LC/MS/MS was performed on a Thermo Scientific Orbitrap Fusion system, coupled with a Dionex Ultimat 3000 nano HPLC and auto sampler with 40 well standard trays. Samples were injected onto a trap column (300 μm i.d.×5 mm, C18 PepMap 100) and then onto a C18 reversed-phase nano LC column (Acclaim PepMap 100 75 μm×25 cm), heated to 50° C. Flow rate was set to 400 nL/min with 60 min LC gradient, using mobile phases A (99.9% water, 0.1% FA) and B (99.9% acetonitrile, 0.1% FA). Eluted peptides were sprayed through a charged emitter tip (PicoTip Emitter, New Objective, 10+/−1 μm) into the mass spectrometer. Parameters were: tip voltage, +2.2 kV; Fourier Transform Mass Spectrometry (FTMS) mode for MS acquisition of precursor ions (resolution 120,000); Ion Trap Mass Spectrometry (ITMS) mode for subsequent MS/MS via higher-energy collisional dissociation (HCD) on top speed in 3 s.

Proteome Discoverer 1.4 was used for protein identification and modification analysis. UniPort human database was used to analyze raw data. Other parameters include the following: selecting the enzyme as trypsin; maximum missed cleavages=2; dynamic modifications are carbamidomethyl (control), diethyldithiocarbamate (from C-23) and Bay 11-7082 on cysteine; oxidized methionine, deaminated asparagine and glutamine; precursor tolerance set at 10 ppm; MS/MS fragment tolerance set at 0.6 Da; and +2 to +4 charged peptides are considered. Peptide false discovery rate (FDR) was set to be smaller than 1% for significant match.

Cell lines and treatments: THP-1 cells and HEK293T cells (obtained from ATCC) were grown in RPMI with 10% heat-inactivated fetal bovine serum, supplemented with 100 U/ml penicillin G, 100 μg/ml streptomycin sulfate, 6 mM HEPES, 1.6 mM L-glutamine, and 50 μM 2ME. C57BL/6 mouse iBMDM cells were kindly provided by J. Kagan (Boston Children's Hospital) and cultured in DMEM with the same supplements. Cells were verified to be free of *mycoplasma* contamination. Transient transfection of HEK293T cells was performed using Lipofectamine 2000 (Invitrogen) according to the manufacturer's instructions. iBMDM cells were transfected by nucleofection using the Amaxa Nucleofector kit (VPA-1009). Generally, THP-1 cells were first differentiated by incubation with 50 nM PMA for 36 hrs and then primed with LPS (1 μg/ml) for 4 hrs before treatment with nigericin (20 μM). To examine IrBu phosphorylation and degradation as well as IL-1β induction, PMA-differentiated THP-1 cells were stimulated with LPS (1 μg/ml) for 0.5, 1 and 4 hrs, respectively. For noncanoical inflammasome activation, 1 million iBMDM cells were electroporated with 1 μg ultra LPS.

Cytotoxicity and cell viability assays: cell death and cell viability were determined by the lactate dehydrogenase release assay using the CytoTox 96 Non-Radioactive Cytotoxicity Assay kit (Promega) and by measuring ATP levels using the CellTiter-Glo Luminescent Cell Viability Assay (Promega), respectively, according to the manufacturer's instructions. Luminescence and absorbance were measured on a BioTek Synergy 2 plate reader.

Pore reconstitution on nanodiscs and negative staining electron microscopy: the coding sequence of the membrane scaffold protein NW50 was cloned into a pET-28a vector, and the protein was expressed in *E. coli* BL21(DE3), purified via a refolding procedure, and covalently circularized with sortase according to a previously described protocol. A lipid mixture containing phosphatidylserine (PS) and phosphatidylcholine (PC) (molar ratio 3:7) was solubilized in 60 mM sodium cholate and incubated with circularized NW50 on ice for 1 h to assemble nanodiscs. Sodium cholate was then removed by incubation overnight at 4° C. with Bio-beads SM-2 (Bio-Rad). The Bio-beads were then removed using a 0.22 μm filter, and the assembled nanodiscs were further purified using a Superose 6 10/300 gel-filtration column (GE Healthcare Life Sciences) equilibrated with Buffer D (50 mM Tris-HCl at pH 8.0, 150 mM NaCl) to remove excess lipids. To form GSDMD pores on the nanodiscs, purified human GSDMD-3C was incubated with 3C protease in the presence of nanodiscs for 6 hrs on ice. The pores were further purified over a Superose 6 column equilibrated with Buffer D. To assess the effect of C-23, human GSDMD-3C plus 3C protease was either incubated with C-23 (molar ratio 1:1) for 30 min on ice before adding to nanodiscs (pretreatment), or C-23 was added for 30 min on ice to already assembled pores (post-treatment). For negative staining electron microscopy, a 5-μl sample was placed onto a glow-discharged carbon-coated copper grid (Electron Microscopy Sciences), washed twice with Buffer A, stained with 1% uranyl formate for 1 min, and air-dried. The grids were imaged on the Tecnai $G^2$ Spirit BioTWIN electron microscope and recorded with an AMT 2k CCD camera (Harvard Medical School Electron Microscopy Facility).

Immunoblot analysis: cell extracts were prepared using RIPA buffer (50 mM Tris-HCl pH 7.4, 150 mM NaCl, 1 mM EDTA, 1% Triton X-100, 0.1% SDS, 0.5% deoxycholate) supplemented with a complete protease inhibitor cocktail (Roche) and a PhosSTOP phosphatase inhibitor cocktail (Roche). Samples were subjected to SDS-PAGE and the resolved proteins were then transferred to a PVDF membrane (Millipore). Immunoblots were probed with indicated antibodies and visualized using a SuperSignal West Pico chemiluminescence ECL kit (Pierce).

Caspase-1 activity assay in cells: to measure caspase-1 activation, THP-1 cells were seeded into 96-well plates and differentiated with PMA. After the indicated treatments, cells were incubated with a fluorescent active caspase-1 substrate FAM-YVAD-FMK (Immunochemistry Technologies). Samples were read on a BioTek Synergy 2 plate reader.

Measurement of cytokines: concentrations of IL-1β in culture supernatants or mouse serum were measured by ELISA kit (R&D Systems) according to the manufacturer's instructions.

Immunostaining and confocal microscopy: cells grown on coverslips were fixed for 15 min with 4% paraformaldehyde in PBS, permeabilized for 5 min in 0.1% Triton X-100 in PBS and blocked using 5% BSA for 1 hr. Then, cells were stained with the indicated primary antibodies followed by incubation with fluorescent-conjugated secondary antibodies (Jackson ImmunoResearch). Nuclei were counterstained with DAPI (4,6-diamidino-2-phenylindole) (Sigma-Aldrich). Slides were mounted using Aqua-Poly/Mount (Dako). Images were captured using a laser scanning confocal microscope (Olympus Fluoview FV1000 Confocal System) with a 63× water immersion objective and Olympus Fluoview software (Olympus). All confocal images are representative of three independent experiments.

Statistics: student's t-test was used for the statistical analysis of two independent treatments. Mouse survival curves and statistics were analyzed using the Mantel-Cox Log-rank test.

Example 1—Inhibition of GSDMD Pore Formation by the Test Compounds

C-23 is a symmetrical molecule known as disulfiram, a drug used to treat alcohol addiction (See Reference 12):

(C-23)

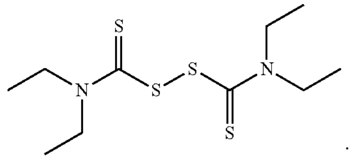

$IC_{50}$ values and GSDMD binding results for the test compounds (assessed by microscale thermophoresis (MST)) are presented in Table 1. Chemical structures of the tested compounds are shown in FIG. 11.

TABLE 1

| compound | In vitro $IC_{50}$ (μM) | Binding $K_D$ by MST (μM) |
|---|---|---|
| C-5 | 1.1 ± 0.4 | |
| C-7 | 1.9 ± 0.1 | |
| C-8 | 2.4 ± 0.3 | |
| C-22 | 1.6 ± 0.3 | 27.9 ± 5.5 |
| C-23 | 0.3 ± 0.0 | 12.8 ± 1.9 |
| C-24 | 0.6 ± 0.1 | 8.6 ± 0.6 |
| C-25 | 1.8 ± 0.6 | |

Figure 3:
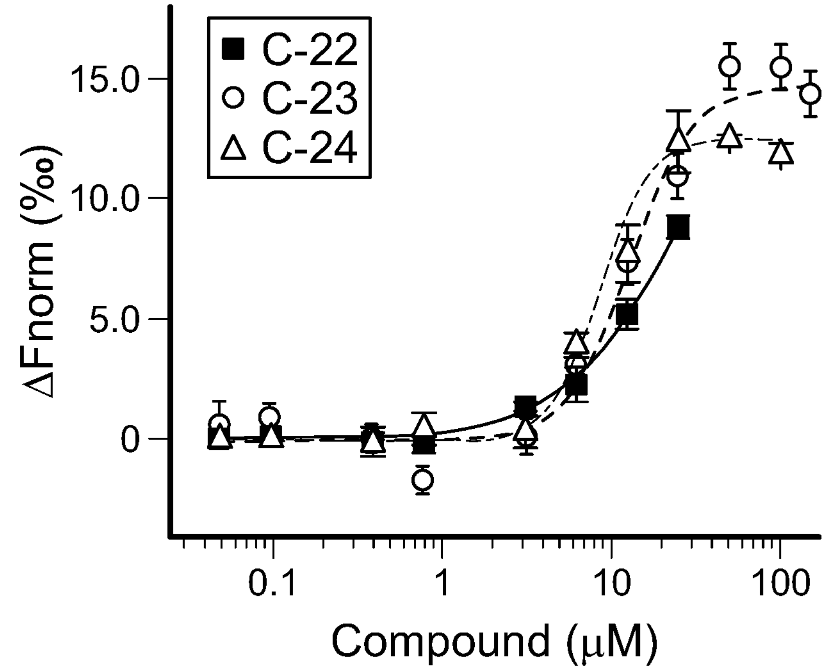
FIG. 3 contains line plot showing MST measurement of the binding of Alexa 488-labeled His-MBP-GSDMD (80 nM) with C-22, C-23 or C-24.

The test compounds were assessed for GSDMD binding by microscale thermophoresis (MST). FIG. 3 shows MST measurement of the binding of Alexa 488-labeled His-MBP-GSDMD (80 nM) with C-22, C-23 or C-24.

To evaluate whether test compounds inhibit pyroptosis, test compounds were added to PMA-differentiated and LPS-primed human THP-1 cells or mouse immortalized bone marrow-derived macrophages (iBMDMs) before activating the canonical inflammasome with nigericin or the non-canonical inflammasome by LPS electroporation. As discussed in the following paragraph, C-23 blocked pyroptosis in cells, with $IC_{50}$ values of 7.67±0.29 μM and 10.33±0.50 μM for canonical and non-canonical inflammasome-dependent pyroptosis, respectively, and impaired cell death triggered by the AIM2 inflammasome in mouse iBMDMs transfected with poly(dA:dT) (See FIG. 10). Disulfiram also inhibited nigericin- or LPS transfection-induced IL-1β secretion with potency comparable to the pan-caspase inhibitor z-VAD-fmk.

Figure 2:
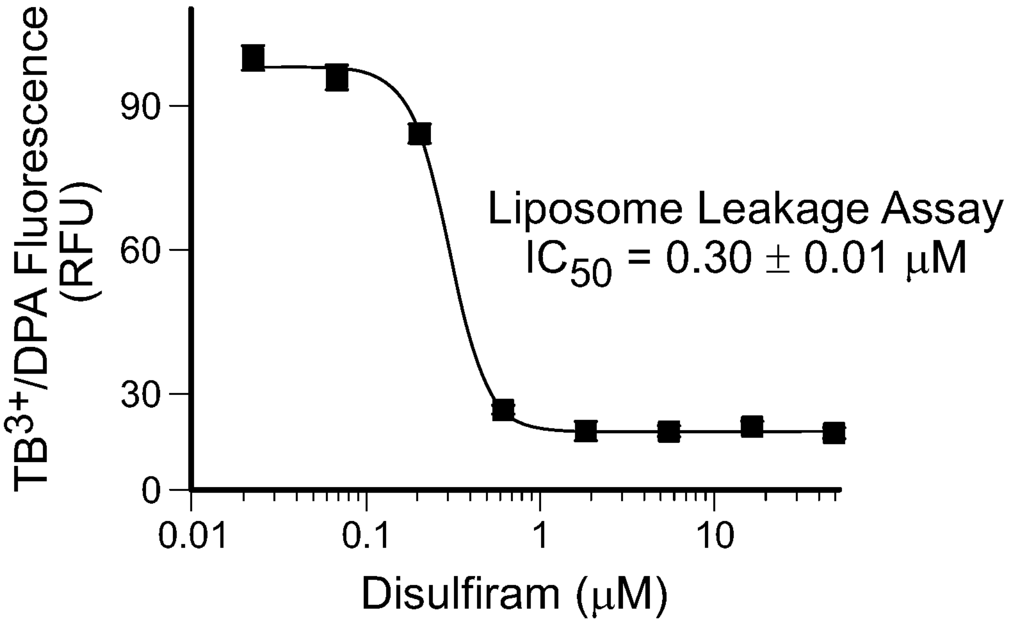
FIG. 2 contains a line plot showing a dose response curve of disulfiram in liposome leakage assay.
Figure 4:
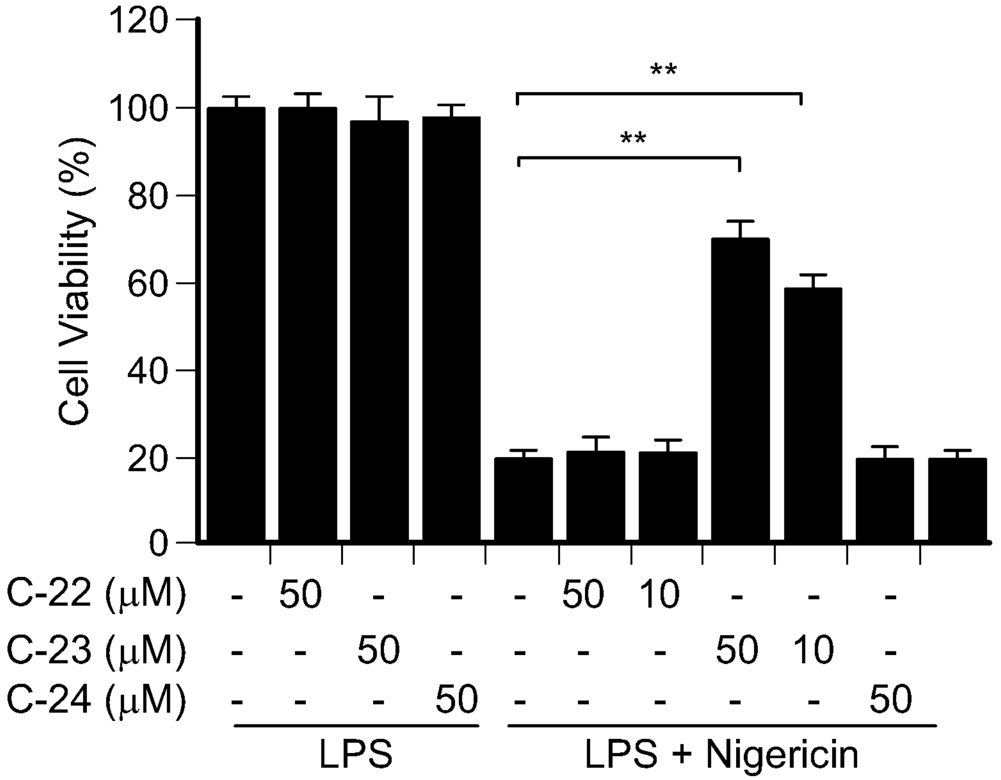
FIG. 4 contains a bar graph showing cell viability after treatment with compounds C-22, C-23, and C-24 in the presence of nigericin or medium.
Figure 5:
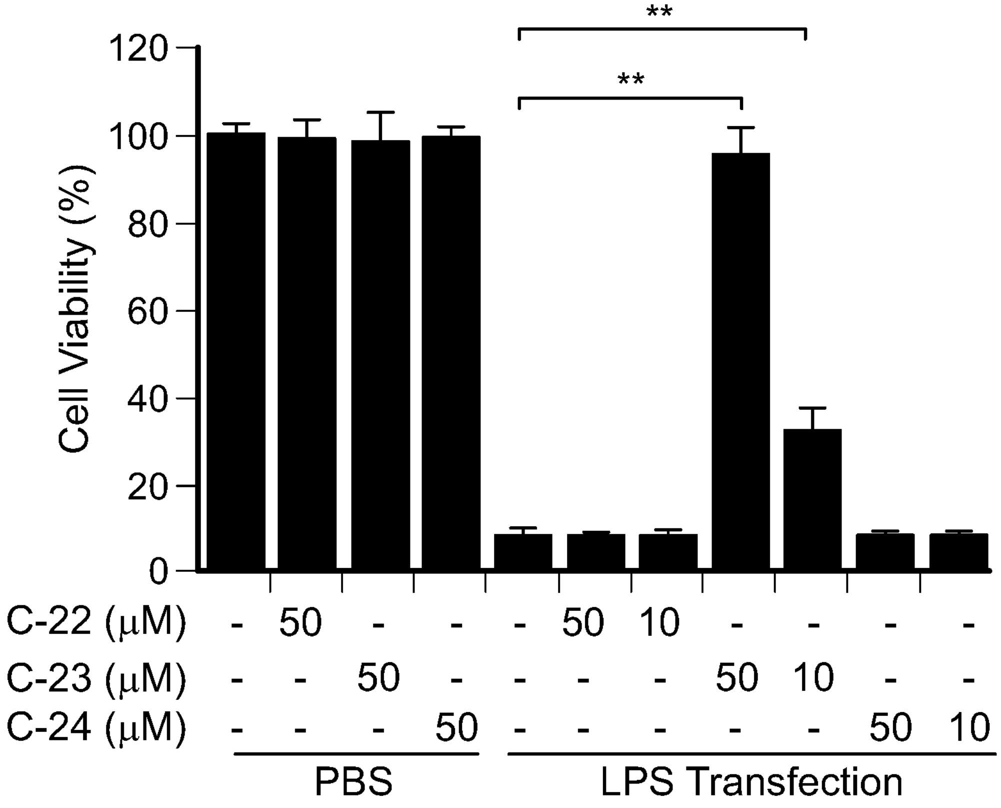
FIG. 5 contains a bar graph showing cell viability after pretreatment with each test compound (before electroporation with PBS or LPS).
Figure 6:
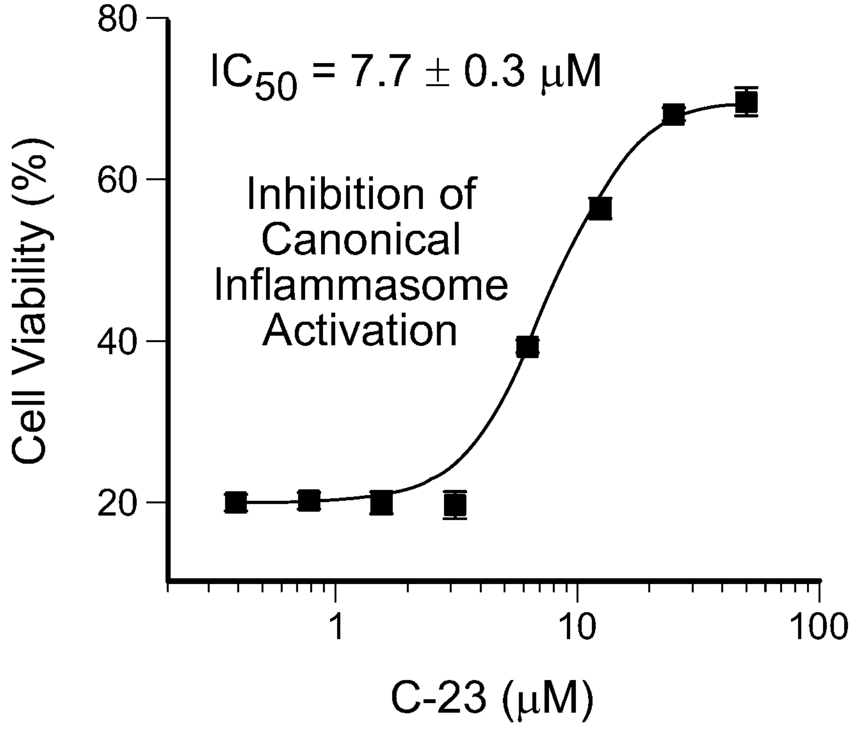
FIG. 6 contains a line plot showing $IC_{50}$ of inhibition by compound C-23 of canonical inflammasome activation.
Figure 7:
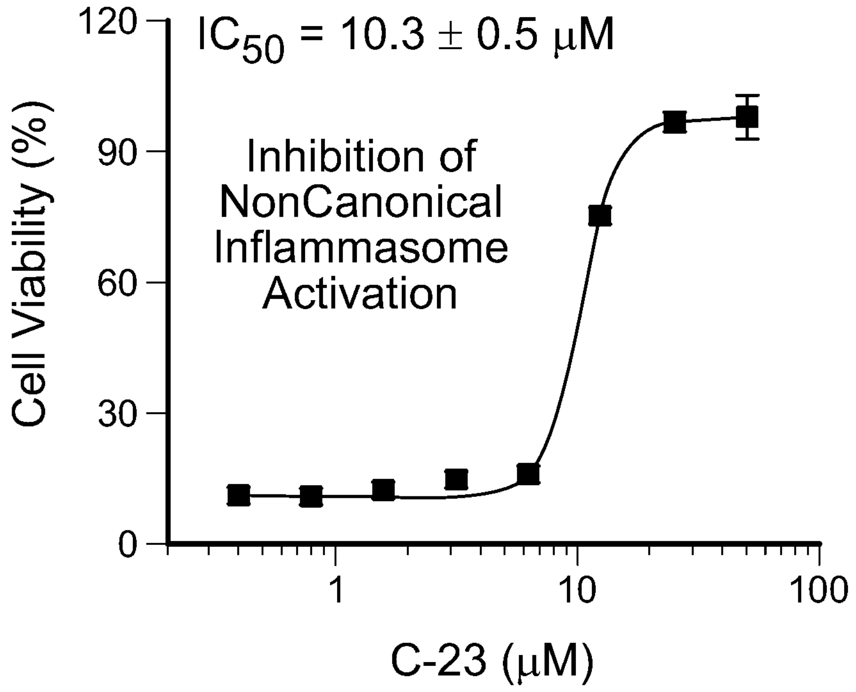
FIG. 7 contains a line plot showing $IC_{50}$ of inhibition by compound C-23 of non-canonical inflammasome activation.
Figure 8:
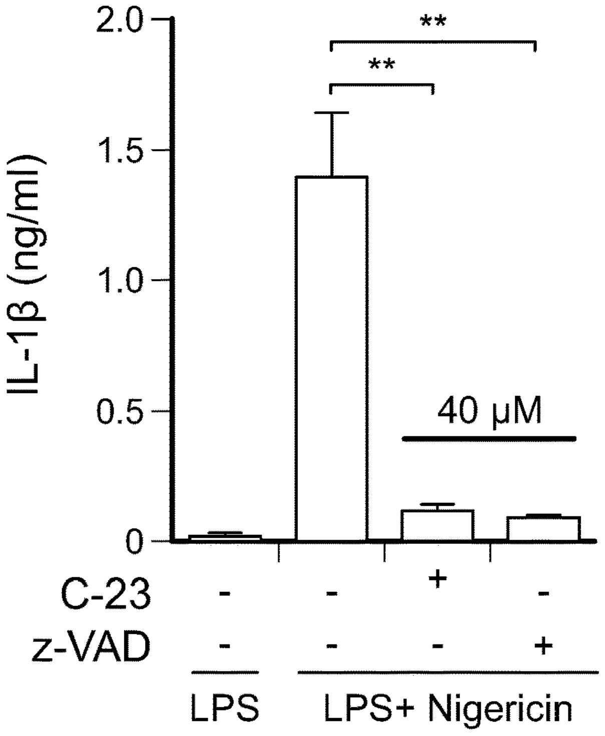
FIG. 8 contains a bar graph showing levels of IL-1β in culture supernatants treated by compound C-23 as assessed by ELISA (cells treated with LPS, or LPS and nigericin).
Figure 9:
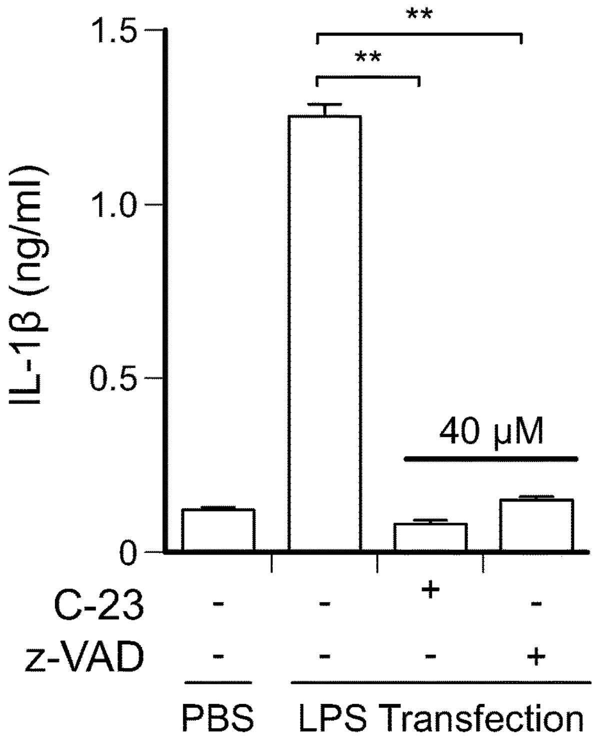
FIG. 9 contains a bar graph showing levels of IL-1β in culture supernatants treated by compound C-23 as assessed by ELISA (cells treated with PBS, or LPS transfection).
Figure 40:
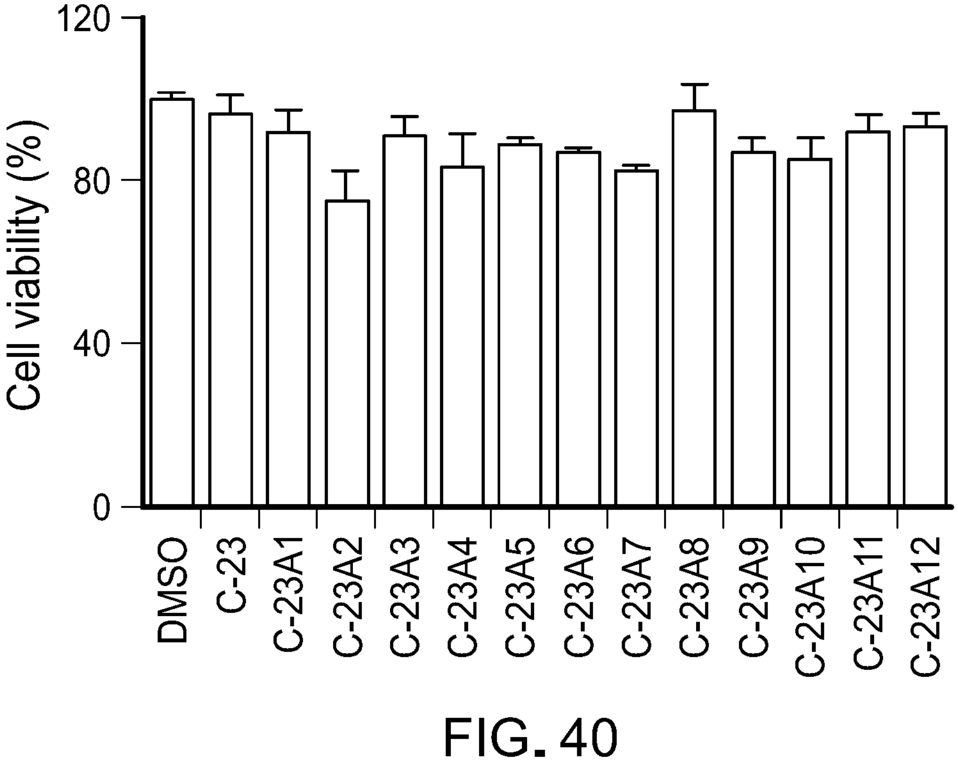
FIG. 40 contains a bar graph showing results of cell viability assay for the compounds presented in Table 2 and FIG. 39.

Experimental results: response curve of compound disulfiram (C-23) in liposome leakage assay is shown in FIG. 2. In FIGS. 4, 6, and 8, PMA-differentiated LPS-primed human THP-1 were pre-treated with indicated concentrations of each compound for 1 h before adding nigericin or medium. The number of surviving cells was determined by CellTiter-Glo assay (FIGS. 4 and 6) and IL-1β in culture supernatants was assessed by ELISA (FIG. 8) 2 hrs later. In FIGS. 5, 7, and 9, mouse iBMDMs were pre-treated with each test compound for 1 hr before electroporation with PBS or LPS. The number of surviving cells was determined by CellTiter-Glo assay (FIGS. 5 and 7) and IL-1β in culture supernatants was assessed by ELISA (FIG. 9) 2.5 hrs later. In FIGS. 8 and 9, 40 μM concentration of test compounds were added. In FIG. 10, mouse iBMDMs were pre-treated or not with 30 μM of C-23 for 1 h before transfection with PBS or poly(dA:dT) and analyzed for cell viability by CellTiter-Glo assay 4 h later. Graphs show the mean±s.d. and data shown are representative of three independent experiments. **P<0.01.

To confirm that C-23 inhibits pore formation, we reconstituted human GSDMD-NT pores on covalently circularized lipid nanodiscs constructed with phosphatidyl serine (PS), an acidic lipid, and phosphatidyl choline. Full-length GSDMD was engineered to replace the caspase cleavage site with a rhinovirus 3C protease cleavage site (GSDMD-3C) as previously described. 3C protease cleavage of the engineered GSDMD-3C liberates an active NT fragment. Adding GSDMD-3C plus 3C protease to assembled nanodiscs reconstituted pores that were visible by negative staining electron microscopy (EM). When pretreated with C-23 before being added to the nanodiscs, pore formation by GSDMD-3C plus 3C protease was completely blocked. However, C-23 addition after pore formation did not disrupt already assembled pores. Thus, disulfiram inhibits pore formation, but does not disassemble already formed pores.

To evaluate whether C-22, -23, and -24 inhibit pyroptosis, these compounds were added to PMA-differentiated and LPS-primed human THP-1 cells before activating the canonical NLRP3 inflammasome with nigericin or to mouse immortalized bone marrow-derived macrophages (iBMDMs) before activating the non-canonical inflammasome by LPS electroporation (See Figures). Only C-23 blocked pyroptosis, with similar $IC_{50}$ values of 7.7±0.3 μM and 10.3±0.5 μM for canonical human and non-canonical mouse inflammasome-dependent pyroptosis, respectively. It also impaired cell death in a dose-dependent manner triggered by the AIM2 inflammasome in mouse iBMDMs transfected with poly(dA:dT), supporting its inhibition of the common downstream portion of inflammasome pathways. Inhibition was shown by cell survival, assessed by CellTiter-Glo ATP luminescence, and membrane permeabilization, assessed by uptake of the membrane-impermeable dye SYTOX Green. In addition, disulfiram inhibited nigericin-induced IL-1β secretion in THP-1 and LPS transfection-induced IL-1β secretion in iBMDM cells with potency comparable to the pan-caspase inhibitor z-VAD-fmk. In contrast, disulfiram had no effect on necroptosis induced in HT-29 cells by treatment with TNFα, SMAC mimetic, and z-VAD-fmk, which was blocked by either necrosulfonamide (NSA) or necrostatin-1 (Nec). These data show that disulfiram inhibits pyroptosis in both human and mouse cells triggered by canonical and non-canonical inflammasomes, but not necroptosis.

Example 2—Disulfiram Protects Against LPS-Induced Sepsis

Disulfiram is being investigated as an anticancer agent because epidemiological studies showed that individuals taking disulfiram for alcohol addiction were less likely to die of cancer (See Reference 24). In cells disulfiram is rapidly metabolized to diethyldithiocarbamate (DTC) (See Reference 25 and 26):

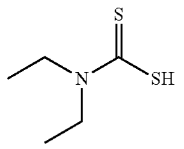

Figure 13:
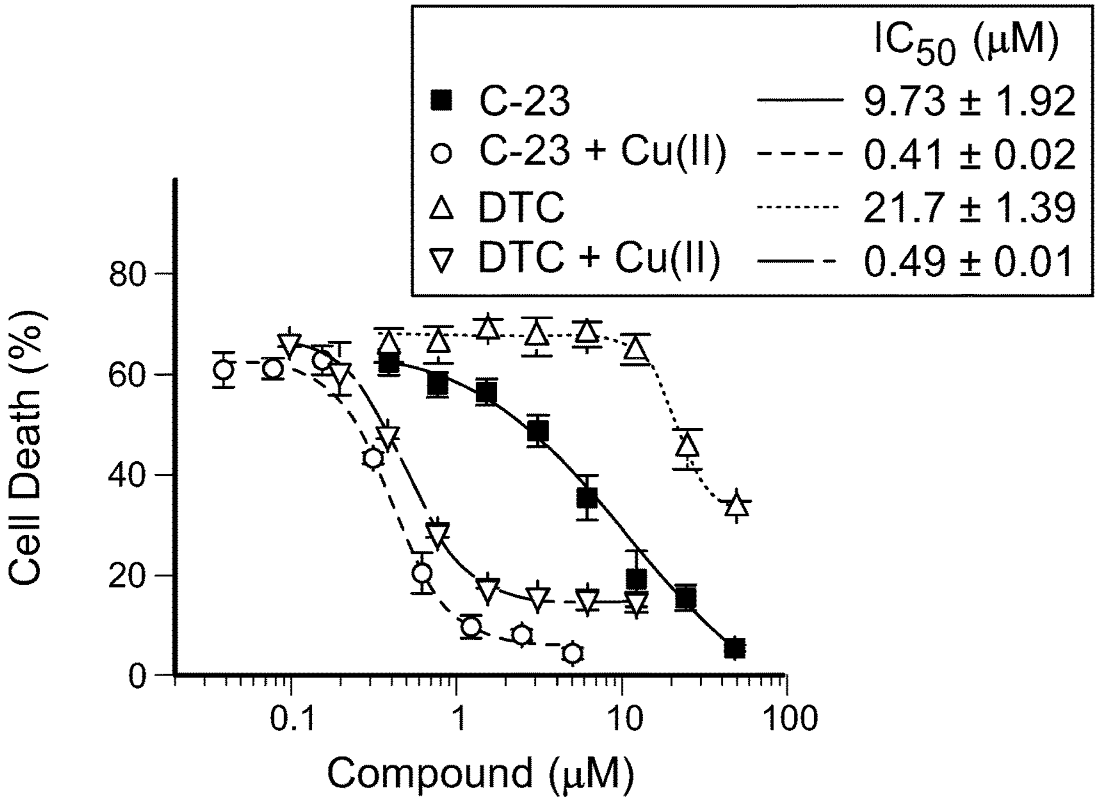
FIG. 13 contains line plots showing that LPS-primed THP-1 were pretreated with C-23 or DTC in the presence or absence of Cu(II) for 1 hr before adding nigericin or medium for 2 hrs.

The anti-cancer activity of DTC in vivo is greatly enhanced by complexation with copper (See, e.g., Reference 24), likely because of the enhanced electrophilicity of the DTC thiols. In liposome leakage assay, it was found that copper gluconate ($Cu^{2+}$) only weakly increased disulfiram or DTC inhibition. This is likely due to the high reactivity of the GSDMD Cys residue involved (see the following Example). However, $Cu^{2+}$ strongly promoted the ability of either disulfiram or DTC to protect LPS-primed THP-1 cells from pyroptosis (FIG. 13). With $Cu^{2+}$, the $IC_{50}$ of C-23 for inhibiting pyroptosis decreased 24-fold to 0.41±0.02 μM, which was similar to its potency for preventing liposome leakage. DTC became almost as active as C-23 in cells in the presence of $Cu^{2+}$.

Figure 14:
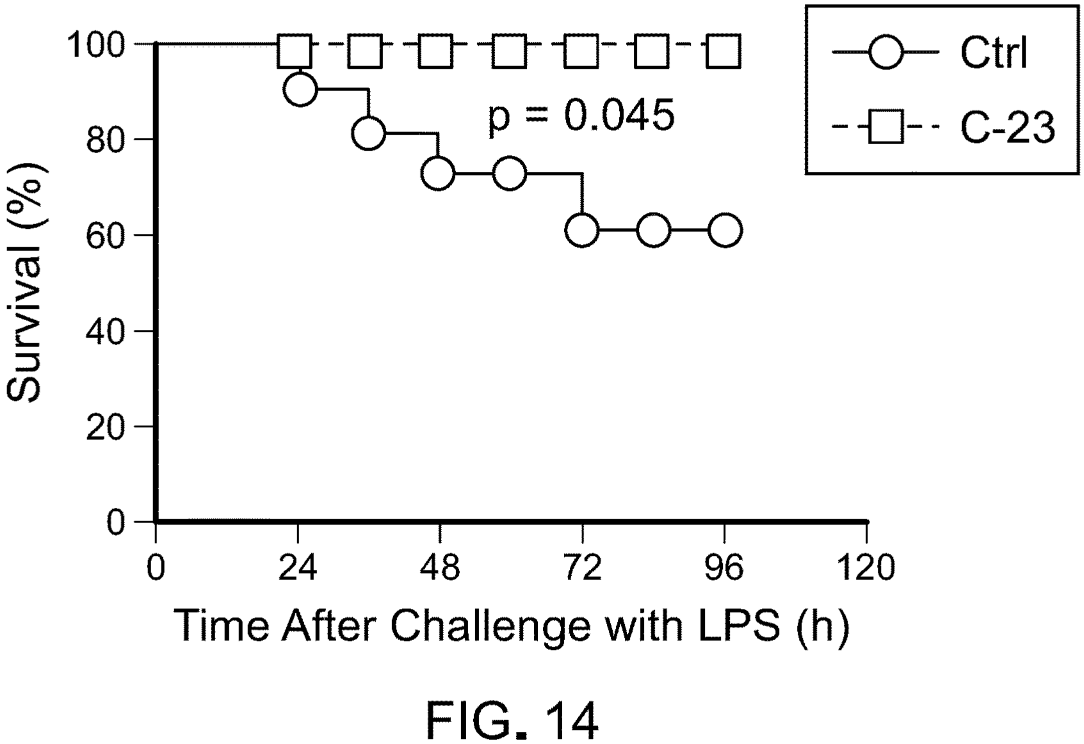
FIG. 14 contains line plots showing % mice survival after challenge with 15 mg/kg of LPS and treatment with C-23.
Figure 15:
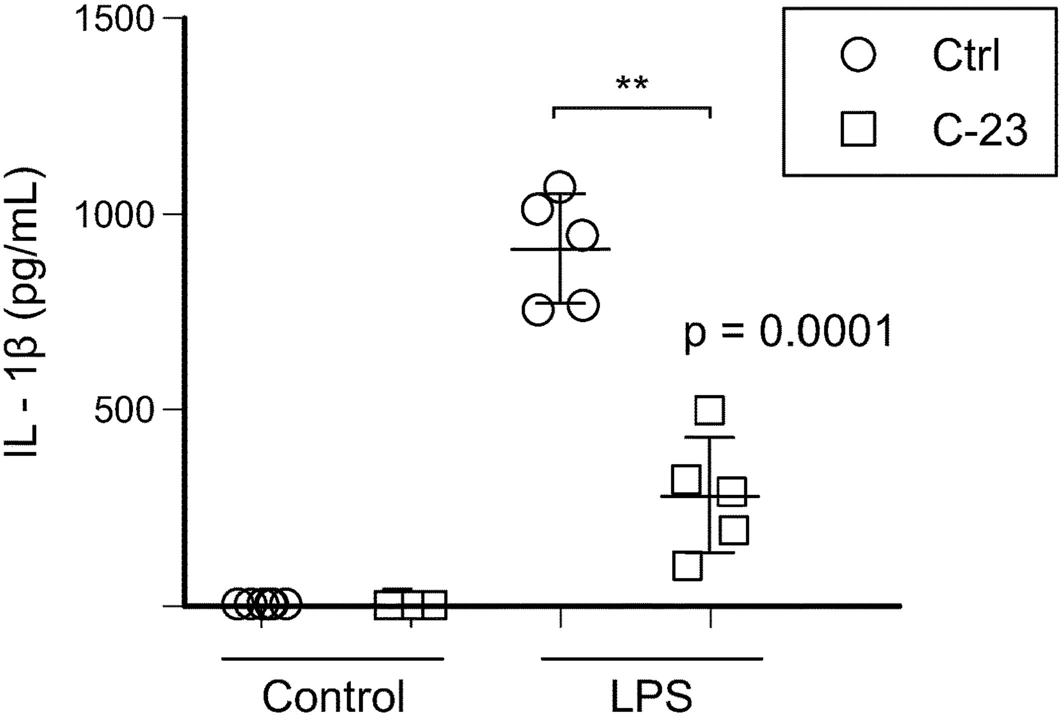
FIG. 15 contains a bar graph showing serum IL-1β measured by ELISA in mice pretreated with C-23 and challenged with 15 mg/kg LPS.
Figure 16:
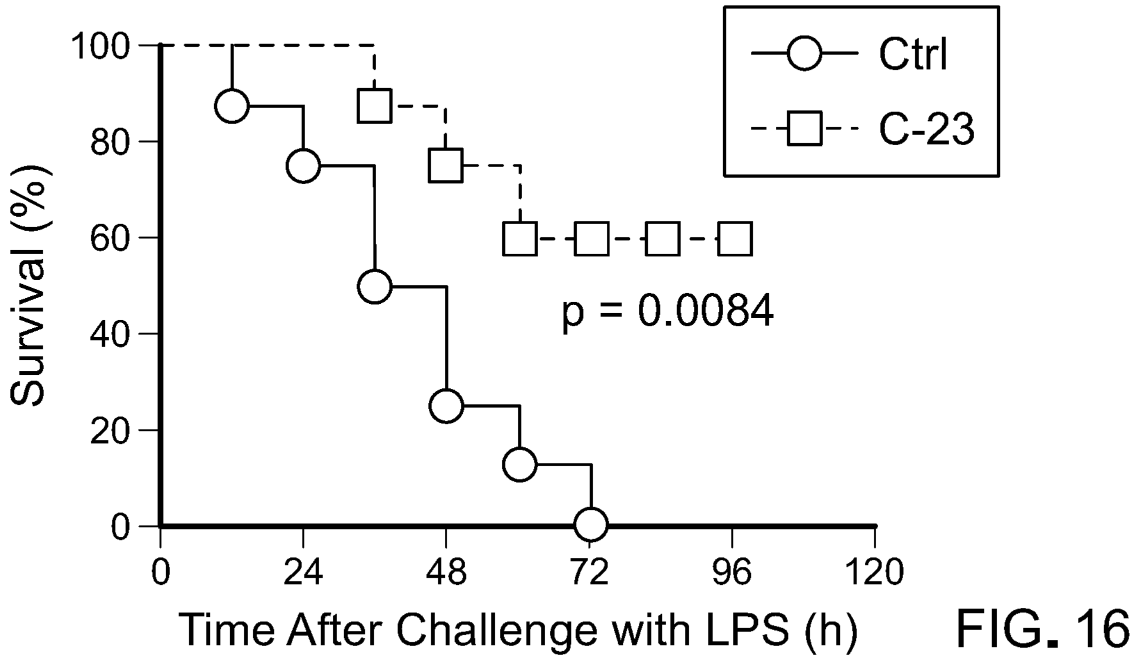
FIG. 16 contains line plots showing % mice survival after challenge with 25 mg/kg of LPS and treatment with C-23.
Figure 17:
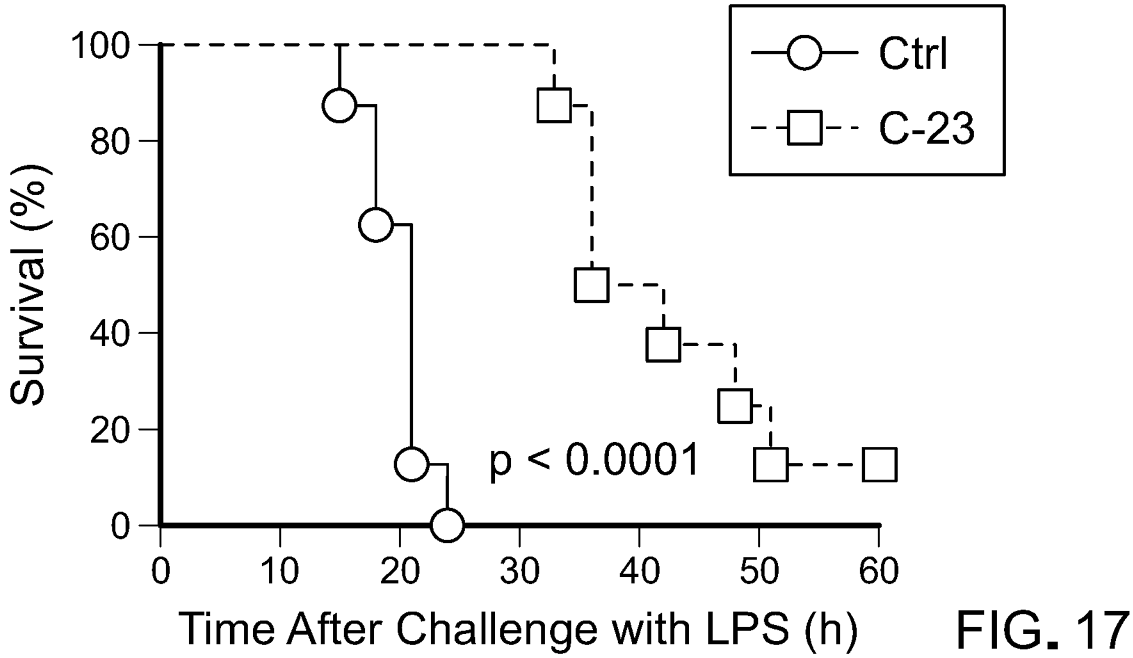
FIG. 17 contains line plots showing % mice survival after challenge with 50 mg/kg of LPS and treatment with C-23.
Figure 18:
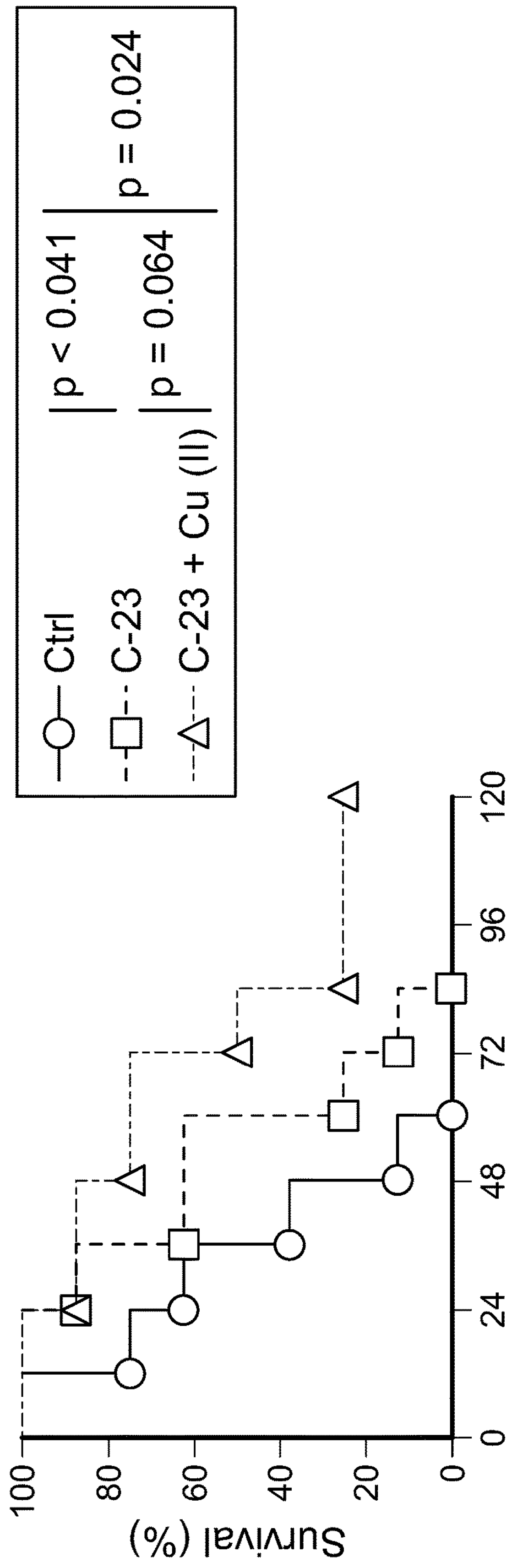
FIG. 18 contains line plots showing % mice survival after mice were treated with C-23 (50 mg/kg), C-23 (50 mg/kg) plus copper gluconate (0.15 mg/kg) or vehicle (Ctrl) by intraperitoneal injection 0 and 12 hours post intraperitoneal LPS challenge (25 mg/kg).
Figure 19:
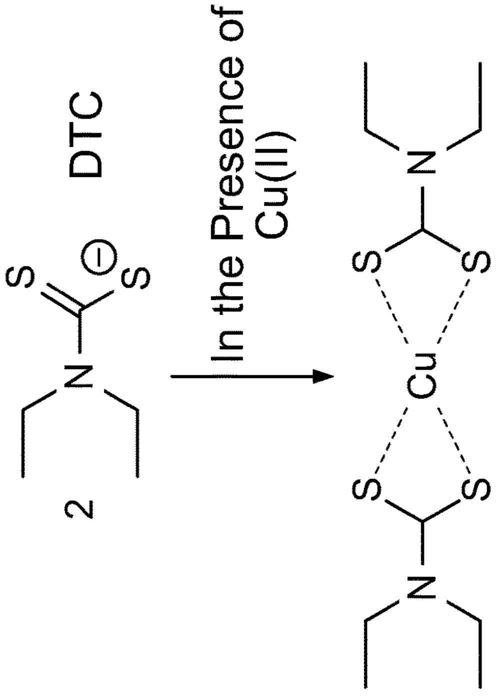
FIG. 19 contains a chemical scheme showing chemical reaction between DTC and $Cu^{2+}$.

Because C-23 inhibited pyroptosis and IL-1β release in cells, its ability to protect C57BL/6 mice from LPS-induced sepsis was also tested. Mice were treated with vehicle or disulfiram intraperitoneally before challenge with LPS. Whereas the lowest concentration of LPS (15 mg/kg) killed 3 of 8 control mice after 96 hrs, all the disulfiram-treated mice survived (P<0.05) (FIG. 14). Serum IL-1β concentrations were strongly reduced 12 hrs after LPS challenge when all mice were alive (281±149 ng/mL in disulfiram-pretreated mice, 910±140 ng/mL in control mice (P<0.0001)) (FIG. 15). Following LPS challenge at the intermediate concentration (25 mg/kg), all the control mice died within 72 hrs, but 5 of 8 of the disulfiram-treated mice survived (P<0.01) (FIG. 16). At the highest LPS challenge (50 mg/kg), while all the control mice died within a day, death was significantly delayed by disulfiram treatment and 1 of 8 mice survived (P<0.0001) (FIG. 17). To determine if treatment could be delayed until after LPS challenge and whether adding copper could improve protection, mice were challenged with 25 mg/kg LPS intraperitoneally and administered C-23 with or without copper gluconate immediately and 24 hrs later. Post-LPS treatment still improved survival (P=0.041 without copper and P=0.024 with copper). All the control mice and mice treated without copper died, but 2 of 8 mice given copper-complexed disulfiram survived (FIG. 18). Thus, disulfiram given before or after LPS partially protected mice from septic death and reduced IL-1β secretion.

Figure 12:
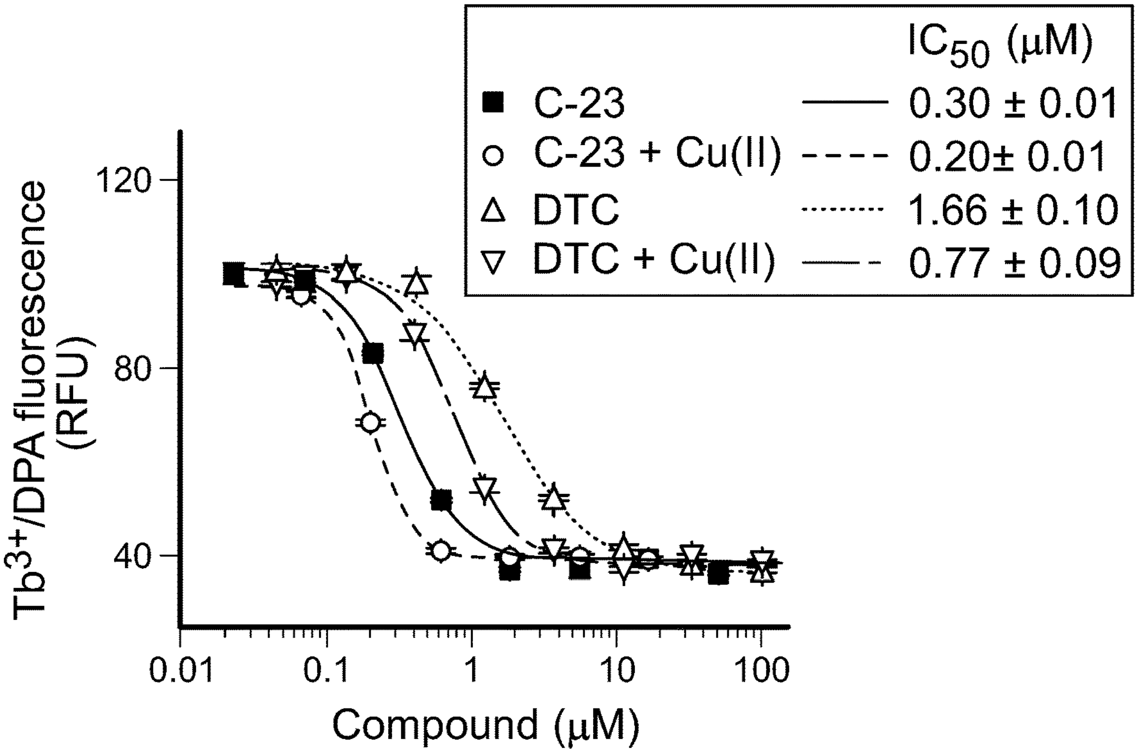
FIG. 12 contains dose response curves of inhibition of liposome leakage by disulfiram (C-23) or its metabolite DTC in the presence or absence of Cu(II).

Experimental results: FIG. 12 shows dose response curves of inhibition of liposome leakage by C-23 or its metabolite DTC in the presence or absence of Cu(II). In FIG. 13, LPS-primed THP-1 were pre-treated with C-23 or DTC in the presence or absence of Cu(II) for 1 hr before adding nigericin or medium for 2 hrs. Cell death was determined by CytoTox96 assay. In FIGS. 14-17, mice were pre-treated with C-23 (50 mg/kg) or vehicle (Ctrl) by intraperitoneal injection 24 and 4 hrs before intraperitoneal LPS challenge (FIGS. 14 and 15: 15 mg/kg; FIG. 16: 25 mg/kg; FIG. 17: 50 mg/kg) and followed for survival. Statistical analysis was performed using the log-rank test (In FIGS. 14, 16, 17, mice/group). In FIG. 15, serum IL-1β measured by ELISA in mice (n=5/group) pre-treated with C-23 as above and challenged with 15 mg/kg LPS. Serum was obtained 12 hrs post LPS challenge. Shown are mean±s.d. In FIG. 18, mice were treated with C-23 (50 mg/kg), C-23 (50 mg/kg) plus copper gluconate (0.15 mg/kg) or vehicle (Ctrl) by intraperitoneal injection 0 and 12 hrs post intraperitoneal LPS challenge (25 mg/kg). Statistical analysis was performed using the log-rank test (8 mice/group).

In cells, Cu(II) strongly promoted the ability of either disulfiram or DTC to protect LPS-primed THP-1 cells from pyroptosis, presumably because Cu(II) promoted the activity of the major cellular metabolite DTC. With Cu(II), the $IC_{50}$ of disulfiram for inhibiting pyroptosis decreased 24-fold to 0.41±0.02 μM, which was similar to its potency for preventing liposome leakage. DTC became almost as active as disulfiram in cells in the presence of Cu(II). The similar potency of disulfiram (when its principal cellular metabolite is stabilized) at inhibiting GSDMD pore formation in liposomes and pyroptosis in cells supports GSDMD as a major target of the mechanism of action of disulfiram.

Example 3—Disulfiram Covalently Modifies GSDMD Cys191

Figure 20:
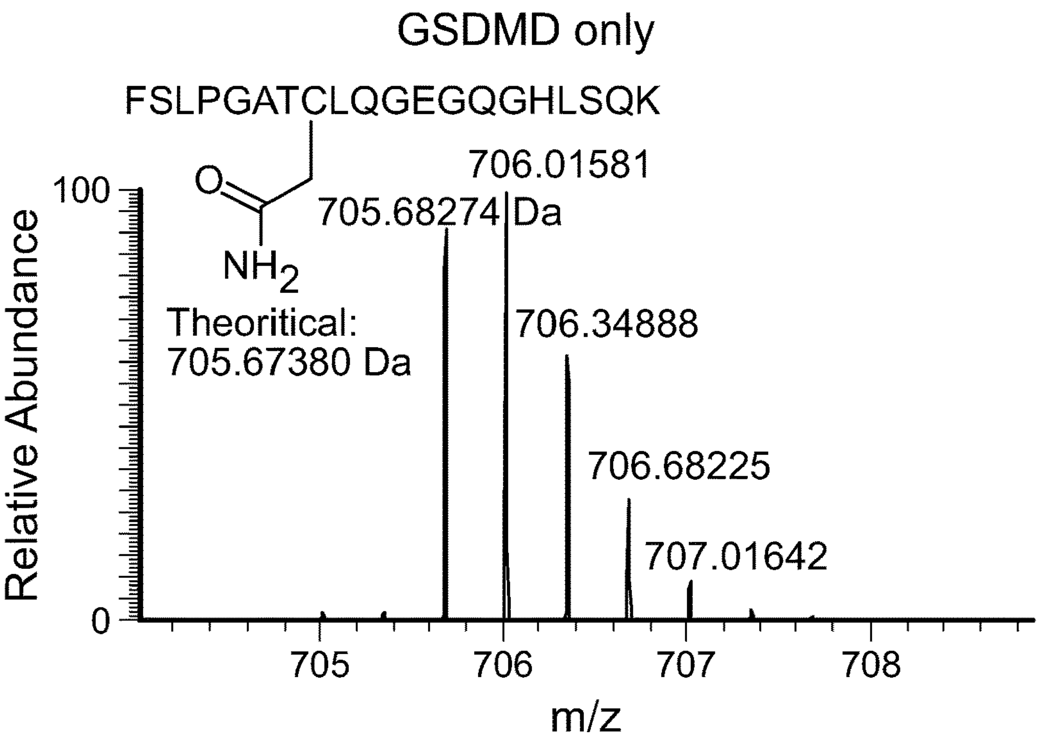
FIG. 20 contains an MS/MS spectrum of the Cys191-containing human GSDMD peptide.
Figure 21:
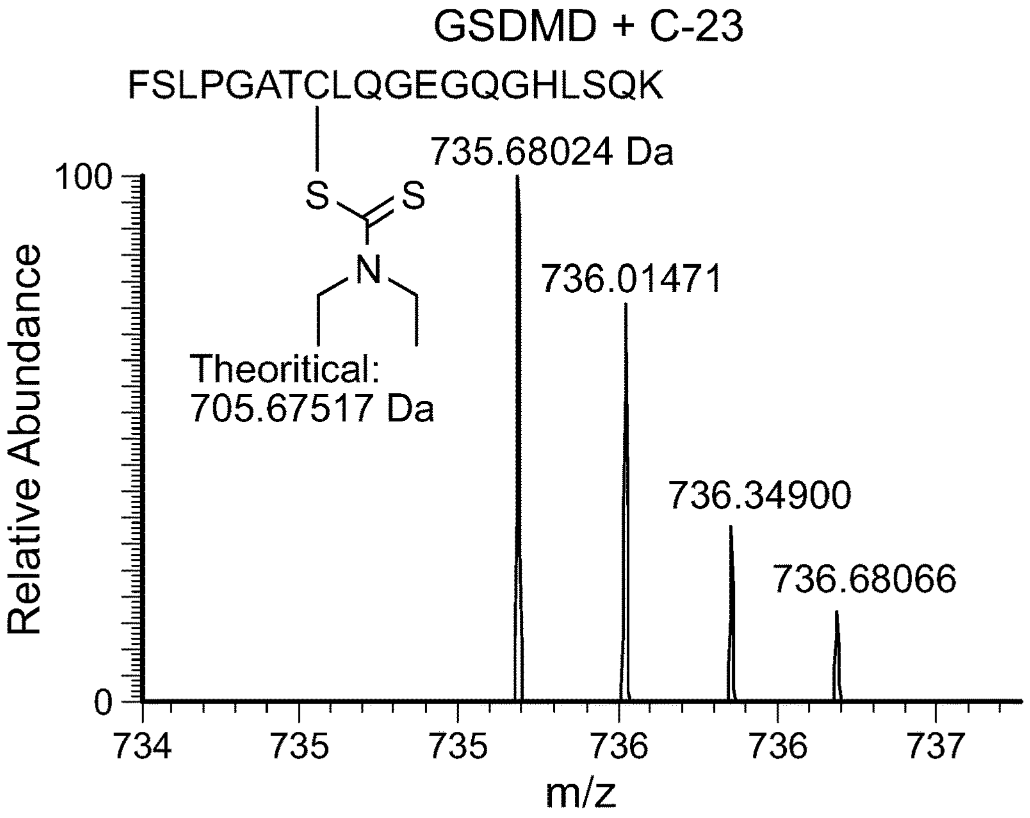
FIG. 21 contains an MS/MS spectrum of GSDMD peptide after incubation with C-23, having a covalent modification on Cys191 by the diethyldithiocarbamate moiety of C-23.
Figure 22:
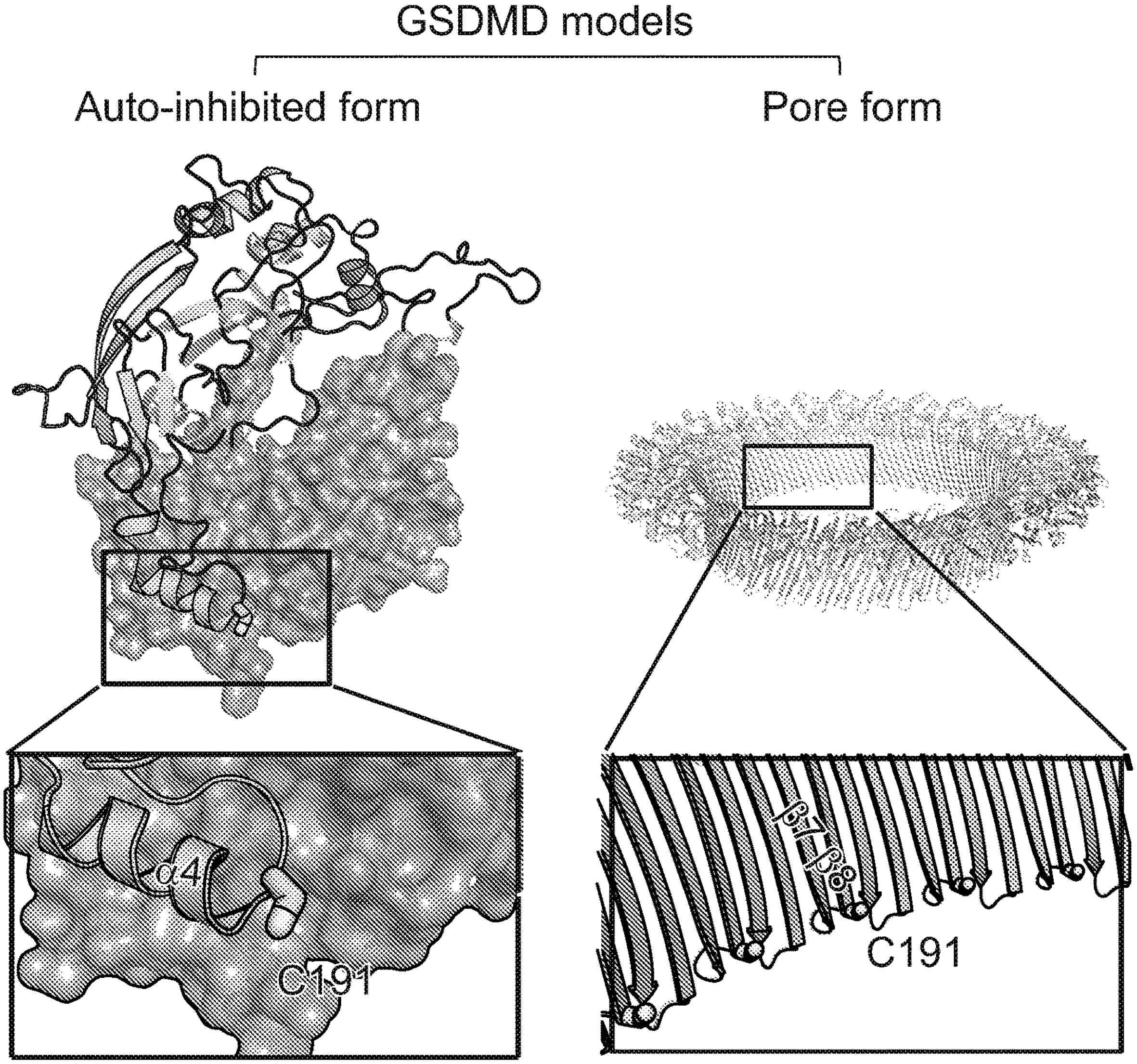
FIG. 22 contains images showing models of full-length human GSDMD in its auto-inhibited form and of the pore form of GSDMD N-terminal fragment (GSDMD-NT) based on the corresponding structures of GSDMA3.
Figure 23:
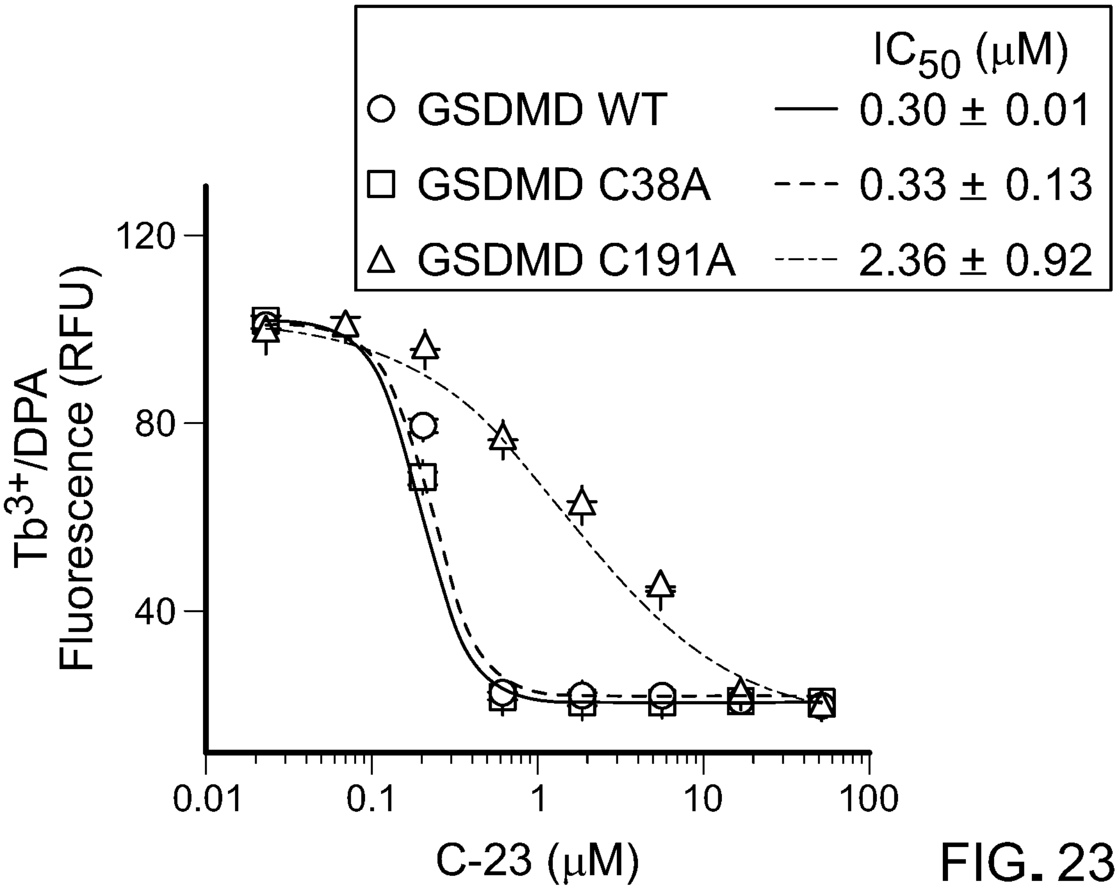
FIG. 23 contains dose response curve of C-23 inhibition of liposome leakage induced by wild-type, C38A or C191A GSDMD (0.3 μM) plus caspase-11 (0.15 μM).
Figure 24:
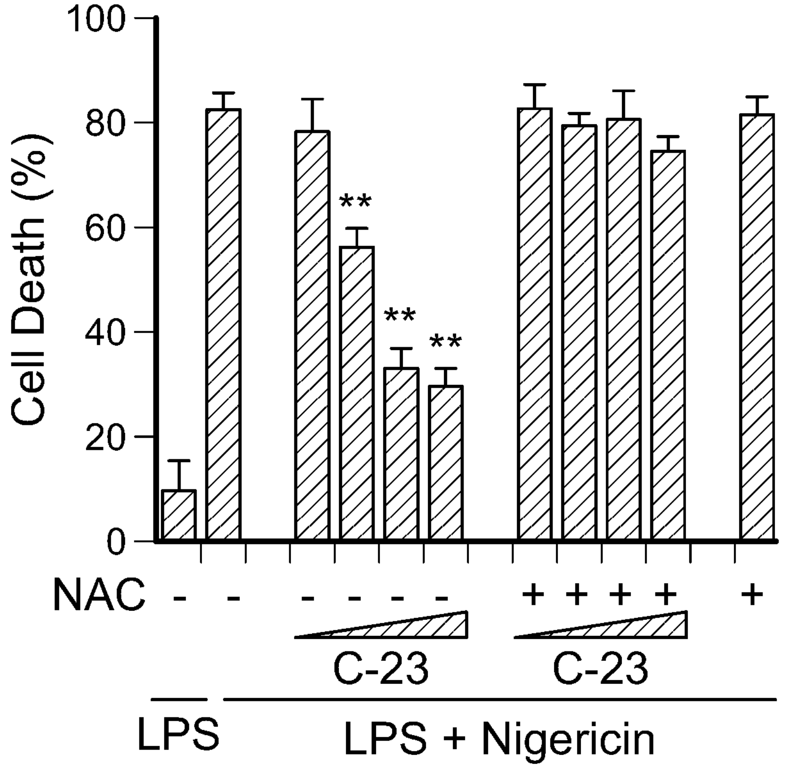
FIG. 24 contains a bar graph showing C-23 inhibition of pyroptosis of LPS+nigericin treated THP-1 cells after C-23 preincubation for 1 hour with N-acetylcysteine (NAC, 500 μM) or medium.
Figure 30:
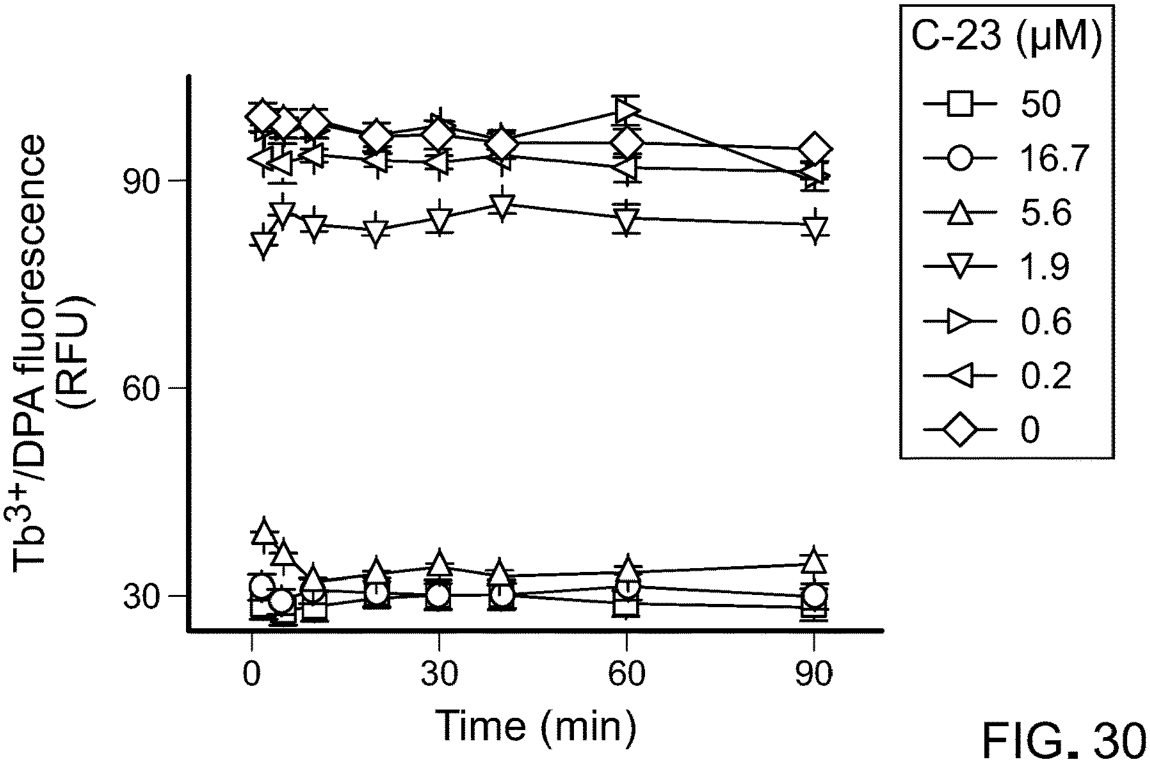
FIG. 30 contains line plots showing $Tb^{3+}$/DPA fluorescence of GSDMD (0.3 μM) pre-incubated with the indicated concentrations of C-23 (0-50 μM) for different durations (2-90 min) before caspase-11 (0.15 μM) in liposome (50 μM) was added.

Disulfiram has been shown to inactivate reactive Cys residues by covalent modification (See Reference 27). To probe the mechanism of GSDMD inhibition by disulfiram, nano-liquid chromatography-tandem mass spectrometry (nano-LC-MS/MS) was used to analyse disulfiram-treated human GSDMD. Tryptic fragments indicated a dithiodiethylcarbamoyl adduct of Cys191, in which half of the symmetrical disulfiram molecule is attached to the thiol (FIGS. 20, 21, 27, and 28). Indeed, Cys191 is required for GSDMD pore formation in cells, since oligomerization was blocked by Ala mutation of the corresponding Cys192 in mouse GSDMD (See Reference 8). This Cys residue, conserved in GSDMD, but not in other GSDM family members, is accessible in both the full-length autoinhibited structure model and the N-terminal pore form model, generated based on mouse GSDMA3 structures (References 7 and 14) (FIGS. 22 and 29). Corresponding to Leu183 of GSDMA3, Cys191 sits at the distal tip of the membrane spanning region at the beginning of the β8 strand within the β7-β8 hairpin, which is a key element in the β-barrel that forms the pore (Reference 14). Analysis of Cys reactivity using PROPKA (Reference 28) suggests that Cys191 is the most reactive among all Cys residues in GSDMD. Consistent with its high reactivity, a time course analysis showed that disulfiram inhibited liposome leakage within 2 min of incubation (FIG. 30). To confirm that disulfiram acts on Cys191, Ala mutations of Cys191, and of Cys38 as a control, were generated. Whereas the disulfiram $IC_{50}$ values for WT and $C_{38}A$ were both around 0.3 μM in the liposome leakage assay, the $IC_{50}$ for C191A was about 8-fold higher (FIG. 23). Disulfiram was also incubated with N-acetylcysteine (NAC), which contains a reactive Cys that can inactivate Cys-reactive drugs, before assessing whether disulfiram protects THP-1 cells from nigericin-mediated pyroptosis. As expected, NAC eliminated the activity of disulfiram (FIG. 24). These data together suggest that disulfiram inhibits GSDMD pore formation by selectively and covalently modifying Cys191.

Figure 25:
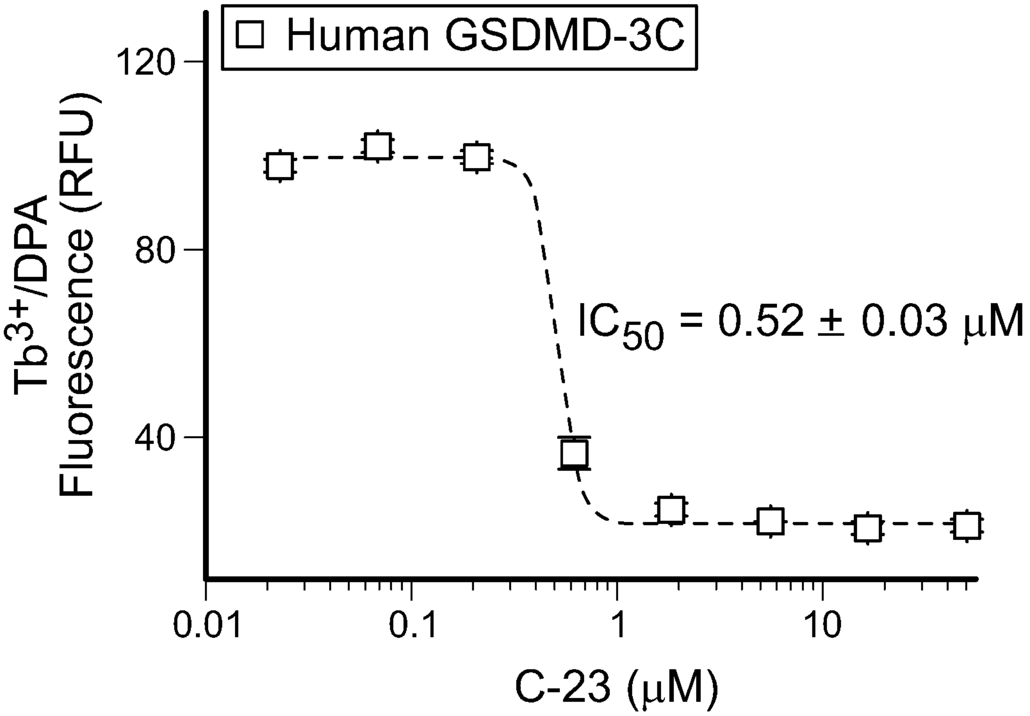
FIG. 25 contains a dose response curve of compound C-23 in liposome leakage induced by human GSDMD-3C (0.3 μM) plus 3C protease (0.15 μM).
Figure 26:
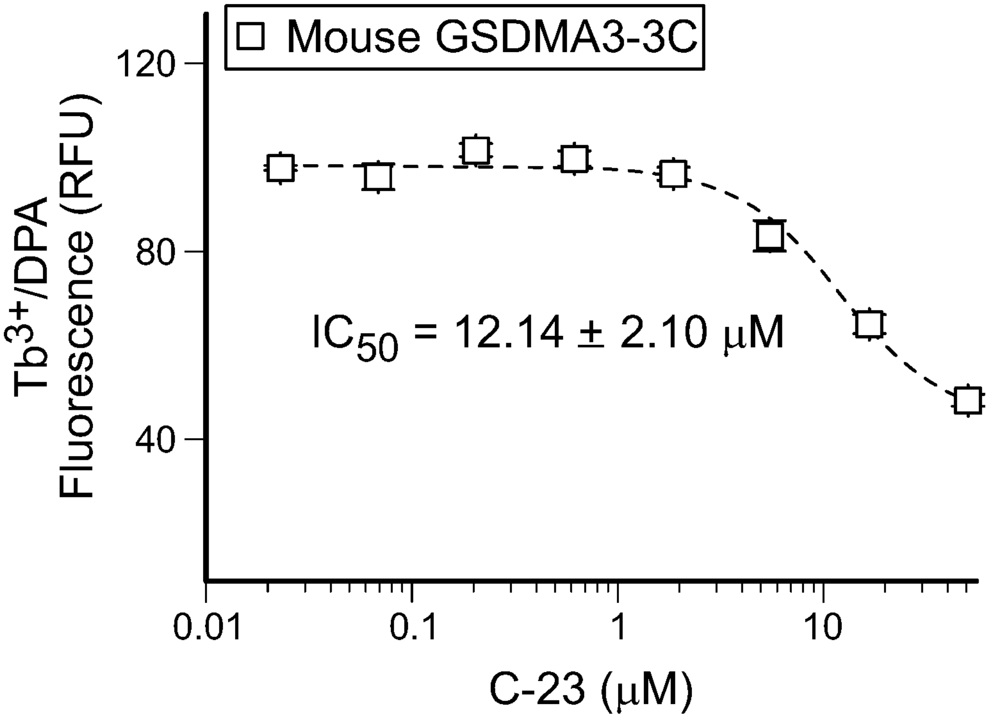
FIG. 26 contains a dose response curve of compound C-23 in liposome leakage induced by human GSDMD-3C (0.3 μM) plus 3C protease (0.15 μM).

Experimental results: FIGS. 20 and 21 show MS/MS spectra of the Cys191-containing human GSDMD peptide FSLPGATCLQGEGQGHLSQK (aa 184-103; 2057.00 Da) modified on Cys191 by carbamidomethyl (an increase of 57.0214 Da) [LC retention time, 22.85 min; a triplet charged precursor ion m/z 705.6827 (mass: 2114.0481 Da; delta M 2.27 ppm) was observed](a) or of the corresponding GSDMD peptide after GSDMD incubation with C-23 (disulfiram), which was modified on Cys191 by the diethyldithiocarbamate moiety of C-23 (an increase of 147.0255 Da). [LC retention time. 28.93 min; a triplet charged precursor ion m/z 735.6802 (mass: 2204.0406 Da; delta M 0.53 ppm) was observed.](b). FIG. 22 shows models of full-length human GSDMD in its auto-inhibited form and of the pore form of GSDMD N-terminal fragment (GSDMD-NT) based on the corresponding structures of GSDMA3 (References 7 and 14) showing the location of Cys191, modified by compound C-23. GSDMD-NT in cyan; GSDMD-CT in grey. FIG. 23 shows dose response curve of C-23 inhibition of liposome leakage induced by wild-type, C38A or C191A GSDMD (0.3 μM) plus caspase-11 (0.15 μM). FIG. 24 shows C-23 inhibition of pyroptosis of LPS+nigericin treated THP-1 cells after C-23 preincubation for 1 hr with N-acetylcysteine (NAC, 500 μM) or medium. 2-fold dilutions of C-23 ranging from 5 to 40 μM were used. Graphs show the mean±s.d. and data shown are representative of three independent experiments. P<0.01. FIGS. 25 and 26 show dose response curve of compound C-23 in liposome leakage induced by human GSDMD-3C (0.3 μM) plus 3C protease (0.15 μM) (FIG. 25) or mouse GSDMA3-3C (0.3 μM) plus 3C protease (0.15 μM) (FIG. 26**).

Figure 27:
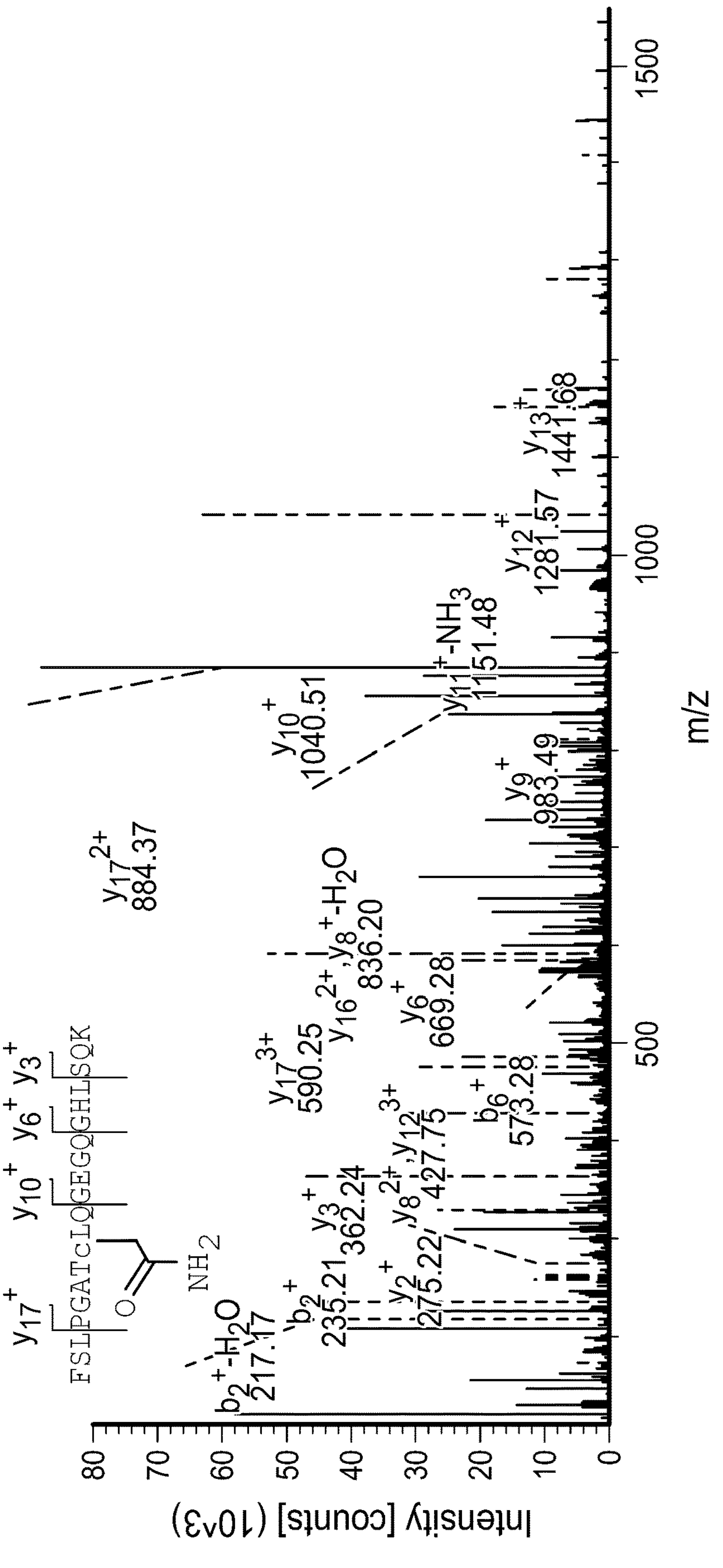
FIG. 27 contains a MS/MS spectrum for peptide FSLPGATCLQGEGQGHLSQK modified on cysteine 191 by carbamidomethyl.
Figure 28:
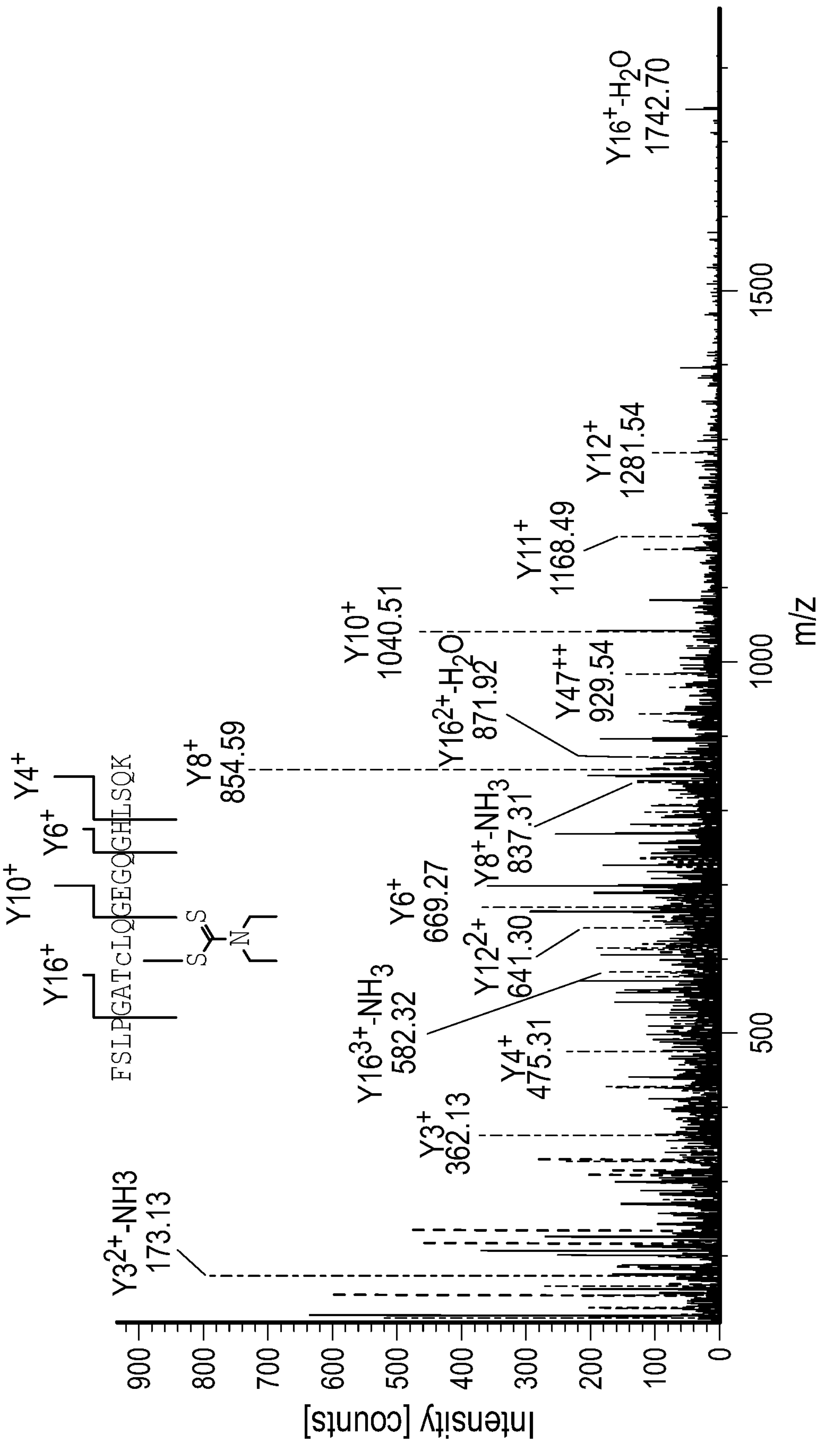
FIG. 28 contains MS/MS spectrum for peptide FSLPGATCLQGEGQGHLSQK modified on cysteine 191 by C-23.

FIGS. 27 and 28 show MS/MS spectrum for the peptide containing Cys191 in human GSDMD. FIG. 27 shows MS/MS spectrum for peptide FSLPGATCLQGEGQGHLSQK modified on cysteine by carbamidomethyl. Protein coverage is 73%. FIG. 28 shows MS/MS spectrum for peptide FSLPGATCLQGEGQGHLSQK modified on cysteine by C-23. Protein coverage is 72%.

FIGS. 29 and 30 show that disulfiram covalently modifies GSDMD Cys191. In FIG. 29, sequence alignment of mouse GSDMA3, human GSDMA (hGSDMA), mouse GSDMD (mGSDMD) and human GSDMD (hGSDMD) shows Cys residues. In FIG. 30, GSDMD (0.3 μM) was preincubated with the indicated concentrations of C-23 (0-50 μM) for different durations (2-90 min) before caspase-11 (0.15 μM) in liposome (50 μM) was added.

To confirm that disulfiram acts on Cys191, the disulfiram $IC_{50}$ values were compared for pore formation in liposomes treated with WT, C38A control or C191A human GSDMD plus caspase-11. The $IC_{50}$ for disulfiram acting on C191A GSDMD was ~8-fold higher than on WT GSDMD, while the activity on C38A was similar to WT GSDMD, confirming the importance of Cys191 for disulfiram activity. The residual inhibition of the Cys191 mutant may be due to disulfiram modifications of other Cys residues in the mutant GSDMD. To confirm the importance of Cys191 in pore formation, cell death was measured by LDH release in HEK293T cells ectopically expressing full-length human WT or C191S mutant GSDMD with or without caspase-11. Although WT or C191S GSDMD alone did not compromise cell survival, WT GSDMD and caspase-11 together caused substantial cell death, which was reduced for C191S GSDMD and caspase-11. Similarly, cell death caused by ectopic expression of mouse GSDMD-NT (mGSDMD-NT) was significantly reduced in HEK293T cells expressing the analogous C192S mutant, but only modestly in cells expressing C39A mGSDMD-NT. These results confirm the role of Cys191 and Cys192 in GSDMD-NT pore formation in humans and mice, respectively, consistent with previous results.

To further confirm that disulfiram acts on Cys191, disulfiram inhibition of LDH release in HEK293T cells expressing caspase-11 and WT or C191S GSDMD was assessed. As expected, WT GSDMD-induced cell death was strongly inhibited by disulfiram in a dose-dependent manner beginning at the lowest concentration tested (10 μM), but the reduced cell death caused by expression of caspase-11 and C191S GSDMD was only inhibited when 4 times as much disulfiram was added. These data together indicate that disulfiram inhibits GSDMD pore formation by covalently modifying Cys191. In addition, the data suggests that disulfiram inhibits cell death mainly through its effect on GSDMD-NT pore formation because if disulfiram strongly inhibited caspase-11, it would have provided better protection from death of cells expressing caspase-11 and C191S GSDMD.

Example 4—Disulfiram (C-23) Inhibits Caspase-1 and Caspase-11

Disulfiram has been reported to inhibit caspases by binding to the catalytic Cys responsible for proteolysis (See Reference 29). It is therefore likely that disulfiram inhibits both caspases and GSDMD. Using a fluorogenic caspase activity assay that measures the release of 7-amino-4-methylcoumarin (AMC) from substrate Ac-YVAD-AMC, it was found that disulfiram indeed inhibited caspase-1 and caspase-11 with $IC_{50}$ of 0.15±0.04 μM and 0.73±0.07 μM, respectively (FIGS. 31-38). Adding Cu(II) did not strongly change disulfiram caspase inhibition in vitro. To determine the relative contribution of caspase-11 inhibition versus GSDMD inhibition by disulfiram in pore formation, the caspase cleavage site in GSDMD was replaced with the rhinovirus 3C protease site (GSDMD-3C) and the 3C protease was used instead of caspase-11 in the liposome leakage assay. The resulting $IC_{50}$ was 0.52±0.03 μM, comparable to 0.30±0.01 μM for caspase-11-triggered liposome leakage (FIGS. 2 and 25). By contrast, as mouse GSDMA3 lacks the conserved Cys191, disulfiram inhibited liposome leakage triggered by 3C-cleaved GSDMA3 containing a 3C protease site (GSDMA3-3C) with a much weaker $IC_{50}$ of 12.14±2.10 μM (FIG. 26). Thus, the inhibitory effect of disulfiram in the liposome leakage assay is mediated by direct inhibition of GSDMD.

Figure 31:
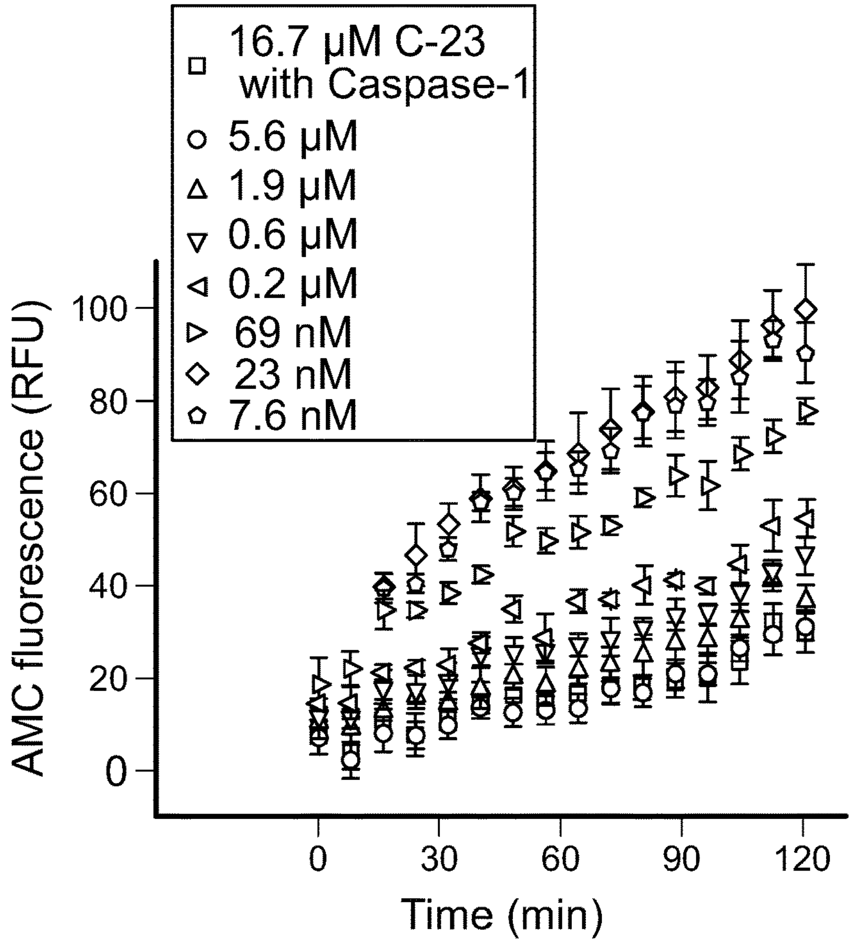
FIG. 31 contains a line plots showing time course of caspase-1 activity in the presence of indicated concentrations of compound C-23.
Figure 32:
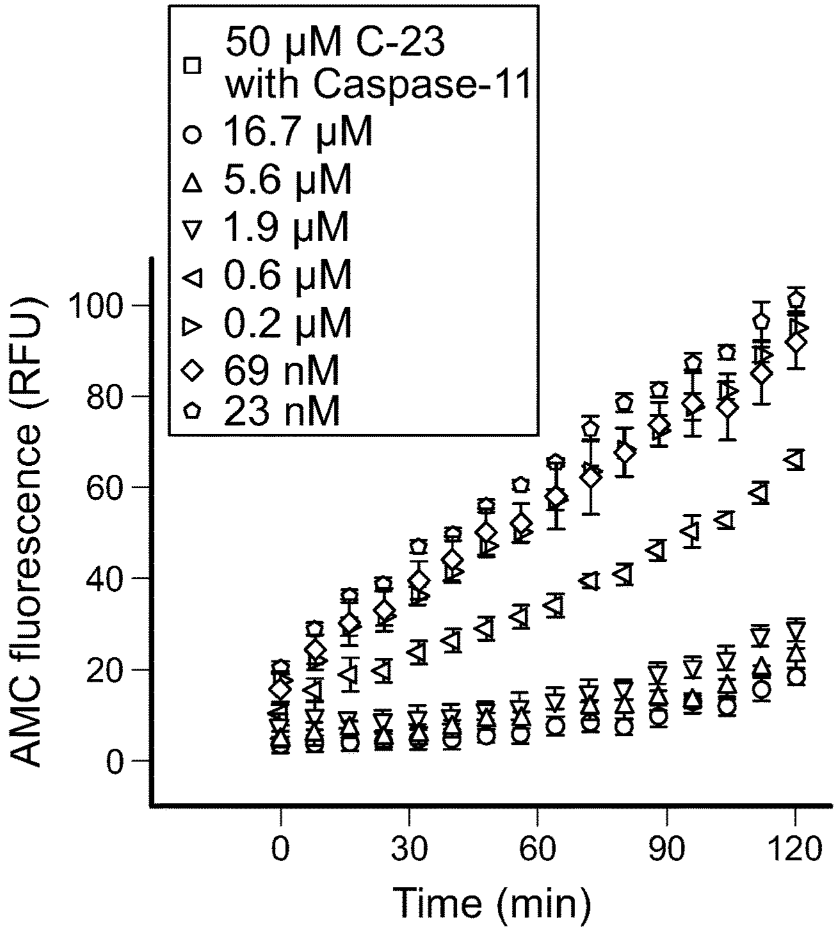
FIG. 32 contains a line plots showing time course of caspase-11 activity in the presence of indicated concentrations of compound C-23.
Figure 33:
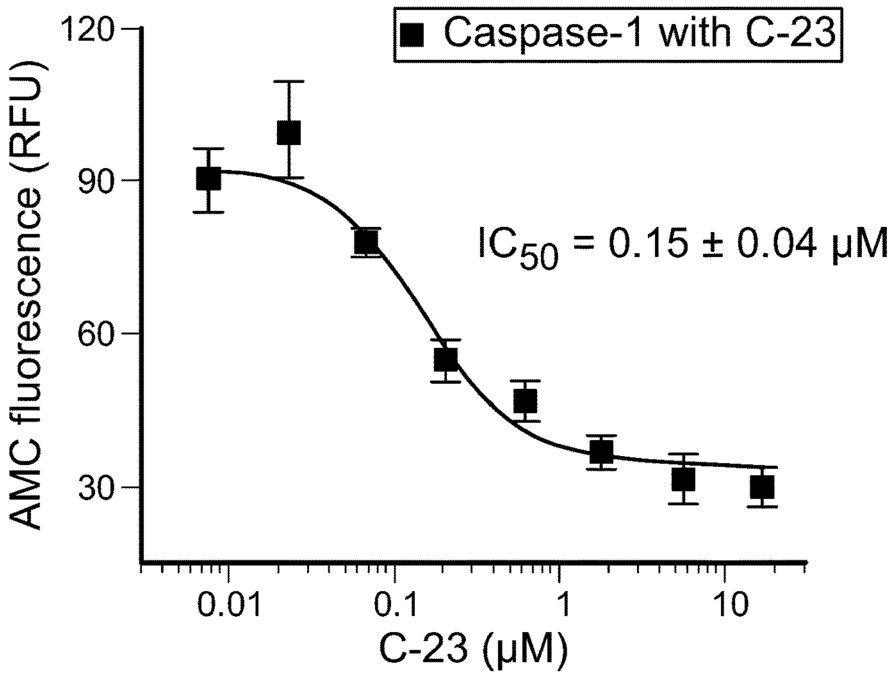
FIG. 33 contains a dose response curve of compound C-23 in the caspase-1 activity assay.
Figure 34:
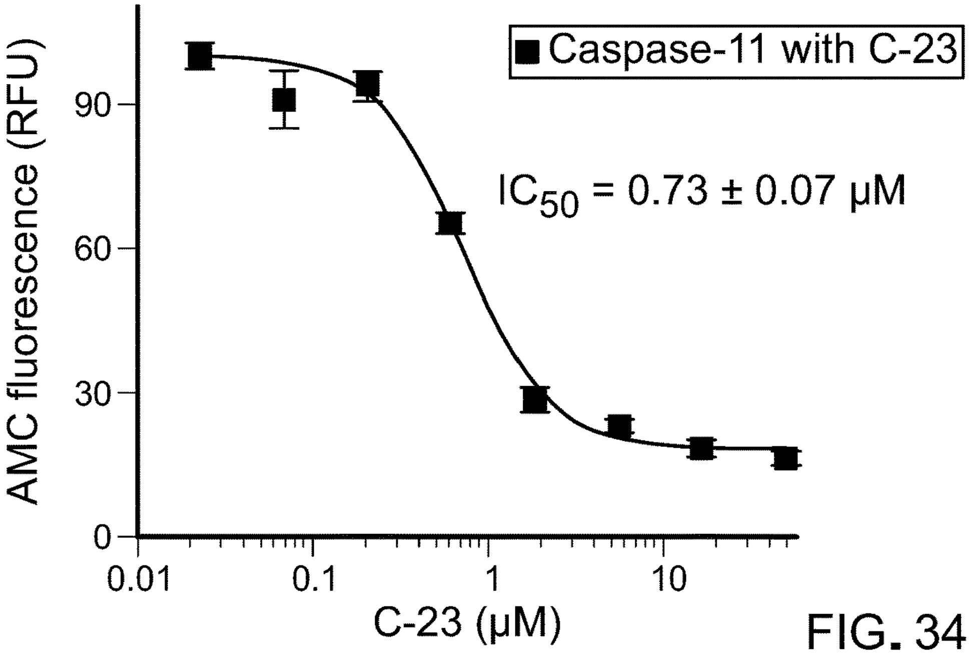
FIG. 34 contains a dose response curve of compound C-23 in the caspase-11 activity assay.
Figure 35:
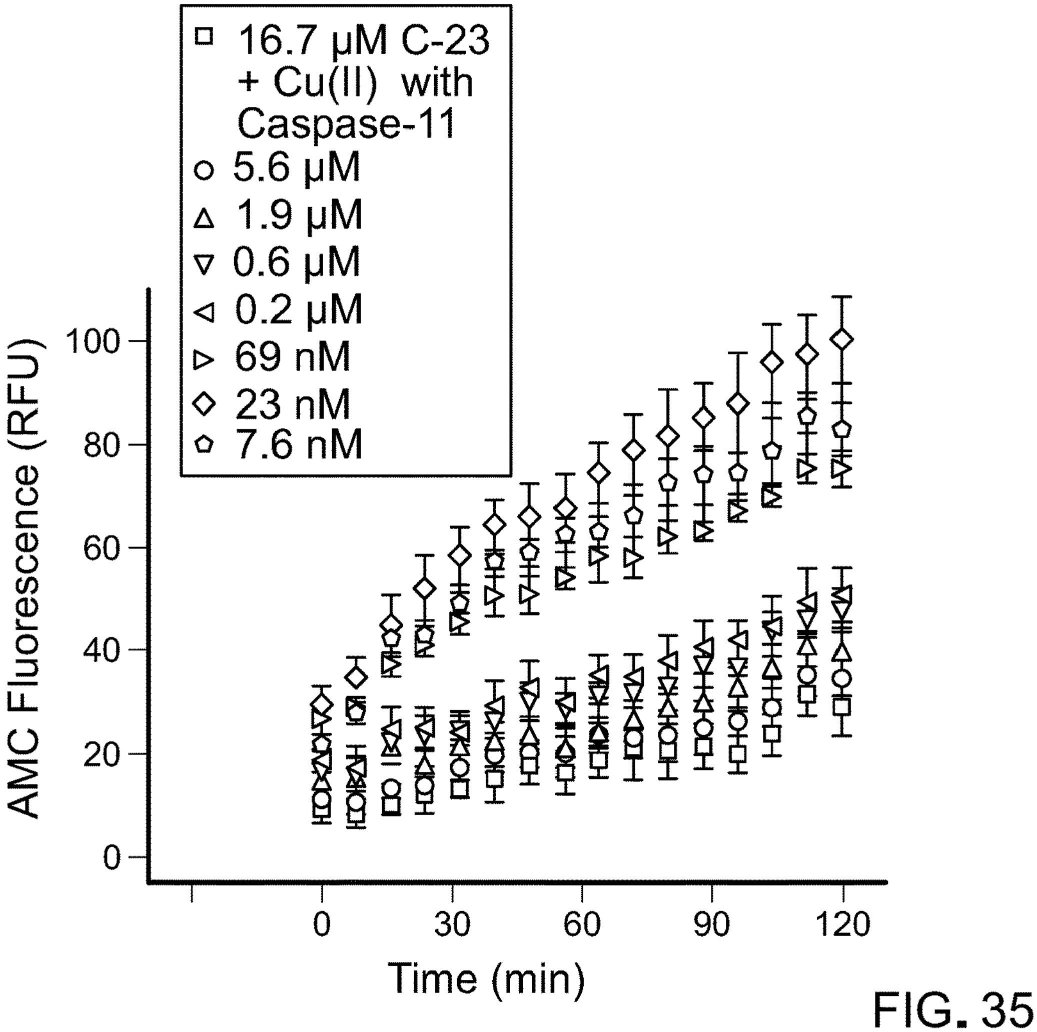
FIG. 35 contains line plots showing time course of caspase-1 activity in the presence of indicated concentrations of compound C-23+Cu(II).
Figure 36:
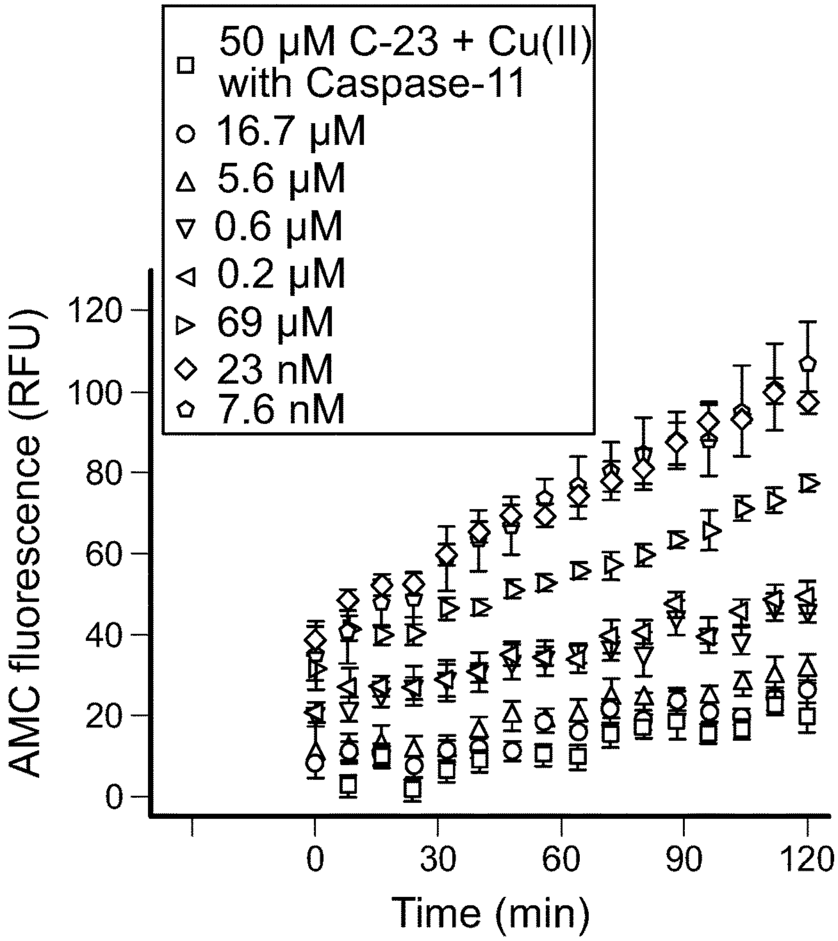
FIG. 36 contains line plots showing time course of caspase-11 activity in the presence of indicated concentrations of compound C-23+Cu(II).
Figure 37:
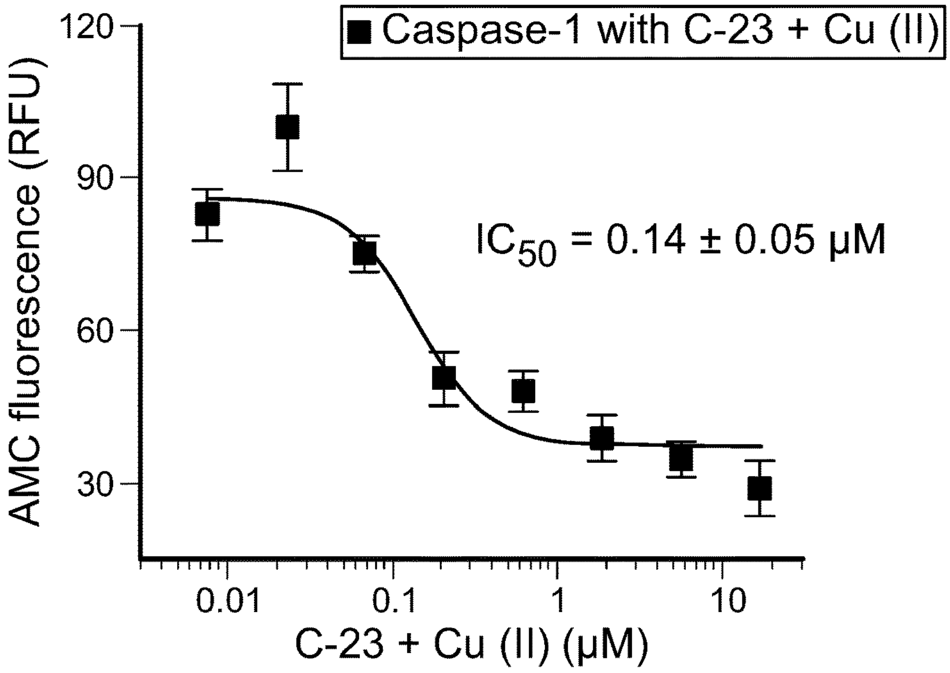
FIG. 37 contains a dose response curve of compound C-23+Cu(II) in the caspase-1 activity assay.
Figure 38:
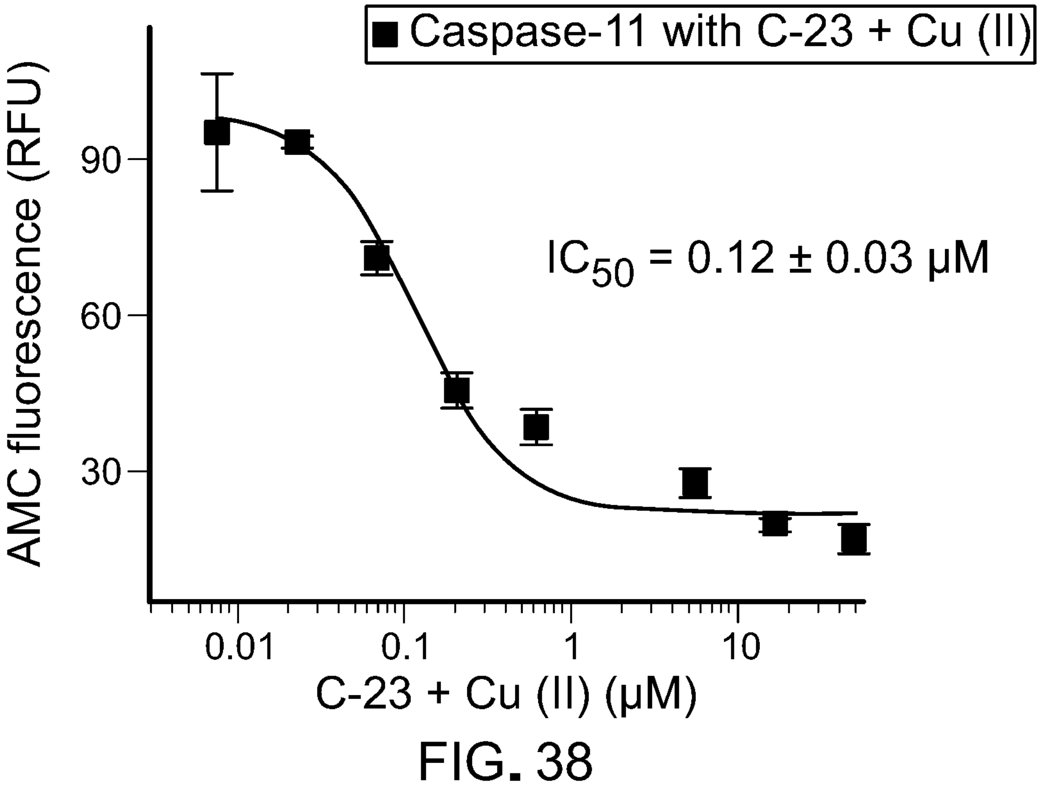
FIG. 38 contains a dose response curve of compound C-23+Cu(II) in the caspase-11 activity assay.

Experimental results: FIGS. 31 and 32 show time course of caspase-1 and caspase-11 activity in the presence of indicated concentrations of compound C-23. Caspases (0.5 U) were incubated with compound C-23 (at indicated concentrations for 1 hr before adding Ac-YVAD-AMC (40 μM)). FIGS. 33 and 34 show dose response curve of compound C-23 in the caspase-1 and caspase-11 activity assay. FIGS. 35 and 36 show time course of caspase-1 and caspase-11 activity in the presence of indicated concentrations of compound C-23+Cu(II). Caspases (0.5 U) were incubated with compound C-23+Cu(II) (at indicated concentrations for 1 hr before adding Ac-YVAD-AMC (40 μM)). FIGS. 37 and 38 show dose response curve of compound C-23+Cu(II) in the caspase-1 and caspase-11 activity assay. Fluorescence intensity at 460 nm was measured after excitation at 350 nm.

Figure 41:
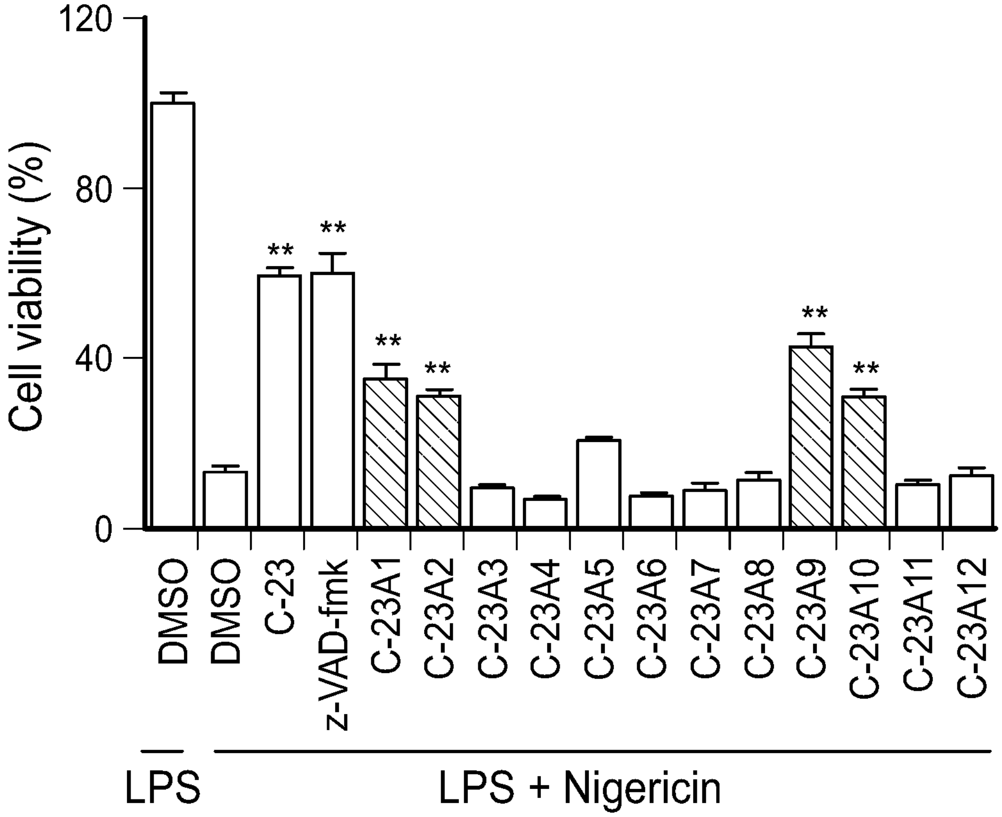
FIG. 41 contains a bar graph showing results of cell viability assay for the compounds of Table 2 and FIG. 39, with or without nigericin.
Figure 42:
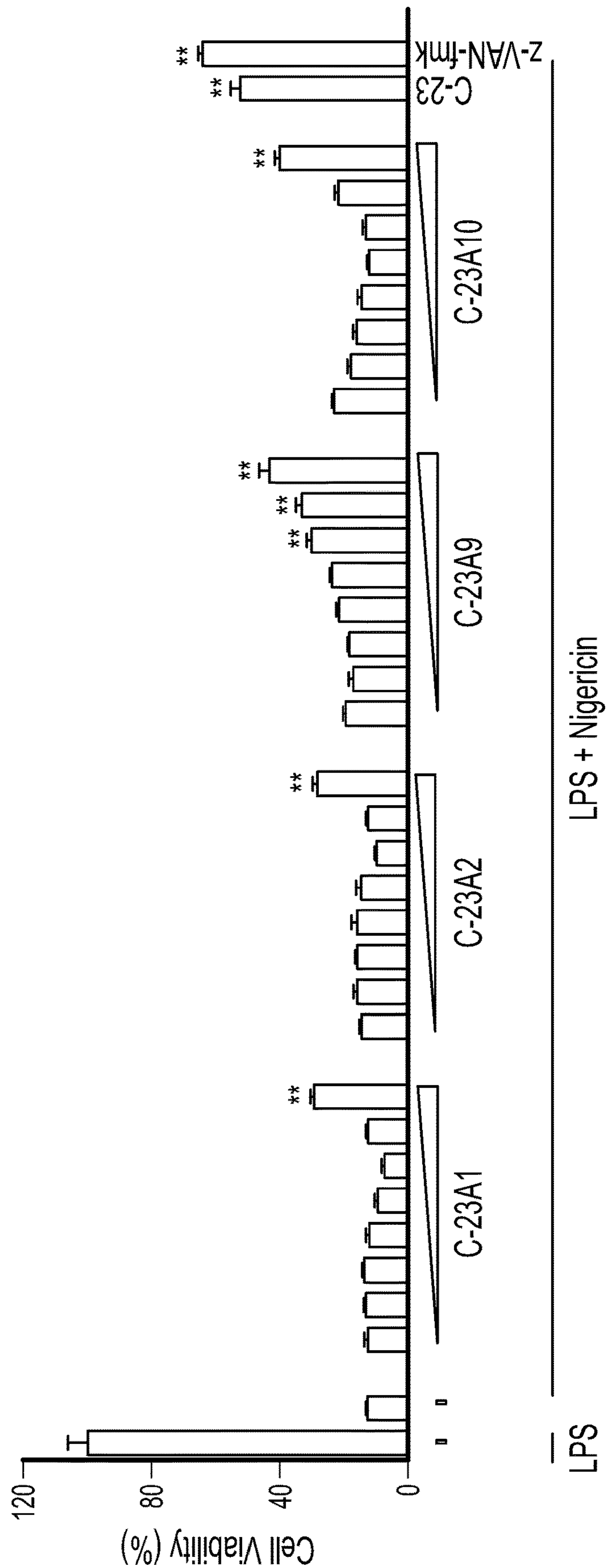
FIG. 42 contains a bar graph showing results of cell viability assay for the compounds C-23A1, C-23A2 C-23A9, and C-23A10, after adding nigericin.

Example 5—Test Compounds Inhibit GSDMD Pore Formation $IC_{50}$ values of the test compounds shown in FIG. 39 in liposome leakage assay are shown in FIGS. 40-42. Data shows that the tested compounds protected against nigericin-induced pyroptosis in THP-1. Results of the leakage assay are shown in Table 2. Chemical structures of compounds listed in Table 2 are shown in FIG. 39.

TABLE 2

| Compound | $IC_{50}$ (μM) |
|---|---|
| C-23 | 0.30 ± 0.01 |
| C-23A1 | 0.22 ± 0.01 |
| C-23A2 | 0.37 ± 0.01 |
| C-23A3 | 0.46 ± 0.08 |
| C-23A4 | 0.26 ± 0.01 |
| C-23A5 | 3.74 ± 1.06 |
| C-23A6 | 0.35 ± 0.03 |
| C-23A7 | 0.25 ± 0.01 |
| C-23A8 | 1.25 ± 0.01 |
| C-23A9 | 0.26 ± 0.003 |
| C-23A10 | 0.26 ± 0.02 |
| C-23A11 | 0.37 ± 0.01 |
| C-23A12 | 2.93 ± 1.07 |

Experimental results: in FIG. 40, PMA-differentiated LPS-primed THP-1 cells were treated with the indicated compounds (40 μM) for 3 hrs and tested for viability by CellTiter-Glo assay. In FIG. 41, PMA-differentiated LPS-primed THP-1 cells were pretreated with 40 μM disulfiram or the indicated test compounds or z-VAD-fmk for 1 hr before treatment or not with nigericin, and the cells were assessed for cell viability by CellTiter-Glo assay 2 hrs after adding nigericin. In FIG. 42, PMA-differentiated LPS-primed THP-1 cells were pretreated with 40 μM disulfiram or z-VAD-fmk or with 2-fold serial dilutions (concentration range, 0.39-50 μM) of indicated test compounds for 1 hr before adding nigericin, and the cells were assessed for cell viability by CellTiter-Glo assay 2 hrs after adding nigericin. Graphs show the mean±s.d. and data shown are representative of three independent experiments. **P<0.01. None of the tested compounds was toxic to THP-1 cells (See Figures). The tested compounds also significantly protected against nigericin-induced pyroptosis in THP-1 cells.

Example 6a—Disulfiram and Bay 11-7082 Inhibit Multiple Steps in Inflammasome Activation Cascade It was found that pan-caspase inhibitor z-VAD-fmk (CAS Registry No. 187389-52-2):

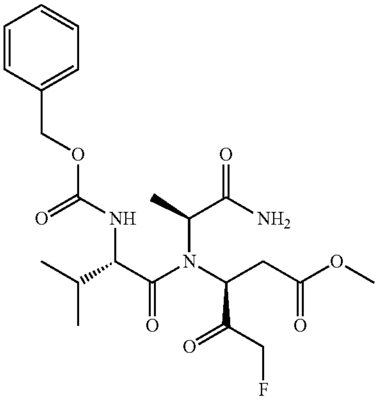 [SMILES: COC(=O)C[C@@H](C(=O)CF)N(C(=O)[C@@H](NC(=O)OCc1ccccc1)C(C)C)[C@@H](C)C(N)=O]

inhibits the canonical inflammasome pathway in THP-1 cells.

It was also found that Bay 11-7082 (CAS Registry No. 19542-67-7):

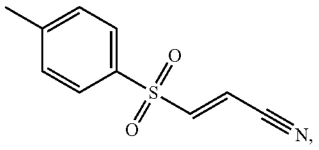

a previously known inhibitor of NF-κB activation (Reference 13) and the NLRP3 pathway (Reference 30) (FIG. 43) also inhibits the canonical inflammasome pathway in THP-1 cells. As discussed below, Bay 11-7082 inhibits, e.g., GSDMD, caspase-1 and caspase-11.

Figure 55:
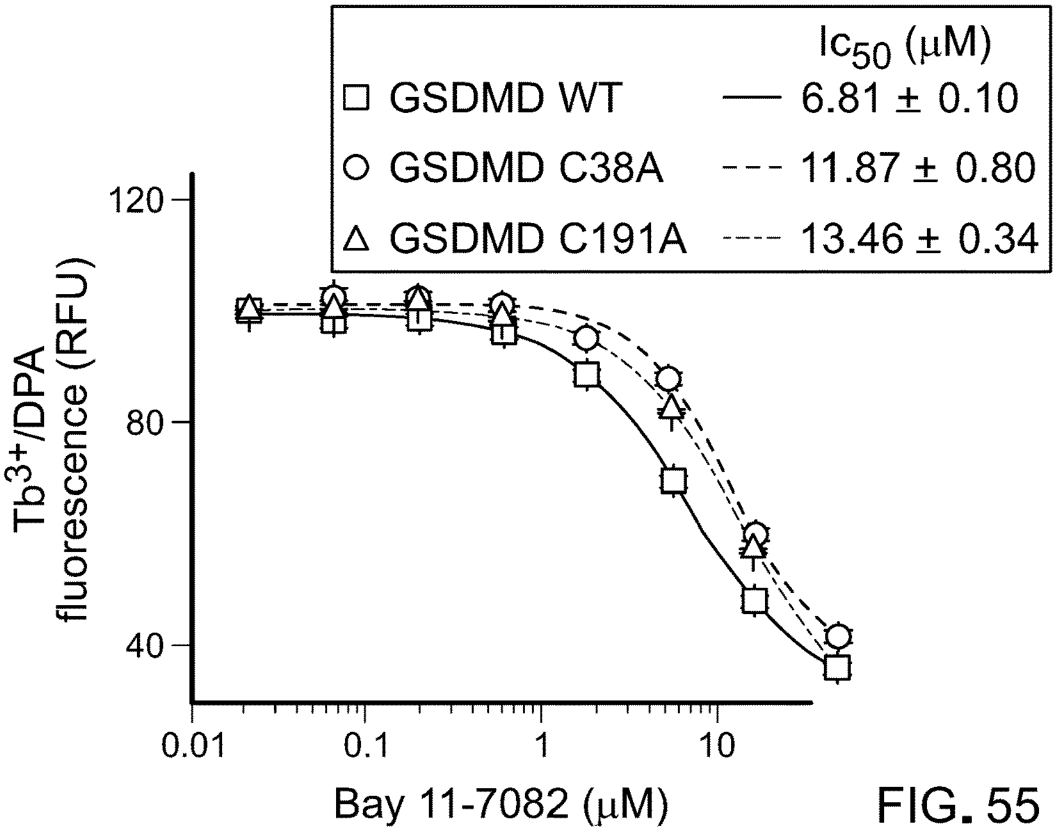
FIG. 55 contains response curve of Bay 11-7082 inhibition of liposome leakage by wild-type, C38A or C191A human GSDMD.
Figure 56:
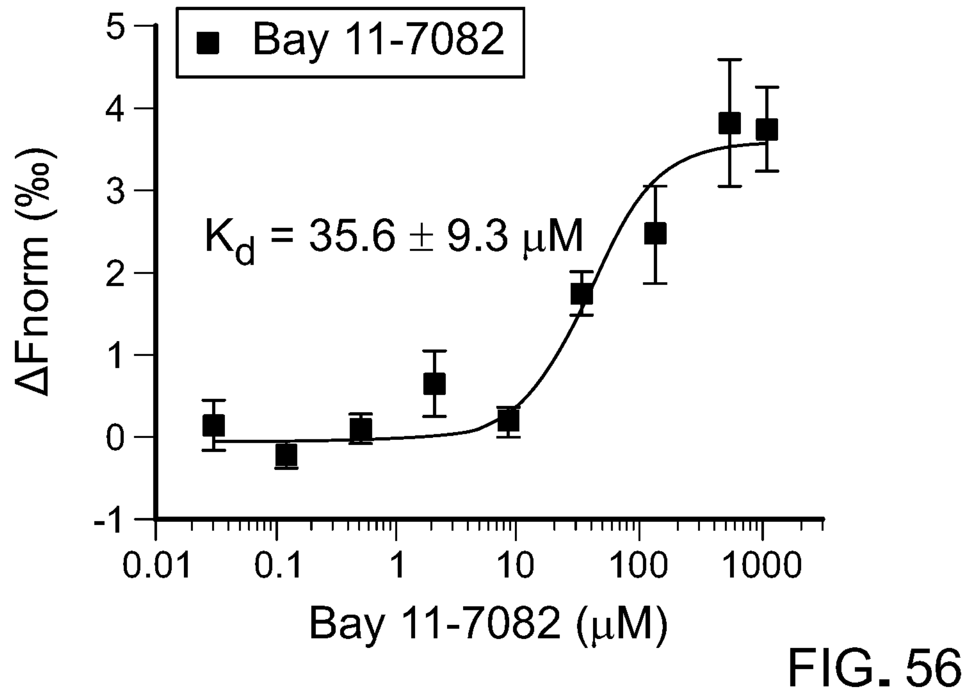
FIG. 56 contains a line plot showing thermophoresis measurement of the direct binding of Alexa 488-labeled His-MBP-GSDMD with Bay 11-7082.

Bay 11-7082 bound to GSDMD according to MST (See FIGS. 55 and 56 and FIG. 2). Bay 11-7082 inhibited caspase-1 and to lesser extend caspase-11 (See FIGS. 55-58). Surprisingly, like disulfiram, Bay 11-7082 functions by inactivating reactive Cys residues (See References 31 and 32), and Cys191 in GSDMD was covalently modified by Bay 11-7082 (See FIGS. 59 and 60). Bay 11-7082 inhibition of liposome leakage was reduced 2-fold by substituting $C_{191}$A GSDMD for WT GSDMD in the liposome leakage assay (FIG. 55). Much of Bay 11-7082 inhibition of liposome leakage could be attributed to caspase-11 inhibition, since Bay 11-7082 was less able to inhibit leakage caused by GSDMD-3C plus 3C protease than by GSDMD plus caspase-11 and its activity against mouse GSDMA3-3C, which lacks a comparable reactive cysteine, plus 3C protease was similar to its activity against GSDMD-3C (See FIGS. 61 and 62).

Figure 43:
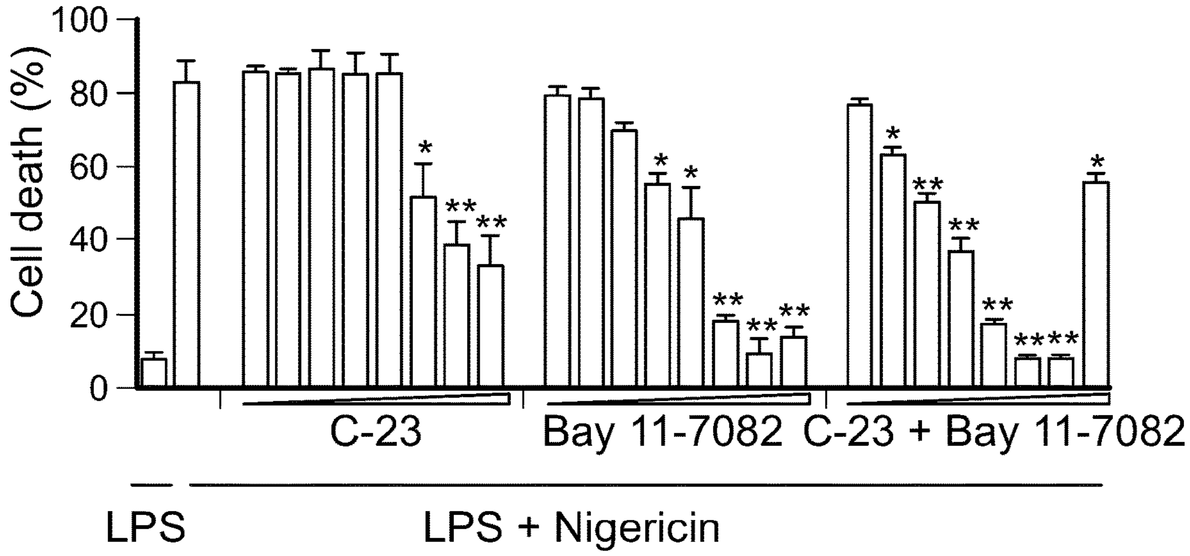
FIG. 43 contains a bar graph showing results of cell viability assay for the compounds C-23, Bay 11-7082, and C-23+Bay 11-7082.
Figure 44:
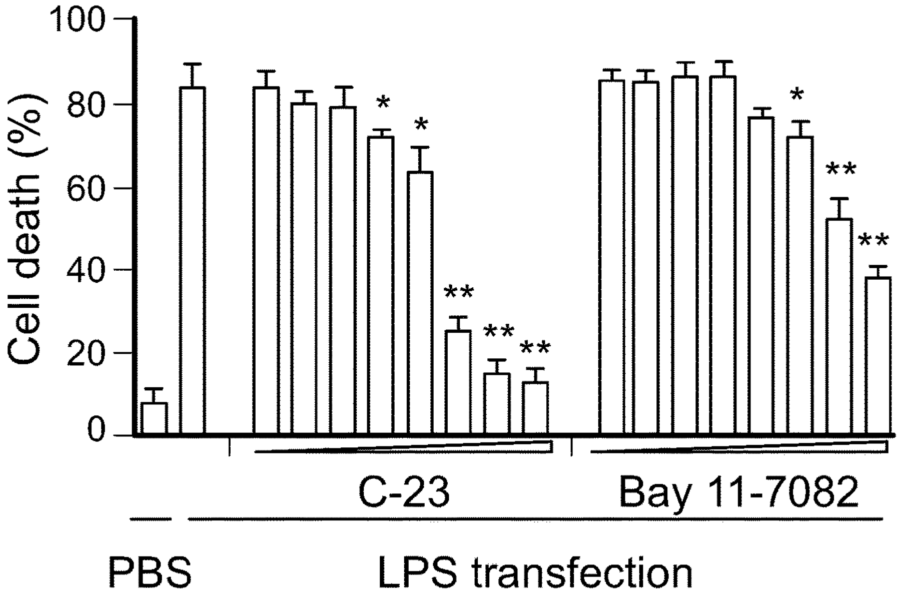
FIG. 44 contains a bar graph showing results of cell viability assay for the compounds C-23 and Bay 11-7082 after LPS transfection.

Bay 11-7082 inhibited pyroptosis triggered by both the canonical and non-canonical inflammasomes in THP-1 cells, but was more active in nigericin-treated than LPS-transfected cells (FIGS. 43 and 44). Bay 11-7082 was more effective at inhibiting canonical inflammasome-dependent pyroptosis than disulfiram in the absence of copper, and the two drugs together had an additive protective effect, although were cytotoxic at the highest concentration tested (FIG. 43). Bay 11-7082 was less active than disulfiram at inhibiting pyroptosis induced by non-canonical inflammasome activation (FIG. 44).

Figure 45:
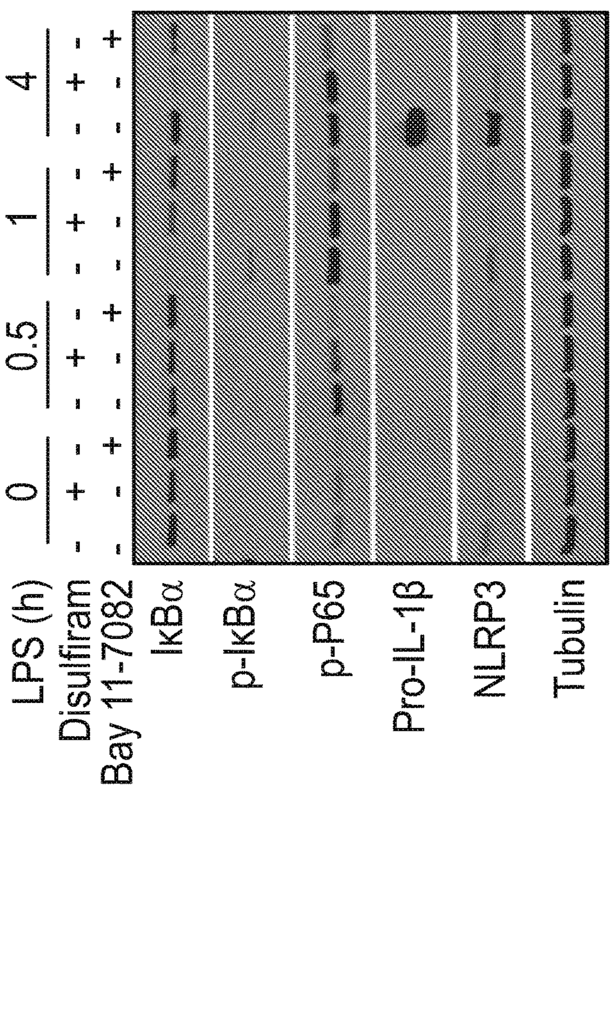
FIG. 45 contains images of immunoblots of THP-1 cells pretreated with C-23 and Bay 11-7082.
Figure 46:
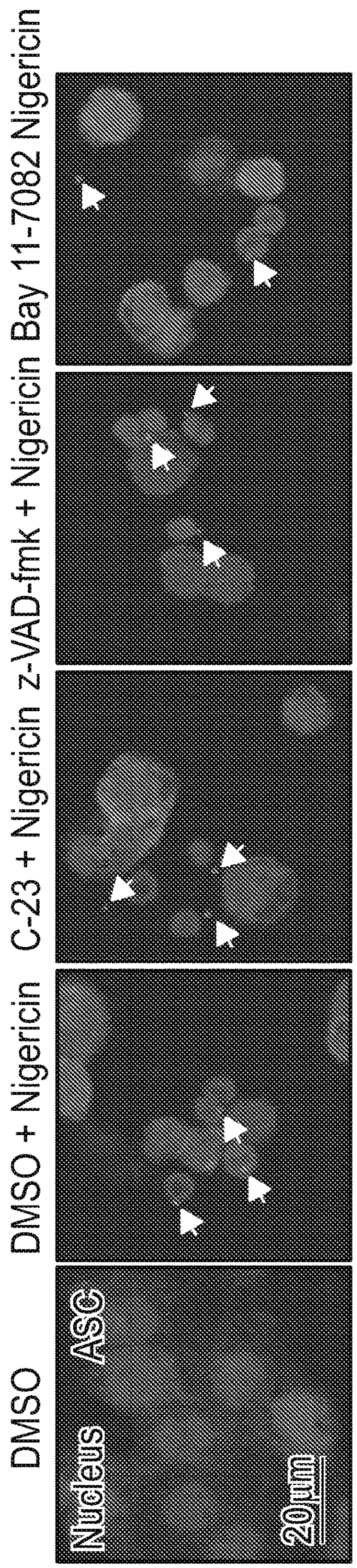
FIG. 46 contains images of LPS-primed THP-1 cells pretreated with C-23, Bay 11-7082 or z-VADfmk.

Because both disulfiram and Bay 11-7082 non-specifically modify reactive Cys, their effects on the steps leading to pyroptosis and inflammatory caspase activation were next analyzed. Some of the genes that participate in the canonical inflammasome pathway are not expressed in unstimulated cells and their expression needs to be induced, often by binding to cell surface sensors of pathogen and danger-associated molecular patterns, such as Toll-like receptors (TLR), in a process called priming. Bay 11-7082 is known to inhibit NF-κB activation, a key transcription factor in priming. The effect of disulfiram and Bay 11-7082 on priming were first examined (FIG. 45). NF-κB activation was assessed by examining IκBu phosphorylation and degradation and RelA (p65) phosphorylation. Induction of pro-IL-1β was assessed by immunoblot for pro-IL1β protein. In the absence of disulfiram or Bay 11-7082, phosphorylation of p65 was first detected 30 min after adding LPS and persisted for 4 hrs, phosphorylation and reduced IκBα were detected 1 hr after adding LPS, and increased pro-IL-1β was detected 4 hrs after adding LPS. Both tested compounds, added at 30 μM concentrations, inhibited NF-κB activation, but Bay 11-7082 had a stronger effect; both blocked pro-IL-1β induction. Thus, disulfiram and Bay 11-7082 both inhibit priming.

Figure 48:
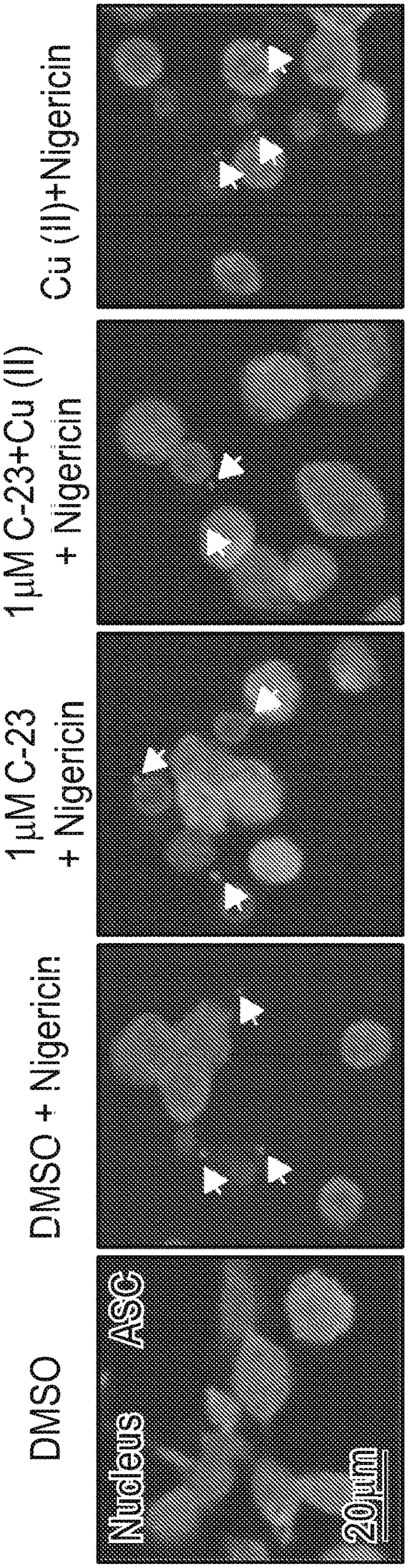
FIG. 48 contains images of LPS-primed THP-1 cells pretreated with C-23, alone or with Cu(II).
Figure 49:
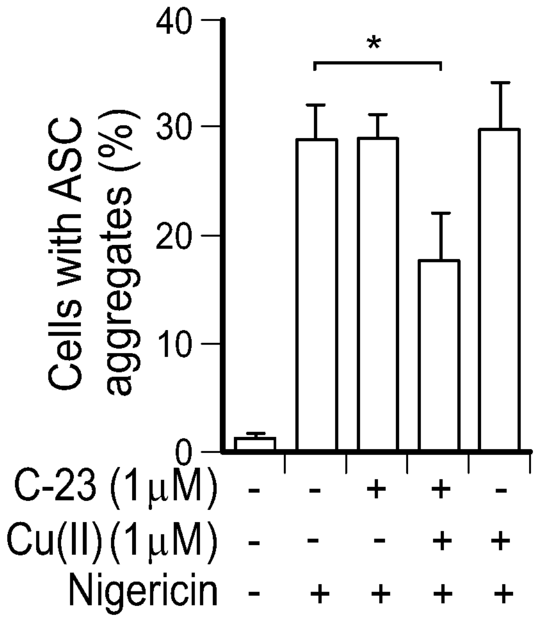
FIG. 49 contains a bar graph showing % of cell with APS aggregates after treatment with C-23, alone or with Cu(II).

Nigericin activates the assembly of the NLRP3 canonical inflammasome using an adaptor called apoptosis-associated speck-like protein containing a caspase recruitment domain (ASC), which can be visualized in immunofluorescent microscopy as specks. When LPS-primed THP-1 cells were treated with nigericin in the absence of inhibitors, ASC specks were detected in 30% of cells (FIG. 36). As expected, speck formation was not inhibited by z-VAD-fmk, since caspase activation occurs downstream of inflammasome assembly. However, both test compounds, added after priming but one hour before nigericin, inhibited ASC speck formation, but not completely, and Bay 11-7082 was more potent than disulfiram when used at the same concentration. 1 μM disulfiram was completely inactive at blocking pyroptosis triggered by nigericin or transfected LPS (FIGS. 6 and 7), but the same concentration of disulfiram in combination with copper gluconate blocked pyroptosis completely and also reduced ASC puncta (FIGS. 48 and 49).

Figure 50:
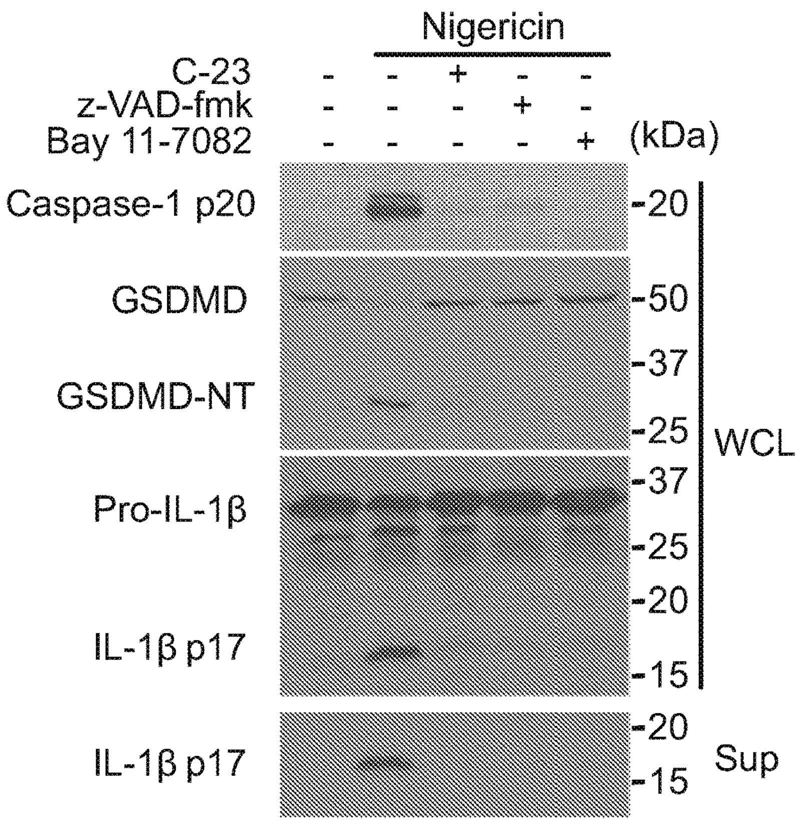
FIG. 50 contains images of immunoblots showing lysates of cells pretreated with C-23, Bay 11-7082 or z-VADfmk and visualized with indicated antibodies.
Figure 51:
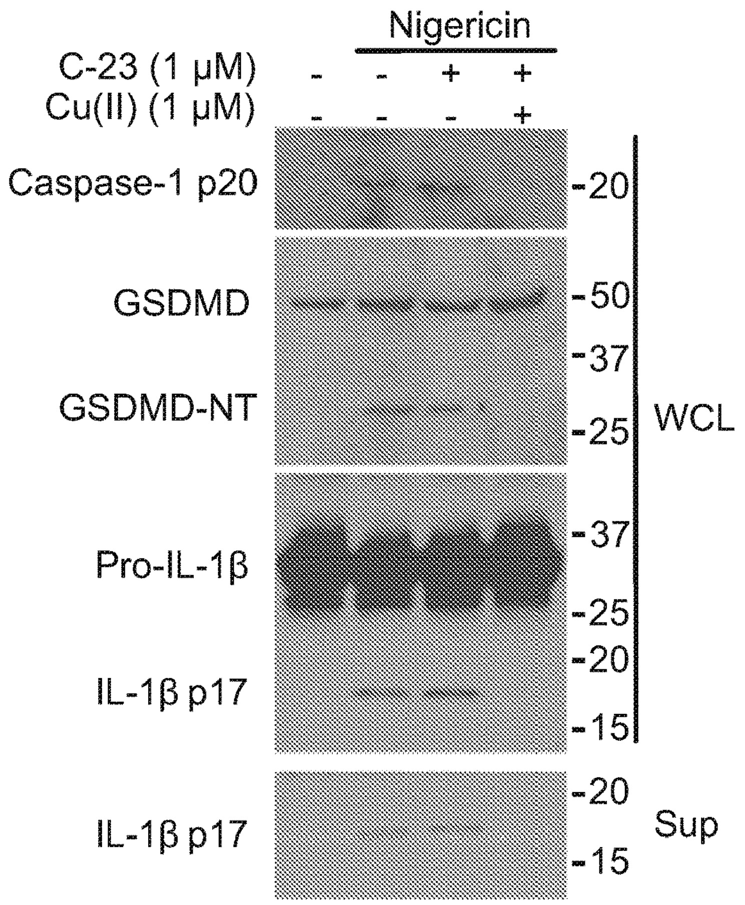
FIG. 51 contains images of immunoblots showing lysates of cells pretreated with C-23, alone or with Cu(II), and visualized with indicated antibodies.
Figure 52:
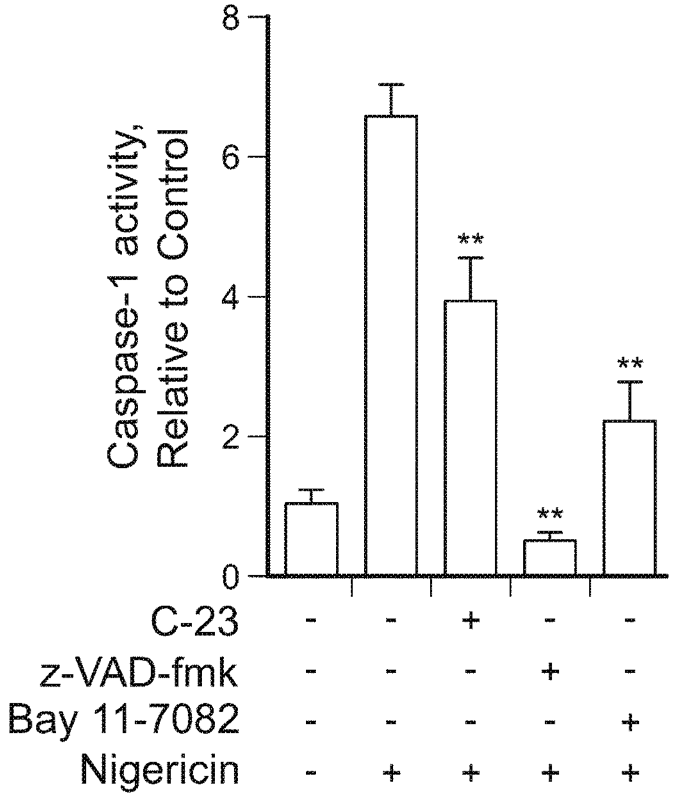
FIG. 52 contains a bar graph showing caspase-1 activity of C-23, Bay 11-7082 and z-VADfmk.

To assess which steps in NLRP3-mediated inflammation were inhibited post ASC speck formation, LPS-primed THP-1 cells were treated with vehicle or 30 μM z-VAD-fmk, disulfiram or Bay 11-7082 1 hr before adding nigericin, and cleavage and activation of caspase-1, GSDMD, and pro-IL-1β were analysed by immunoblot of whole cell lysates 30 min later (FIG. 50). Secretion of processed IL-1β was also assessed by immunoblot of culture supernatants. Caspase-1, GSDMD and pro-IL-1β cleavage to their active forms was clearly detected in the absence of inhibitors, but was dramatically reduced in cells treated by any of the 3 inhibitors; moreover, processed IL-1β was only detected in the culture supernatants in the absence of any inhibitor. When the same experiment was repeated by treating cells with only 1 μM disulfiram in PBS or copper gluconate, disulfiram complexed with copper completely blocked caspase-1, GSDMD, and pro-IL-1β processing and IL-1β secretion, but disulfiram without copper had no effect (FIG. 51). Because immunoblots are not quantitative, caspase-1 activity 30 min after adding nigericin was also assessed using a fluorescent substrate in intact cells. While caspase-1 activity was completely inhibited by z-VAD-fmk, it was only partially reduced by either disulfiram and Bay 11-7082, again more strongly by Bay 11-7082 (FIG. 52). Next, the effect of z-VAD-fmk, disulfiram and Bay 11-7082 on LPS+nigericin-induced GSDMD pore formation was assessed by immunofluorescence microscopy using a monoclonal antibody that was generated that recognizes both uncleaved GSDMD and its pore form (FIGS. 53, 54, and 64-66). In the absence of any inhibitor, the GSDMD antibody stained both the cytosol and the plasma membrane of LPS plus nigericin treated cells, which formed characteristic pyroptotic bubbles (See Reference 10). All 3 inhibitors completely blocked GSDMD membrane staining and the appearance of pyroptotic bubbles. Thus, disulfiram and Bay 11-7082 inhibit multiple steps leading to canonical inflammasome-induced pyroptosis and inflammatory cytokine release, including priming, inflammasome assembly, inflammatory caspase activation, pro-inflammatory cytokine processing and GSDMD pore formation.

Figure 47:
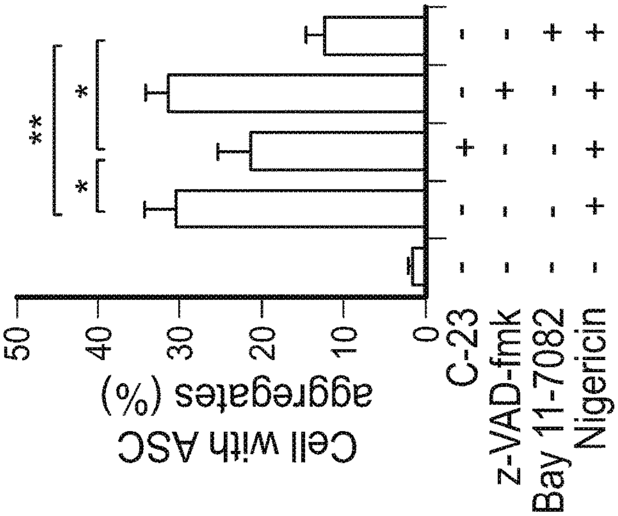
FIG. 47 contains a bar graph showing % of cell with APS aggregates after treatment with C-23, Bay 11-7082 or z-VADfmk.
Figure 53:
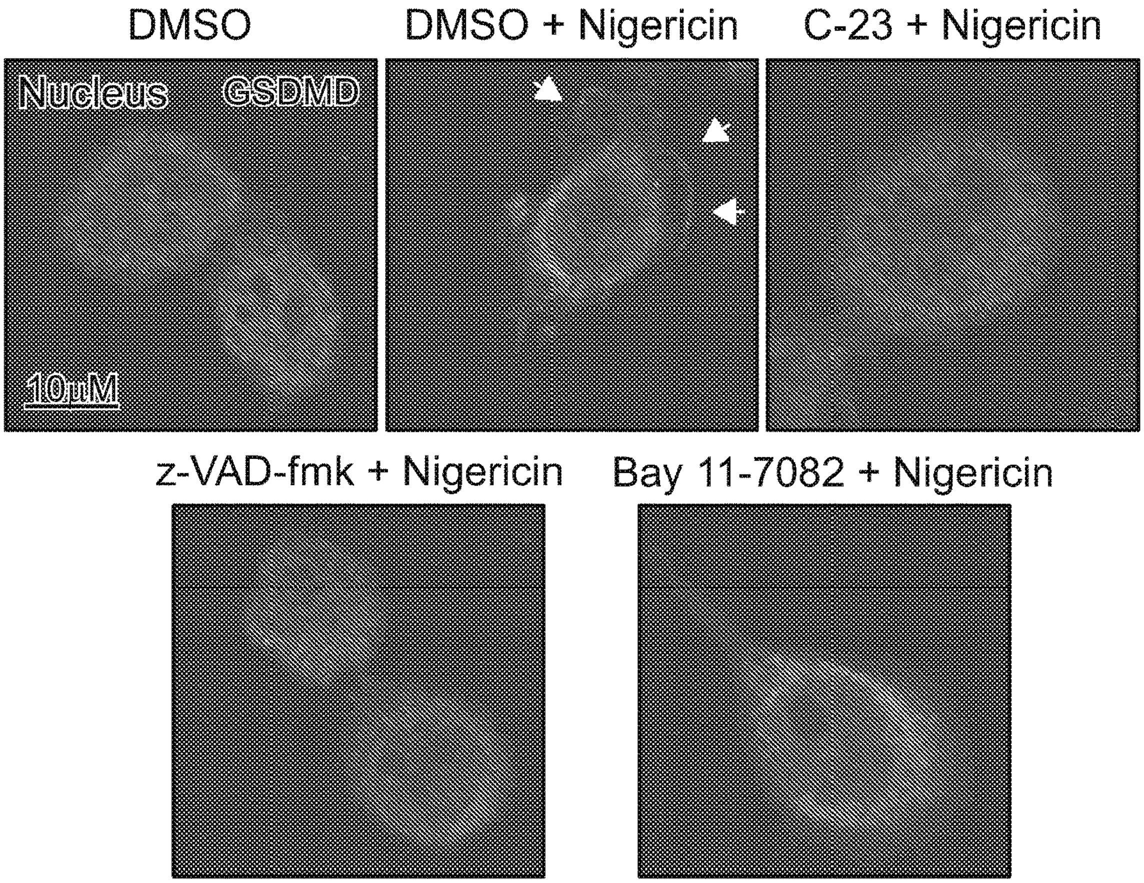
FIG. 53 contains images of LPS-primed THP-1 cells that were pretreated with C-23, Bay 11-7082 or z-VAD-fmk, and stained with a mouse anti-GSDMD monoclonal antibody.
Figure 54:
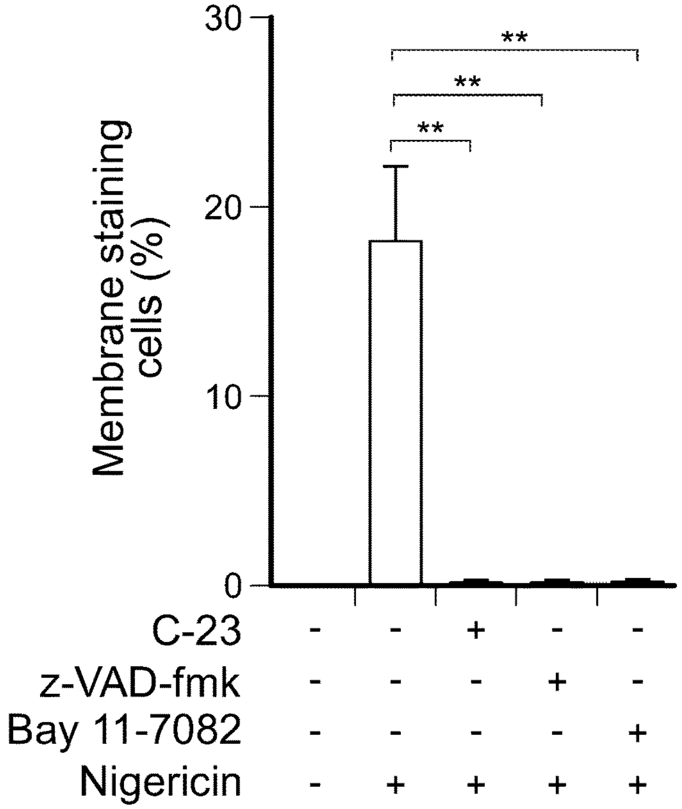
FIG. 54 contains a bar graph showing quantification of proportion of cells with GSDMD membrane staining and pyroptotic bubbles.
Figure 57:
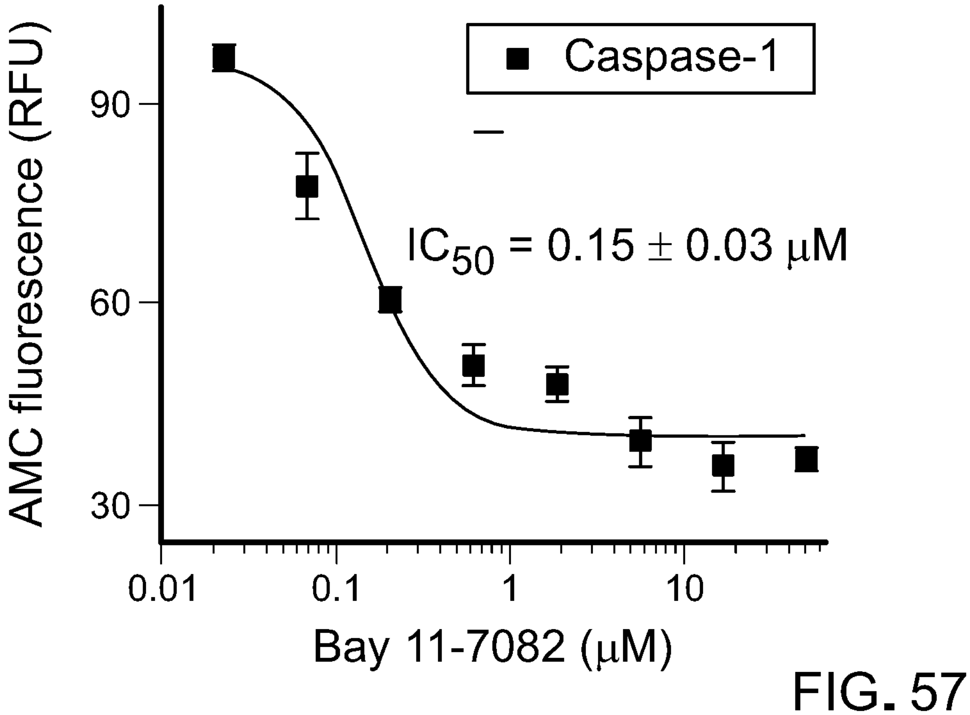
FIG. 57 contains a dose response curve of the effect of Bay 11-7082 on caspase-1 activity.
Figure 58:
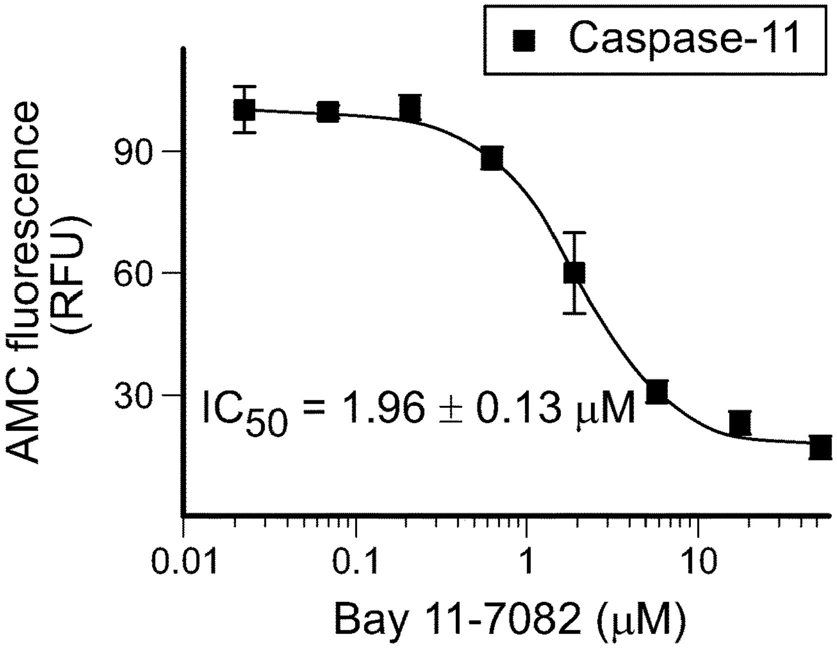
FIG. 58 contains a dose response curve of the effect of Bay 11-7082 on caspase-11 activity.
Figure 59:
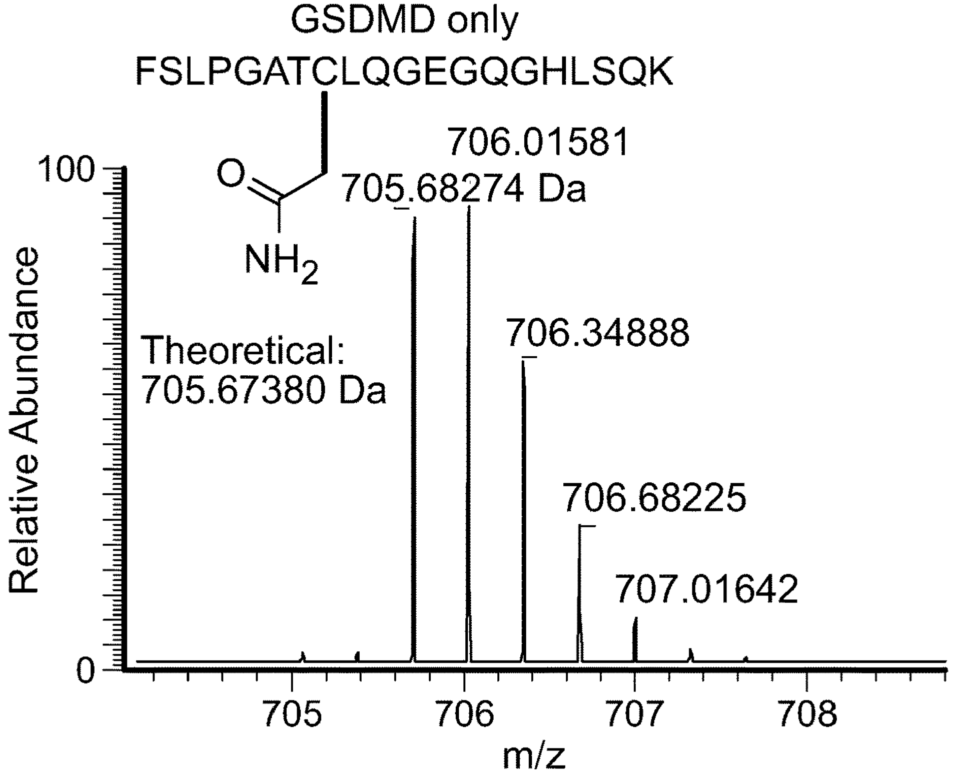
FIG. 59 contains MS spectrum of GSDMD peptide modified on Cys191 by carbamidomethyl.
Figure 60:
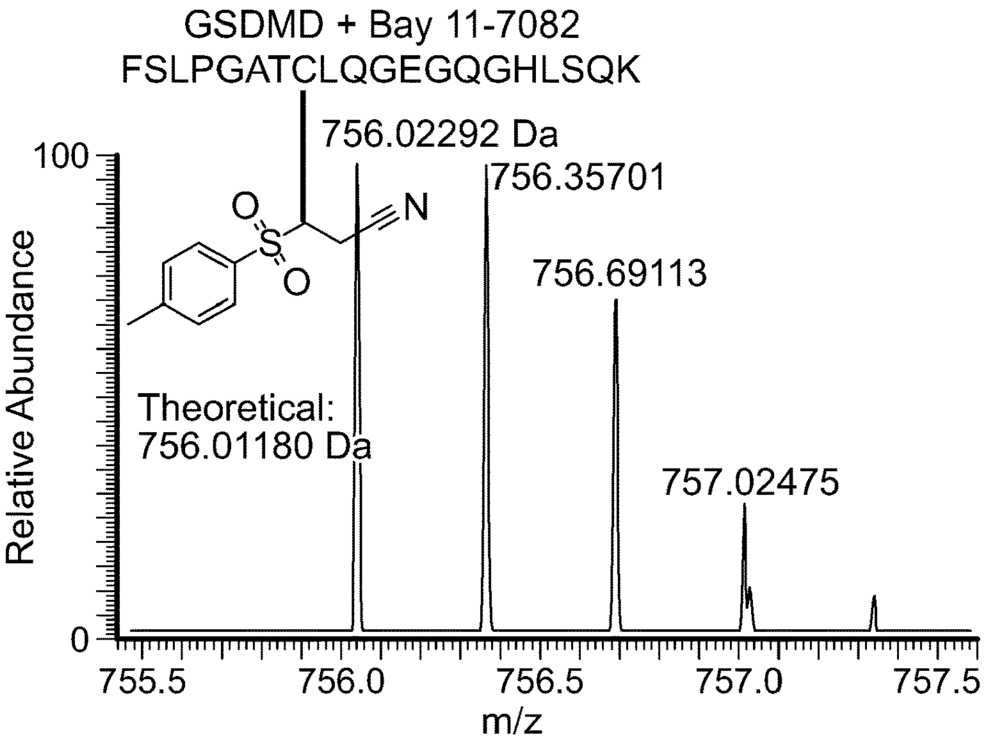
FIG. 60 contains MS spectrum of GSDMD peptide after GSDMD incubation with Bay 11-7082, which was modified at Cys191.
Figure 61:
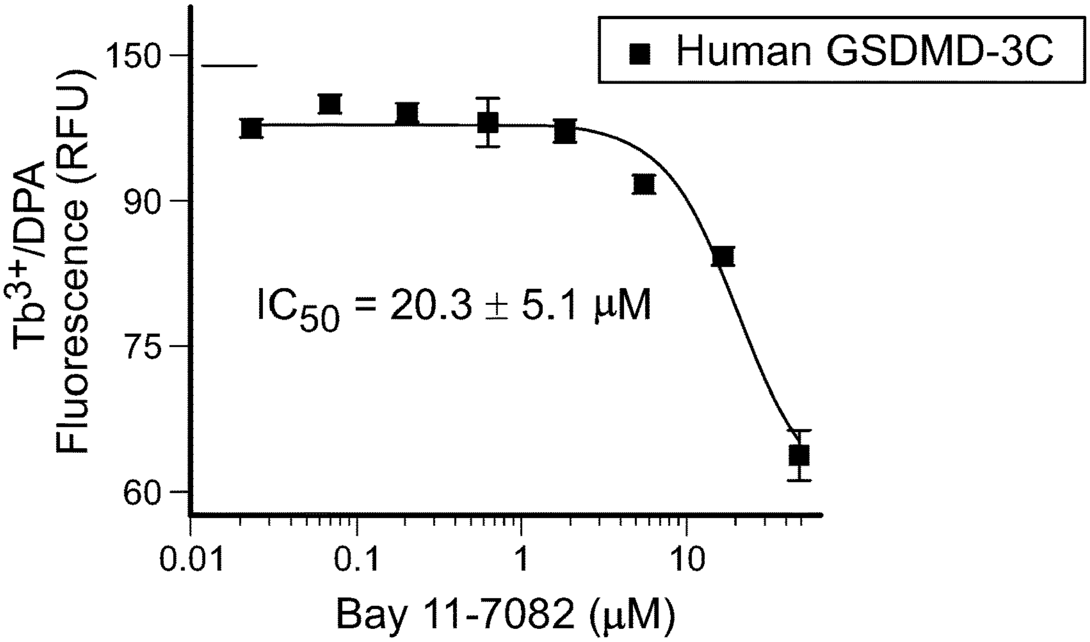
FIG. 61 contains a dose response curve of the effect of Bay 11-7082 on liposome leakage induced by human GSDMD-3C.
Figure 62:
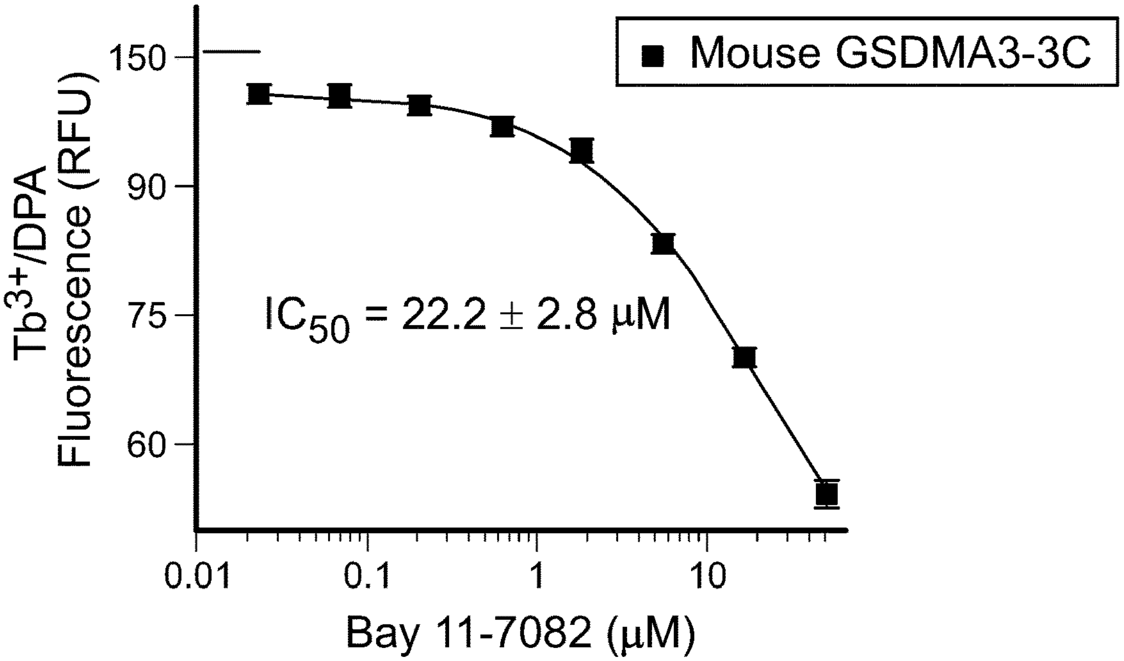
FIG. 62 contains a dose response curve of the effect of Bay 11-7082 on liposome leakage induced by mouse GSDMD-3C.
Figure 63:
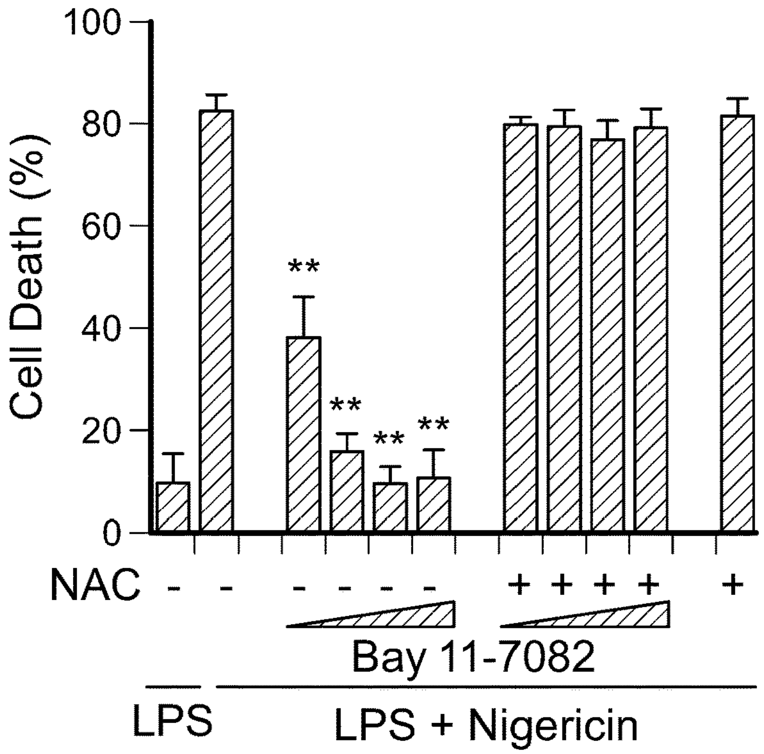
FIG. 63 contains a bar graph showing effect of preincubation of Bay 11-7082 with N-acetylcysteine (NAC) on inhibition of pyroptosis.

Experimental results: In FIG. 43, PMA-differentiated LPS-primed THP-1 cells were pretreated with 2-fold serial dilutions (ranging from 0.3125 to 40 μM) of C-23 and/or Bay 11-7082 for 1 hr before treatment with nigericin. Cell death was determined by CytoTox96 assay. In FIG. 44, mouse iBMDMs were pretreated with serial 2-fold dilutions of C-23 or Bay 11-7082 (ranging from 0.3125 to 40 μM) for 1 hr before electroporation with PBS or LPS. Cell death was determined by CytoTox96 assay. In FIG. 45, THP-1 cells were pretreated with 30 μM C-23 or Bay 11-7082 for 1 hr before adding LPS. Shown are immunoblots of whole cell lysates harvested 0.5 hr later. In FIGS. 46, 47, 50, and 52, LPS-primed THP-1 were pretreated with 30 μM C-23, Bay 11-7082 or z-VAD-fmk for 1 hr before adding nigericin or medium. Representative images of ASC specks (arrowheads) and mean±s.d. percent of cells with ASC specks analyzed 20 min later (FIG. 47). Whole cell lysates (WCL) and culture supernatants (Sup) were harvested 30 min after adding nigericin and immunoblotted with the indicated antibodies (FIG. 50). Caspase-1 activity was assayed 30 min after adding nigericin using a cell-permeable fluorescence dye FAM-YVAD-FMK (FIG. 52). In FIGS. 48, 49 and 51, LPS-primed THP-1 were pretreated with 1 μM C-23 in the presence or absence of Cu(II) for 1 hr before adding nigericin or medium. Representative images of ASC specks (arrowheads) and mean s.d. percent of cells with ASC specks analyzed 20 min later (FIGS. 48 and 49). Whole cell lysates (WCL) and culture supernatants (Sup), harvested 30 min after adding nigericin, were analyzed by immunoblot (FIG. 51). In FIGS. 53 and 54, LPS-primed THP-1 were pretreated with 30 μM C-23, Bay 11-7082 or z-VAD-fmk for 1 hr before adding nigericin or medium and stained with a mouse anti-GSDMD monoclonal antibody (see FIGS. 55-63) 30 min later. The Figurs show representative confocal microscopy images and quantification of proportion of cells with GSDMD membrane staining and pyroptotic bubbles. Arrows indicate GSDMD staining of pyroptotic bubbles. FIG. 55 shows Bay 11-7082 dose response curve of inhibition of liposome leakage by wild-type, C38A or C191A GSDMD (0.3 μM) plus caspase-11 (0.15 μM). FIG. 56 shows MST measurement of the direct binding of Alexa 488-labeled His-MBP-GSDMD (80 nM) with Bay 11-7082 by NanoTemper. FIGS. 57 and 58, dose response curve of the effect of Bay 11-7082 on caspase-1 (FIG. 57) and caspase-11 (FIG. 58) activity against a fluorescent peptide substrate. FIGS. 59 and 60 show MS/MS spectra of the Cys191-containing GSDMD peptide FSLPGATCLQGEGQGHLSQK (aa 184-103; 2057.00 Da) modified on Cys191 by carbamidomethyl (an increase of 57.0214 Da) [LC retention time, 22.85 min; a triplet charged precursor ion m/z 705.6827 (mass: 2114.0481 Da; delta M 2.27 ppm) was observed](FIG. 59) or of the corresponding GSDMD peptide after GSDMD incubation with Bay 11-7082, which was modified on Cys191 (an increase of 207.0354 Da). [LC retention time, 17.20 min; a triplet charged precursor ion m/z 756.0229 (mass: 2264.0688 Da; delta M 11.7 ppm) was observed.](FIG. 60). FIGS. 61 and 62 show dose response curve of the effect of Bay 11-7082 on liposome leakage induced by 0.3 μM human GSDMD-3C (FIG. 61) or mouse GSDMA3-3C (FIG. 62) plus 0.15 μM 3C protease. FIG. 63 shows effect of 1 hr preincubation of Bay 11-7082 with N-acetylcysteine (NAC, 500 μM) on inhibition of pyroptosis of LPS+nigericin treated THP-1 cells. 2-fold dilutions of Bay 11-7082 from 5-40 μM were used. Graphs show the mean±s.d; data are representative of three independent experiments. *P<0.05, **P<0.01.

In comparison with disulfiram, Bay 11-7082 bound to GSDMD with a lower affinity and was 23 times less active at inhibiting liposome leakage ($IC_{50}$ 6.81±0.10 μM vs 0.30±0.01 μM). Bay 11-7082 also inhibited caspase-1, but was about 3 times less active against caspase-11 than disulfiram. Like disulfiram, Bay 11-7082 functions by inactivating reactive Cys residues29,30. By nano-LC-MS/MS, Bay 11-7082 was found to covalently modify Cys191 in GSDMD. However, Bay 11-7082 inhibition of liposome leakage was only reduced 2-fold by substituting C191A GSDMD for WT GSDMD in the assay. Hence, much of Bay 11-7082 inhibition of liposome leakage could be attributed to caspase-11 inhibition, since Bay 11-7082 was substantially less able to inhibit leakage caused by GSDMD-3C plus 3C protease than by GSDMD plus caspase-11 and its activity against mouse GSDMA3-3C, which lacks a comparable reactive cysteine, plus 3C protease was similar to its activity against GSDMD-3C. Therefore, unlike disulfiram, Bay 11-7082 is more of a caspase inhibitor than a GSDMD inhibitor in the liposome leakage assay.

Example 6b—Inhibitors of Inflammasome Activation Cascade

Recently the Cys-reactive necroptotic inhibitor NSA was shown to also inhibit GSDMD-mediated pyroptosis. The potency of disulfiram at inhibiting GSDMD and caspase-11-mediated liposome leakage with that of NSA and other Cys-reactive compounds was compared, including dimethyl fumarate (DMF, a drug for psoriasis and multiple sclerosis), afatinib (a drug that inhibits epidermal growth factor receptor tyrosine kinase), ibrutinib (a drug that inhibits Bruton's tyrosine kinase), and LDC7559. NSA moderately inhibited liposome leakage but was about 30-fold less potent than disulfiram ($IC_{50}$ of 9.50±0.43 μM).

Figure 64:
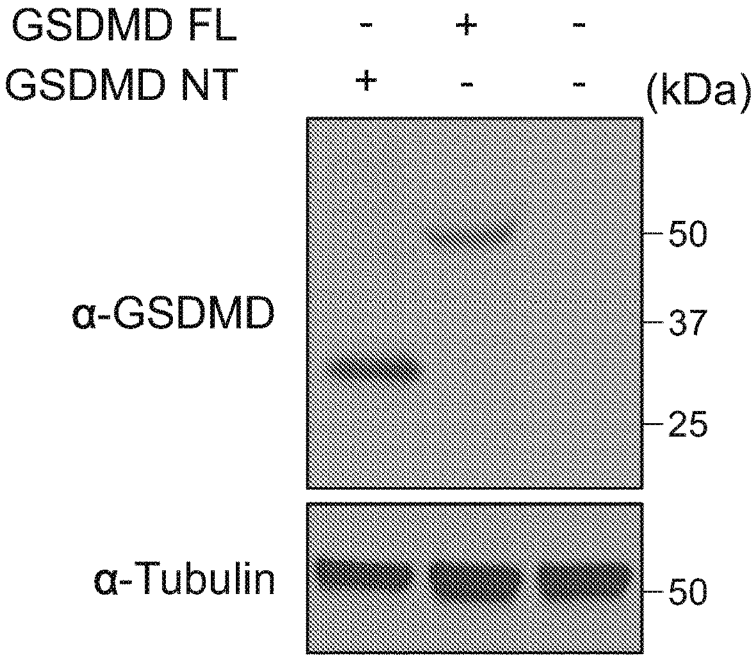
FIG. 64 contains images of immunoblots of HEK293T cells that were transfected with the indicated plasmids, gels were probed with the indicated antibodies.
Figure 65:
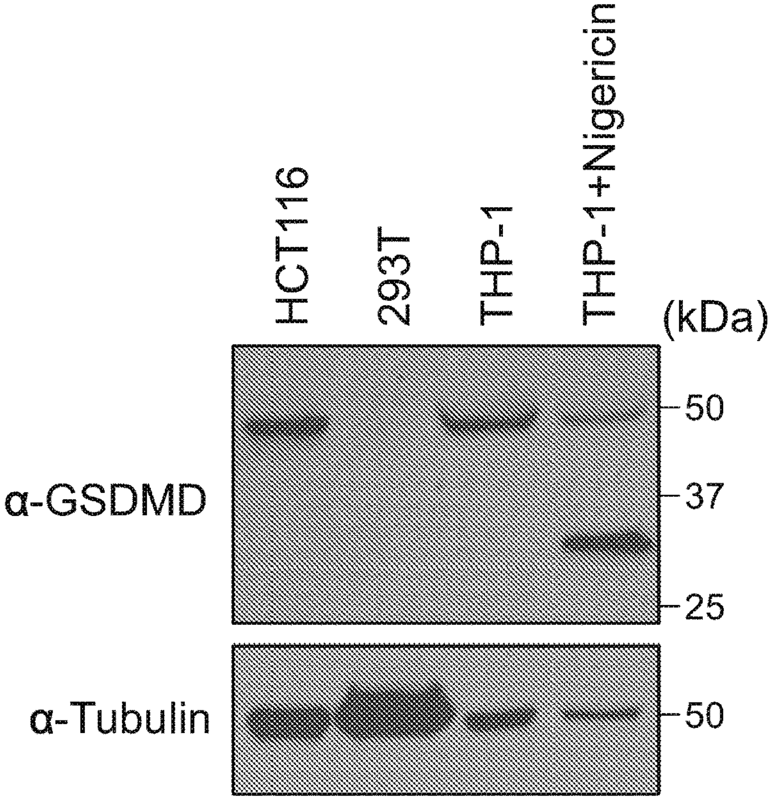
FIG. 65 contains images of immunoblots of HCT116, 293T and THP-1 cells that were transfected with the indicated plasmids, gels were probed with the indicated antibodies.
Figure 66:
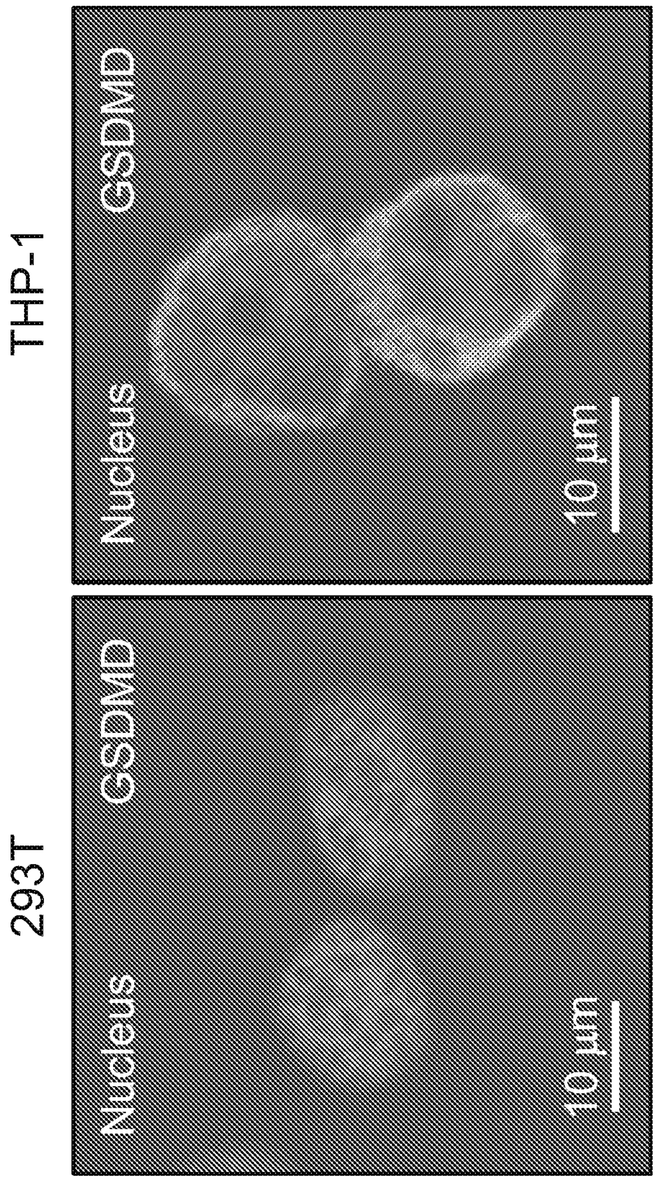
FIG. 66 contains images of 293T and THP-1 cells that were immunostained with the anti-GSDMD monoclonal antibody and co-stained with DAPI FIG. 67 contains a scheme showing biochemical processes leading to the formation of gasdermin D pore and subsequent release of inflammatory mediators.

Example 7—Mouse Monoclonal Antibody Recognizes Full-Length Human GSDMD and the GSDMD-NT Pore Form on Immunoblots and by Immunofluorescence Microscopy The monoclonal antibody against GSDMD was generated by immunizing mice with recombinant human GSDMD and boosting with recombinant human GSDMD-NT as described in Methods. In FIG. 64, HEK293T cells were transfected with the indicated plasmids and cell lysates were analyzed by immunoblot of reducing gels probed with the indicated antibodies. In FIG. 65, cell lysates of HCT116, 293T and THP-1 cells, treated or not with nigericin, were immunoblotted with the indicated antibodies. 293T cells do not express endogenous GSDMD. In FIG. 66, 293T and THP-1 cells were immunostained with the anti-GSDMD monoclonal antibody and co-stained with DAPI (blue). 293T cells that do not express GSDMD show no background staining.

Example 8—Mechanistic Investigation

To elucidate the cellular mechanism of pyroptosis inhibition by disulfiram, its effects on the entire inflammasome activation pathway were analyzed. Some of the genes that participate in the canonical inflammasome pathway are not expressed in unstimulated cells and their expression needs to be induced, often by binding to cell surface sensors of pathogen and danger-associated molecular patterns, such as Toll-like receptors (TLR), in a process called priming. In previous experiments, disulfiram was added 4 hours after LPS priming and 1 hour before stimulating with nigericin and thus the effect of disulfiram in inflammasome priming was not investigated. To look at priming explicitly, THP-1 cells were pretreated with disulfiram for 1 hour before adding LPS for up to 4 hours. NF-κB activation, a key transcription factor in priming, was assessed by examining IκBα phosphorylation and degradation, and RelA (p65) phosphorylation. Induction of NLRP3 and pro-IL-1β expression was assessed by immunoblot. Bay 11-7082 was used as a positive control because of its known inhibitory effect on NF-κB activation. In the absence of disulfiram or Bay 11-7082, phosphorylation of p65 was first detected 30 min after adding LPS and persisted for 4 hours, phosphorylation and reduced IκBα were detected 1 hour after adding LPS, and increased NLRP3 and pro-IL-1β protein were detected 4 hours after adding LPS. Both drugs inhibited NF-κB activation, but Bay 11-7082 had a stronger effect; both blocked NLRP3 and pro-IL-1β induction.

Nigericin activates the assembly of the NLRP3 canonical inflammasome using an adaptor called apoptosis-associated speck-like protein containing a caspase recruitment domain (ASC), which can be visualized in immunofluorescence microscopy as specks. When LPS-primed THP-1 cells were treated with nigericin in the absence of inhibitors, ASC specks were detected in about 30% of cells. As expected, speck formation was not inhibited by z-VAD-fmk, since caspase activation occurs downstream of inflammasome assembly. Disulfiram, added after priming but one hour before nigericin, modestly inhibited ASC speck formation, to about 20% of cells. The modest reduction in speck formation is attributed to subtle inhibition of priming by disulfiram even though it was added after 4 hours of LPS priming. Indeed, immunoblot showed that the NLRP3 level was reduced by disulfiram added after priming compared to cells incubated in medium.

Canonical inflammasome assembly activates caspase-1, which cleaves pro-IL-1β and GSDMD, and the latter is needed to release processed IL-1β and to induce pyroptosis. To assess which steps in NLRP3-mediated inflammation were inhibited post ASC speck formation, LPS-primed THP-1 cells were treated with vehicle, 30 μM z-VAD-fmk or disulfiram 1 hour before adding nigericin, and cleavage and activation of caspase-1, GSDMD, and pro-IL-1β were analysed by immunoblot of whole cell lysates 30 min later and 1 hr later. Secretion of processed IL-1β was also assessed by immunoblot of culture supernatants. Caspase-1, GSDMD and pro-IL-1β cleavage to their active forms was clearly detected in the absence of inhibitors and their processing was reduced in cells treated by disulfiram or z-VAD-fmk at 30 min after nigericin. However, by 60 min, consistent with the weaker effects of disulfiram on caspases, processing of caspase-1, GSDMD and pro-IL-1β in disulfiram-treated samples caught up with what was detected in the absence of inhibitors, while the sample treated with z-VAD-fmk still showed little cleavage of these proteins. The 1 hr time point is relevant as the cell death and IL-1β release measurements used cells stimulated with nigericin for 1 and 2 hrs, respectively. These data suggest that disulfiram delayed, but did not inhibit, caspase-1 activation. However, processed IL-1β was only detected in culture supernatants in the absence of either inhibitor, suggesting that despite limited caspase-1 inhibition, disulfiram completely inhibited cytokine release by blocking GSDMD pore formation. Similar preferential effects of disulfiram on IL-1β release (but not processing) were found in mouse iBMDMs, while NSA, Bay 11-7082 and z-VAD-fmk still inhibited processing of caspase-1, GSDMD and IL-1β at the 1 hr time point.

The effect of z-VAD-fmk and disulfiram on LPS plus nigericin-induced GSDMD pore formation was assessed next by immunofluorescence microscopy using a monoclonal antibody that was generated in the previous example that recognizes both uncleaved GSDMD and its pore form. In the absence of any inhibitor, the GSDMD antibody stained both the cytosol and the plasma membrane of LPS plus nigericin treated cells, which formed characteristic pyroptotic bubbles. Both inhibitors completely blocked GSDMD membrane staining and the appearance of pyroptotic bubbles. Thus, while disulfiram inhibits priming and delays caspase-1 activation, its effects culminate at the bottleneck step of GSDMD pore formation to curtail both pyroptosis and inflammatory cytokine release in both THP-1 and iBMDM cells. In contrast, the control inhibitor z-VAD-fmk blocks exclusively caspase-1 activity.

To investigate the in vivo effect of disulfiram, the LPS-induced sepsis was examined in C57BL/6 mice. Mice were treated with vehicle or disulfiram intraperitoneally before challenge with LPS using a drug dose (50 mg/kg) that was equivalent, after allometric scaling to account for body surface area, to 284 mg/day in humans, which is within the 125-500 mg/day dose range clinically approved to treat alcohol dependence[32]. Whereas the lowest concentration of LPS (15 mg/kg) killed 3 of 8 control mice after 96 hours, all the disulfiram-treated mice survived ($p=0.045$). Serum IL-1β, TNFα and IL-6 concentrations were strongly reduced 12 hours after LPS challenge when all mice were alive ($p \leq 0.0003$). Following LPS challenge at the intermediate concentration (25 mg/kg), all the control mice died within 72 hours, but 5 of 8 of the disulfiram-treated mice survived ($p=0.008$). At the highest LPS challenge (50 mg/kg), while all the control mice died within a day, death was significantly delayed by disulfiram treatment and 1 of 8 mice survived ($p=0.007$). LPS-induced sepsis in mice depends on GSDMD cleavage by caspase-11 in the non-canonical inflammasome. Consistent with previous studies, $Casp11^{-/-}$ and $Gsdmd^{-/-}$ mice, but not $Casp1^{-/-}$, mice were resistant to death from LPS-induced sepsis. As expected, disulfiram protected $Casp1^{-/-}$ mice from lethal LPS challenge but did not significantly affect the survival of $Casp11^{-/-}$ and $Gsdmd^{-/-}$ mice since all but 1 mouse in each undrugged control group survived.

To determine if complexation with Cu(II) could improve protection from sepsis in vivo, the effectiveness of disulfiram administered with or without Cu(II) was compared on survival of mice challenged with 25 mg/kg LPS intraperitoneally. To better mimic the clinical situation where sepsis is usually diagnosed only after the inflammatory cascade has begun, disulfiram administration was deferred until just after LPS injection and 12 hours later. Post-LPS disulfiram treatment significantly delayed death (p=0.041 without Cu(II); p=0.024 with copper). Although all the control mice and mice treated with disulfiram alone died, 2 of 8 mice given Cu(II)-complexed disulfiram survived. The difference in survival between disulfiram treatment with and without Cu(II), however, did not reach significance (p=0.064). Thus, disulfiram given after LPS partially protected mice and administration with Cu(II) may have improved its activity.

LPS not only causes non-canonical inflammasome activation intracellularly, which does not need priming, but also primes NLRP3 inflammasome activation, which amplifies septic shock. Genetic deficiency of NLRP3, ASC, caspase-1, or the IL-1 receptor did not offer substantial survival advantages in mice challenged with LPS in previous studies, while caspase-11 or GSDMD deficiency protected mice from septic death. It is therefore reasoned that protection from LPS-induced sepsis likely depends on inhibiting GSDMD cleavage or pore formation, but not NLRP3 inflammasome priming. This reasoning is supported by our own finding that disulfiram protected $Casp1^{-/-}$ and WT mice similarly.

To determine whether disulfiram mainly inhibits GSDMD processing by caspase-11 or pore formation, four groups of mice were pretreated with disulfiram or vehicle 4 hrs before and immediately before challenge by LPS or vehicle intraperitoneally. Peritoneal macrophages were harvested 6 hrs later and analysed for NLRP3, GSDMD and HMGB1 by immunoblot. GSDMD was equally processed in LPS-challenged groups with or without disulfiram treatment, indicating that suppression of death was due to inhibition of GSDMD pore formation, rather than inhibition of GSDMD cleavage. Surprisingly, NLRP3 levels were also similar in LPS-challenged groups with or without disulfiram treatment, suggesting that even though disulfiram compromised NLRP3 priming in cells, it did not inhibit NLRP3 priming in mice. These results strongly suggest that inhibiting GSDMD pore formation to stop LPS-induced pyroptosis and release of inflammatory mediators is the main target of disulfiram in our model.

Disulfiram inhibition of GSDMD pore formation in mouse and human cells complements its activity in blocking inflammasome priming and caspase activity to suppress pyroptosis and inflammatory cytokine release triggered by both canonical and non-canonical pathways. The simultaneous targeting of three steps in the inflammasome pathway means that disulfiram, especially when given with Cu(II) to stabilize its intermediate, is an especially potent inhibitor of inflammation. The results presented herein indicate that inhibition of pore formation, a common mandatory final step in both pyroptosis and inflammatory mediator release, dominates disulfiram's anti-inflammatory activity. Its relatively weaker activity in inhibiting priming and caspases may have allowed disulfiram to be non-toxic to humans while more potent NF-κB inhibitors such as Bay 11-7082 and caspase inhibitors have both been associated with toxicity. Additionally, the non-canonical inflammasome does not require priming and in disease situations, priming of the relevant immune and epithelial cells may have already occurred by the time signs and symptoms of inflammation are clinically recognized, suggesting that inhibiting GSDMD to stop the most downstream step in pyroptosis and inflammatory mediator release will be especially useful. Finally, the relative selectivity of disulfiram is supported by the lack of activity against GSDMD of a number of other covalent Cys-reactive compounds, including the highly reactive DMF.

REFERENCES

1 Rathinam, V. A., Vanaja, S. K. & Fitzgerald, K. A. Regulation of inflammasome signaling. *Nat Immunol* 13, 333-332 (2012).

2 Lamkanfi, M. & Dixit, V. M. Inflammasomes and their roles in health and disease. *Annu Rev Cell Dev Biol* 28, 137-161 (2012).

3 Jo, E. K., Kim, J. K., Shin, D. M. & Sasakawa, C. Molecular mechanisms regulating NLRP3 inflammasome activation. *Cellular & molecular immunology* 13, 148-159 (2016).

4 Frangogiannis, N. G., Smith, C. W. & Entman, M. L. The inflammatory response in myocardial infarction. *Cardiovasc Res* 53, 31-47 (2002).

5 He, W. T., Wan, H., Hu, L., Chen, P., Wang, X., Huang, Z., Yang, Z. H., Zhong, C. Q. & Han, J. Gasdermin D is an executor of pyroptosis and required for interleukin-1beta secretion. *Cell Res* 25, 1285-1298 (2015).

6 Kayagaki, N., Stowe, I. B., Lee, B. L., O'Rourke, K., Anderson, K., Warming, S., Cuellar, T., Haley, B., Roose-Girma, M., Phung, Q. T., Liu, P. S., Lill, J. R., Li, H., Wu, J., Kummerfeld, S., Zhang, J., Lee, W P., Snipas, S. J., Salvesen, G. S., Morris, L. X., Fitzgerald, L., Zhang, Y., Bertram, E. M., Goodnow, C. C. & Dixit, V. M. Caspase-11 cleaves gasdermin D for non-canonical inflammasome signalling. *Nature* 526, 666-671 (2015).

7 Ding, J., Wang, K., Liu, W., She, Y, Sun, Q., Shi, J., Sun, H., Wang, D. C. & Shao, F. Pore-forming activity and structural autoinhibition of the gasdermin family. *Nature* 535, 111-116 (2016).

8 Liu, X., Zhang, Z., Ruan, J., Pan, Y., Magupalli, V. G., Wu, H. & Lieberman, J. Inflammasome-activated gasdermin D causes pyroptosis by forming membrane pores. *Nature* 535, 153-158 (2016).

9 Sborgi, L., Ravotti, F., Dandey, V. P., Dick, M. S., Mazur, A., Reckel, S., Chami, M., Scherer, S., Huber, M., Bockmann, A., Egelman, E. H., Stahlberg, H., Broz, P., Meier, B. H. & Hiller, S. Structure and assembly of the mouse ASC inflammasome by combined NMR spectroscopy and cryo-electron microscopy. *Proc Natl Acad Sci USA* 112, 13237-13242 (2015).

10 Chen, X., He, W. T., Hu, L., Li, J., Fang, Y., Wang, X., Xu, X., Wang, Z., Huang, K. & Han, J. Pyroptosis is driven by non-selective gasdermin-D pore and its morphology is different from MLKL channel-mediated necroptosis. *Cell Res* 26, 1007-1020 (2016).

11 Russo, H. M., Rathkey, J., Boyd-Tressler, A., Katsnelson, M. A., Abbott, D. W. & Dubyak, G. R. Active Caspase-1 Induces Plasma Membrane Pores That Precede Pyroptotic Lysis and Are Blocked by Lanthanides. *J Immunol* 197, 1353-1367 (2016).

12 Wright, C. & Moore, R. D. Disulfiram treatment of alcoholism. *Am J Med* 88, 647-655 (1990).

13 Pierce, J. W., Schoenleber, R., Jesmok, G., Best, J., Moore, S. A., Collins, T. & Gerritsen, M. E. Novel inhibitors of cytokine-induced IkappaBalpha phosphorylation and endothelial cell adhesion molecule expression show anti-inflammatory effects in vivo. *J Biol Chem* 272, 21096-21103 (1997).

14 Ruan, J., Xia, S., Liu, X., Lieberman, J. & Wu, H. Cryo-EM structure of the gasdermin A3 membrane pore. *Nature* (2018).

15 Baldwin, A. G., Brough, D. & Freeman, S. Inhibiting the Inflammasome: A Chemical Perspective. *J Med Chem* 59, 1691-1710 (2016).

16 Zhou, R., Yazdi, A. S., Menu, P. & Tschopp, J. A role for mitochondria in NLRP3 inflammasome activation. *Nature* 469, 221-225 (2011).

17 Nakahira, K., Haspel, J. A., Rathinam, V. A., Lee, S. J., Dolinay, T., Lam, H. C., Englert, J. A., Rabinovitch, M., Cernadas, M., Kim, H. P., Fitzgerald, K. A., Ryter, S. W. & Choi, A. M. Autophagy proteins regulate innate immune responses by inhibiting the release of mitochondrial DNA mediated by the NALP3 inflammasome. *Nat Immunol* 12, 222-230 (2011).

18 Moon, J. S., Nakahira, K., Chung, K. P., DeNicola, G. M., Koo, M. J., Pabon, M. A., Rooney, K. T., Yoon, J. H., Ryter, S. W., Stout-Delgado, H. & Choi, A. M. NOX4-dependent fatty acid oxidation promotes NLRP3 inflammasome activation in macrophages. *Nat Med* 22, 1002-1012 (2016).

19 Zanoni, I., Tan, Y., Di Gioia, M., Broggi, A., Ruan, J., Shi, J., Donado, C. A., Shao, F., Wu, H., Springstead, J. R. & Kagan, J. C. An endogenous caspase-11 ligand elicits interleukin-1 release from living dendritic cells. *Science* 352, 1232-1236 (2016).

20 Lupfer, C. R., Anand, P. K., Liu, Z., Stokes, K. L., Vogel, P., Lamkanfi, M. & Kanneganti, T. D. Reactive oxygen species regulate caspase-11 expression and activation of the non-canonical NLRP3 inflammasome during enteric pathogen infection. *PLoS Pathog* 10, e1004410 (2014).

21 Chu, L. H., Indramohan, M., Ratsimandresy, R. A., Gangopadhyay, A., Morris, E. P., Monack, D. M., Dorfleutner, A. & Stehlik, C. The oxidized phospholipid oxPAPC protects from septic shock by targeting the non-canonical inflammasome in macrophages. *Nature communications* 9, 996 (2018).

22 Zhong, Z., Umemura, A., Sanchez-Lopez, E., Liang, S., Shalapour, S., Wong, J., He, F., Boassa, D., Perkins, G., Ali, S. R., McGeough, M. D., Ellisman, M. H., Seki, E., Gustafsson, A. B., Hoffman, H. M., Diaz-Meco, M. T., Moscat, J. & Karin, M. NF-kappaB Restricts Inflammasome Activation via Elimination of Damaged Mitochondria. *Cell* 164, 896-910 (2016).

23 Zhang, J. H., Chung, T. D. & Oldenburg, K. R. A Simple Statistical Parameter for Use in Evaluation and Validation of High Throughput Screening Assays. *J Biomol Screen* 4, 67-73 (1999).

24 Skrott, Z., Mistrik, M., Andersen, K. K., Friis, S., Majera, D., Gursky, J., Ozdian, T., Bartkova, J., Turi, Z., Moudry, P., Kraus, M., Michalova, M., Vaclavkova, J., Dzubak, P., Vrobel, I., Pouckova, P., Sedlacek, J., Miklovicova, A., Kutt, A., Li, J., Mattova, J., Driessen, C., Dou, Q. P., Olsen, J., Hajduch, M., Cvek, B., Deshaies, R. J. & Bartek, J. Alcohol-abuse drug disulfiram targets cancer via p97 segregase adaptor NPL4. *Nature* 552, 194-199 (2017).

25 Shen, M. L., Johnson, K. L., Mays, D. C., Lipsky, J. J. & Naylor, S. Determination of in vivo adducts of disulfiram with mitochondrial aldehyde dehydrogenase. *Biochem Pharmacol* 61, 537-545 (2001).

26 Petersen, E. N. The pharmacology and toxicology of disulfiram and its metabolites. *Acta Psychiatr Scand Suppl* 369, 7-13 (1992).

27 Castillo-Villanueva, A., Rufino-Gonzalez, Y., Mendez, S. T., Torres-Arroyo, A., Ponce-Macotela, M., Martinez-Gordillo, M. N., Reyes-Vivas, H. & Oria-Hernandez, J. Disulfiram as a novel inactivator of *Giardia lamblia* triosephosphate isomerase with antigiardial potential. *Int J Parasitol Drugs Drug Resist* 7, 425-432 (2017).

28 Sanchez, R., Riddle, M., Woo, J. & Momand, J. Prediction of reversibly oxidized protein cysteine thiols using protein structure properties. *Protein Sci* 17, 473-481 (2008).

29 Nobel, C. S., Kimland, M., Nicholson, D. W., Orrenius, S. & Slater, A. F. Disulfiram is a potent inhibitor of proteases of the caspase family. *Chem Res Toxicol* 10, 1319-1324 (1997).

30 Irrera, N., Vaccaro, M., Bitto, A., Pallio, G., Pizzino, G., Lentini, M., Arcoraci, V., Minutoli, L., Scuruchi, M., Cutroneo, G., Anastasi, G. P., Ettari, R., Squadrito, F. & Altavilla, D. BAY 11-7082 inhibits the NF-kappaB and NLRP3 inflammasome pathways and protects against IMQ-induced psoriasis. *Clin Sci* (*Lond*) 131, 487-498 (2017).

31 Juliana, C., Fernandes-Alnemri, T., Wu, J., Datta, P., Solorzano, L., Yu, J. W., Meng, R., Quong, A. A., Latz, E., Scott, C. P. & Alnemri, E. S. Anti-inflammatory compounds parthenolide and Bay 11-7082 are direct inhibitors of the inflammasome. *J Biol Chem* 285, 9792-9802 (2010).

32 Krishnan, N., Bencze, G., Cohen, P. & Tonks, N. K. The anti-inflammatory compound BAY-11-7082 is a potent inhibitor of protein tyrosine phosphatases. *The FEBS journal* 280, 2830-2841 (2013).

33 Kulkarni, R. A., Stanford, S. M., Vellore, N. A., Krishnamurthy, D., Bliss, M. R., Baron, R., Bottini, N. & Barrios, A. M. Thiuram disulfides as pseudo-irreversible inhibitors of lymphoid tyrosine phosphatase. *ChemMedChem* 8, 1561-1568 (2013). Broz, P. & Dixit, V. M. Inflammasomes: mechanism of assembly, regulation and signalling. Nat Rev Immunol 16, 407-420 (2016).

34. Shi, J. et al. Cleavage of GSDMD by inflammatory caspases determines pyroptotic cell death. Nature 526, 660-665 (2015).

35. Hagn, F., Nasr, M. L. & Wagner, G. Assembly of phospholipid nanodiscs of controlled size for structural studies of membrane proteins by NMR. Nat Protoc 13, 79-98 (2018).

36. Sun, L. et al. Mixed lineage kinase domain-like protein mediates necrosis signaling downstream of RIP3 kinase. Cell 148, 213-227 (2012).

37. Degterev, A. et al. Identification of RIP1 kinase as a specific cellular target of necrostatins. Nat Chem Biol 4, 313-321 (2008).

38. Rathkey, J. K. et al. Chemical disruption of the pyroptotic pore-forming protein gasdermin D inhibits inflammatory cell death and sepsis. Sci Immunol 3 (2018).

39. Sollberger, G. et al. Gasdermin D plays a vital role in the generation of neutrophil extracellular traps. Sci Immunol 3 (2018).

40. Nair, A. B. & Jacob, S. A simple practice guide for dose conversion between animals and human. J Basic Clin Pharm 7, 27-31 (2016).

41. Kayagaki, N. et al. Non-canonical inflammasome activation targets caspase-11. Nature 479, 117-121 (2011).

42. White, M. J. et al. Apoptotic caspases suppress mtDNA-induced STING-mediated type I IFN production. Cell 159, 1549-1562 (2014).

43. Rongvaux, A. et al. Apoptotic caspases prevent the induction of type I interferons by mitochondrial DNA. Cell 159, 1563-1577 (2014).

44. Rauert-Wunderlich, H. et al. The IKK inhibitor Bay 11-7082 induces cell death independent from inhibition of activation of NFkappaB transcription factors. PLoS One 8, e59292 (2013).

45. Nasr, M. L. et al. Covalently circularized nanodiscs for studying membrane proteins and viral entry. Nat Methods 14, 49-52 (2017).

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A method of treating or preventing sepsis, the method comprises administering to a subject in need thereof a therapeutically effective amount of a compound of Formula (I):

(I)

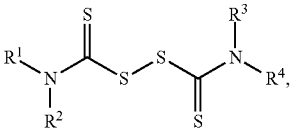

or a pharmaceutically acceptable salt thereof, as the only therapeutic agent, wherein:

$R^1$, $R^2$, $R^3$, and $R^4$ are each $C_{1-4}$ alkyl, or $R^1$ and $R^2$ together with the N atom to which they are attached form a 5-6 membered heterocycloalkyl in which N is the only heteroatom, or $R^3$ and $R^4$ together with the N atom to which they are attached form a 5-6 membered heterocycloalkyl in which N is the only heteroatom.

2. The method of claim 1, wherein the sepsis is acute sepsis.

3. The method of claim 1, wherein the compound of Formula (I) is selected from any one of the following compounds:

C-23

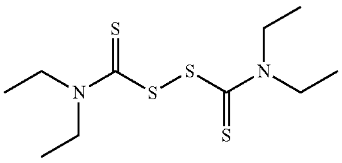

-continued

C-23A1

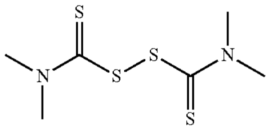

C-23A2

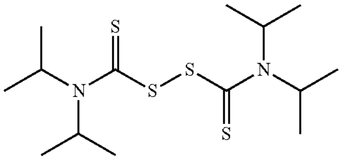

C-23A3

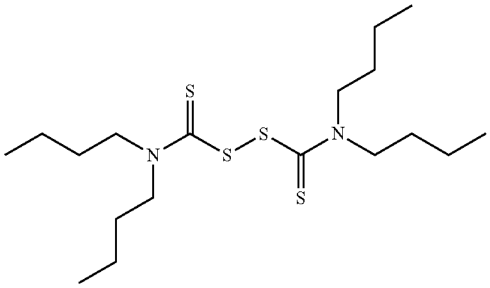

C-23A9

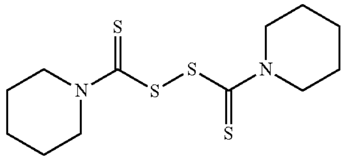

C-23A10

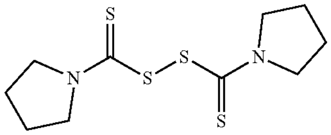

or a pharmaceutically acceptable salt thereof.

* * * * *